(12) United States Patent
Saffari et al.

(10) Patent No.: US 11,197,754 B2
(45) Date of Patent: Dec. 14, 2021

(54) HEART VALVE MIMICRY

(71) Applicant: JENAVALVE TECHNOLOGY, INC., Irvine, CA (US)

(72) Inventors: Payam Saffari, Aliso Viejo, CA (US); Vincent Ming Hai Chow, Irvine, CA (US); Makensley Lordeus, Costa Mesa, CA (US); Hussain S. Rangwala, Villa Park, CA (US); Gregory Edwin Mirigian, Dublin, CA (US); John F. Migliazza, Irvine, CA (US); Victoria E. Carr-Brendel, Irvine, CA (US)

(73) Assignee: JenaValve Technology, Inc., Irvine, CA (US)

( * ) Notice: Subject to any disclaimer, the term of this patent is extended or adjusted under 35 U.S.C. 154(b) by 19 days.

(21) Appl. No.: 16/481,287

(22) PCT Filed: Jan. 25, 2018

(86) PCT No.: PCT/IB2018/050438
§ 371 (c)(1),
(2) Date: Jul. 26, 2019

(87) PCT Pub. No.: WO2018/138658
PCT Pub. Date: Aug. 2, 2018

(65) Prior Publication Data
US 2019/0336281 A1    Nov. 7, 2019

Related U.S. Application Data

(60) Provisional application No. 62/451,296, filed on Jan. 27, 2017.

(51) Int. Cl.
*A61F 2/24*    (2006.01)
*A61B 17/04*   (2006.01)

(52) U.S. Cl.
CPC ........ *A61F 2/2418* (2013.01); *A61B 17/0401* (2013.01); *A61F 2/2415* (2013.01); *A61F 2220/0008* (2013.01); *A61F 2220/0016* (2013.01); *A61F 2220/0075* (2013.01); *A61F 2250/0039* (2013.01); *A61F 2250/0097* (2013.01)

(58) Field of Classification Search
None
See application file for complete search history.

(56) References Cited

U.S. PATENT DOCUMENTS

| 15,192 A | 6/1856 | Peale |
|---|---|---|
| 388,776 A | 8/1888 | Hall |

(Continued)

FOREIGN PATENT DOCUMENTS

| AU | 2004231189 A1 | 12/2004 |
|---|---|---|
| AU | 2004242527 A1 | 1/2005 |

(Continued)

OTHER PUBLICATIONS

US 6,331,185 B1, 12/2001, Gambale et al. (withdrawn)

(Continued)

*Primary Examiner* — Leslie Lopez
(74) *Attorney, Agent, or Firm* — Eversheds Sutherland (US) LLP; Christopher C. Bolten; Robert D. Ward

(57) ABSTRACT

The disclosure relates to a heart valve with improved functionality and durability.

19 Claims, 5 Drawing Sheets

(56) References Cited

U.S. PATENT DOCUMENTS

| | | |
|---|---|---|
| 944,214 A | 12/1909 | Rydquist |
| 2,121,182 A | 6/1938 | Benjamin |
| 2,669,896 A | 2/1954 | Clough |
| 2,682,057 A | 6/1954 | Lord |
| 2,701,559 A | 2/1955 | Cooper |
| 2,832,078 A | 4/1958 | Williams |
| 3,029,819 A | 4/1962 | Edward et al. |
| 3,099,016 A | 7/1963 | Lowell et al. |
| 3,113,586 A | 12/1963 | Edmark, Jr. et al. |
| 3,130,418 A | 4/1964 | Head et al. |
| 3,143,742 A | 8/1964 | Cromie |
| 3,210,836 A | 10/1965 | Johanson et al. |
| 3,221,006 A | 11/1965 | Moore et al. |
| 3,334,629 A | 8/1967 | Cohn |
| 3,365,728 A | 1/1968 | Lowell et al. |
| 3,367,364 A | 2/1968 | Cruz, Jr. et al. |
| 3,409,013 A | 11/1968 | Henry et al. |
| 3,445,916 A | 5/1969 | Schulte et al. |
| 3,540,431 A | 11/1970 | Mobin-Uddin et al. |
| 3,548,417 A | 12/1970 | Kischer et al. |
| 3,570,014 A | 3/1971 | Hancock et al. |
| 3,574,865 A | 4/1971 | Hamaker |
| 3,587,115 A | 6/1971 | Shiley et al. |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,725,961 A | 4/1973 | Magovern et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,983,581 A | 10/1976 | Angell et al. |
| 3,997,923 A | 12/1976 | Possis |
| 4,035,849 A | 7/1977 | Angell et al. |
| 4,056,854 A | 11/1977 | Boretos et al. |
| 4,078,268 A | 3/1978 | Possis |
| 4,084,268 A | 4/1978 | Ionescu et al. |
| 4,106,126 A | 8/1978 | Traenkle |
| 4,106,129 A | 8/1978 | Carpentier et al. |
| 4,118,806 A | 10/1978 | Porier et al. |
| 4,164,046 A | 8/1979 | Cooley |
| 4,182,446 A | 1/1980 | Penny |
| 4,191,218 A | 3/1980 | Clark et al. |
| 4,214,587 A | 7/1980 | Sakura, Jr. |
| 4,215,871 A | 8/1980 | Hirsch et al. |
| 4,222,126 A | 9/1980 | Boretos et al. |
| 4,233,690 A | 11/1980 | Akins |
| 4,261,342 A | 4/1981 | Aranguren Duo |
| 4,263,680 A | 4/1981 | Reul et al. |
| 4,265,694 A | 5/1981 | Boretos et al. |
| 4,291,420 A | 9/1981 | Reul |
| 4,297,749 A | 11/1981 | Davis et al. |
| 4,319,831 A | 3/1982 | Matsui et al. |
| RE30,912 E | 4/1982 | Hancock |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,350,492 A | 9/1982 | Wright et al. |
| 4,373,216 A | 2/1983 | Klawitter |
| 4,388,735 A | 6/1983 | Ionescu et al. |
| 4,406,022 A | 9/1983 | Roy |
| 4,423,809 A | 1/1984 | Mazzocco |
| 4,425,908 A | 1/1984 | Simon |
| 4,441,215 A | 4/1984 | Kaster |
| 4,441,216 A | 4/1984 | Ionescu et al. |
| 4,470,157 A | 9/1984 | Love |
| 4,484,579 A | 11/1984 | Meno et al. |
| 4,485,816 A | 12/1984 | Krumme |
| 4,491,986 A | 1/1985 | Gabbay |
| 4,501,030 A | 2/1985 | Lane |
| 4,502,488 A | 3/1985 | Degironimo et al. |
| 4,531,943 A | 7/1985 | Van Tassel et al. |
| 4,535,483 A | 8/1985 | Klawitter et al. |
| 4,546,499 A | 10/1985 | Possis et al. |
| 4,562,597 A | 1/1986 | Possis et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Kornberg |
| 4,619,246 A | 10/1986 | Molgaard-Nielsen et al. |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | DiPisa, Jr. |
| 4,665,906 A | 5/1987 | Jervis |
| 4,665,918 A | 5/1987 | Garza et al. |
| 4,680,031 A | 7/1987 | Alonso |
| 4,681,908 A | 7/1987 | Broderick et al. |
| 4,687,483 A | 8/1987 | Fisher et al. |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz |
| 4,755,181 A | 7/1988 | Igoe |
| 4,759,758 A | 7/1988 | Gabbay |
| 4,769,029 A | 9/1988 | Patel |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,797,901 A | 1/1989 | Goerne et al. |
| 4,806,595 A | 2/1989 | Noishiki et al. |
| 4,819,751 A | 4/1989 | Shimada et al. |
| 4,829,990 A | 5/1989 | Thuroff et al. |
| 4,834,755 A | 5/1989 | Silvestrini et al. |
| 4,846,830 A | 7/1989 | Knoch et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |
| 4,927,426 A | 5/1990 | Dretler |
| 4,950,227 A | 8/1990 | Savin et al. |
| 4,953,553 A | 9/1990 | Tremulis |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,002,566 A | 3/1991 | Carpentier et al. |
| 5,007,896 A | 4/1991 | Shiber |
| 5,026,366 A | 6/1991 | Leckrone |
| 5,026,377 A | 6/1991 | Burton et al. |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Samuels |
| 5,053,008 A | 10/1991 | Bajaj |
| 5,059,177 A | 10/1991 | Towne et al. |
| 5,061,273 A | 10/1991 | Yock |
| 5,061,277 A | 10/1991 | Carpentier et al. |
| 5,064,435 A | 11/1991 | Porter |

(56) References Cited

U.S. PATENT DOCUMENTS

| | | |
|---|---|---|
| 5,078,720 A | 1/1992 | Burton et al. |
| 5,080,668 A | 1/1992 | Bolz et al. |
| 5,085,635 A | 2/1992 | Cragg |
| 5,089,015 A | 2/1992 | Ross |
| 5,094,661 A | 3/1992 | Levy et al. |
| 5,104,399 A | 4/1992 | Lazarus |
| 5,104,407 A | 4/1992 | Lam et al. |
| 5,108,425 A | 4/1992 | Hwang |
| 5,122,154 A | 6/1992 | Rhodes |
| 5,132,473 A | 7/1992 | Furutaka et al. |
| 5,141,494 A | 8/1992 | Danforth et al. |
| 5,143,987 A | 9/1992 | Hansel et al. |
| 5,147,388 A | 9/1992 | Yamazaki |
| 5,152,771 A | 10/1992 | Sabbaghian et al. |
| 5,159,937 A | 11/1992 | Tremulis |
| 5,161,547 A | 11/1992 | Tower |
| 5,163,953 A | 11/1992 | Vince |
| 5,163,955 A | 11/1992 | Love et al. |
| 5,167,628 A | 12/1992 | Boyles |
| 5,178,632 A | 1/1993 | Hanson |
| 5,192,301 A | 3/1993 | Kamiya et al. |
| 5,193,546 A | 3/1993 | Shaknovich |
| 5,197,979 A | 3/1993 | Quintero et al. |
| 5,201,757 A | 4/1993 | Heyn et al. |
| 5,207,695 A | 5/1993 | Trout, III |
| 5,209,741 A | 5/1993 | Spaeth |
| 5,211,183 A | 5/1993 | Wilson |
| 5,215,541 A | 6/1993 | Nashef et al. |
| 5,217,481 A | 6/1993 | Barbara |
| 5,217,483 A | 6/1993 | Tower |
| 5,232,445 A | 8/1993 | Bonzel |
| 5,234,447 A | 8/1993 | Kaster et al. |
| 5,234,456 A | 8/1993 | Silvestrini |
| 5,238,004 A | 8/1993 | Sahatjian et al. |
| 5,258,008 A | 11/1993 | Wilk |
| 5,258,023 A | 11/1993 | Reger |
| 5,258,042 A | 11/1993 | Mehta |
| 5,272,909 A | 12/1993 | Nguyen et al. |
| 5,275,580 A | 1/1994 | Yamazaki |
| 5,279,612 A | 1/1994 | Eberhardt |
| 5,282,847 A | 2/1994 | Trescony et al. |
| 5,287,861 A | 2/1994 | Wilk |
| 5,295,958 A | 3/1994 | Shturman |
| 5,327,774 A | 7/1994 | Nguyen et al. |
| 5,330,486 A | 7/1994 | Wilk |
| 5,330,500 A | 7/1994 | Song |
| 5,332,402 A | 7/1994 | Teitelbaum |
| 5,336,258 A | 8/1994 | Quintero et al. |
| 5,342,348 A | 8/1994 | Kaplan |
| 5,344,426 A | 9/1994 | Lau et al. |
| 5,344,427 A | 9/1994 | Cottenceau et al. |
| 5,344,442 A | 9/1994 | Deac |
| 5,350,398 A | 9/1994 | Pavcnik et al. |
| 5,350,399 A | 9/1994 | Erlebacher et al. |
| 5,352,240 A | 10/1994 | Ross |
| 5,354,330 A | 10/1994 | Hanson et al. |
| 5,360,444 A | 11/1994 | Kusuhara |
| 5,368,608 A | 11/1994 | Levy et al. |
| 5,370,685 A | 12/1994 | Stevens |
| 5,380,054 A | 1/1995 | Galvis |
| 5,387,235 A | 2/1995 | Chuter |
| 5,389,096 A | 2/1995 | Aita et al. |
| 5,389,106 A | 2/1995 | Tower |
| 5,397,351 A | 3/1995 | Pavcnik et al. |
| 5,397,355 A | 3/1995 | Marin et al. |
| 5,409,019 A | 4/1995 | Wilk |
| 5,411,552 A | 5/1995 | Andersen et al. |
| 5,415,633 A | 5/1995 | Lazarus et al. |
| 5,425,739 A | 6/1995 | Jessen |
| 5,425,762 A | 6/1995 | Muller |
| 5,429,144 A | 7/1995 | Wilk |
| 5,431,676 A | 7/1995 | Dubrul et al. |
| 5,433,723 A | 7/1995 | Lindenberg et al. |
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 5,449,384 A | 9/1995 | Johnson |
| 5,456,712 A | 10/1995 | Maginot |
| 5,456,713 A | 10/1995 | Chuter |
| 5,464,449 A | 11/1995 | Ryan et al. |
| 5,469,868 A | 11/1995 | Reger |
| 5,470,320 A | 11/1995 | Tiefenbrun et al. |
| 5,476,506 A | 12/1995 | Lunn |
| 5,476,508 A | 12/1995 | Amstrup |
| 5,476,510 A | 12/1995 | Eberhardt et al. |
| 5,480,423 A | 1/1996 | Ravenscroft et al. |
| 5,480,424 A | 1/1996 | Cox |
| 5,486,193 A | 1/1996 | Bourne et al. |
| 5,487,760 A | 1/1996 | Villafana |
| 5,489,294 A | 2/1996 | McVenes et al. |
| 5,489,297 A | 2/1996 | Duran |
| 5,489,298 A | 2/1996 | Love et al. |
| 5,496,346 A | 3/1996 | Horzewski et al. |
| 5,499,995 A | 3/1996 | Teirstein |
| 5,500,014 A | 3/1996 | Quijano et al. |
| 5,500,015 A | 3/1996 | Deac |
| 5,507,767 A | 4/1996 | Maeda et al. |
| 5,509,930 A | 4/1996 | Love |
| 5,522,881 A | 6/1996 | Lentz |
| 5,527,337 A | 6/1996 | Stack et al. |
| 5,530,949 A | 6/1996 | Koda et al. |
| 5,534,007 A | 7/1996 | St. Germain et al. |
| 5,540,712 A | 7/1996 | Kleshinski et al. |
| 5,545,133 A | 8/1996 | Burns et al. |
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,549,666 A | 8/1996 | Hata et al. |
| 5,554,119 A | 9/1996 | Harrison et al. |
| 5,554,185 A | 9/1996 | Block et al. |
| 5,569,274 A | 10/1996 | Rapacki et al. |
| 5,571,167 A | 11/1996 | Maginot |
| 5,571,174 A | 11/1996 | Love et al. |
| 5,571,175 A | 11/1996 | Vanney et al. |
| 5,571,215 A | 11/1996 | Sterman et al. |
| 5,573,520 A | 11/1996 | Schwartz et al. |
| 5,575,818 A | 11/1996 | Pinchuk |
| 5,580,922 A | 12/1996 | Park et al. |
| 5,591,185 A | 1/1997 | Kilmer et al. |
| 5,591,195 A | 1/1997 | Taheri et al. |
| 5,593,434 A | 1/1997 | Williams |
| 5,595,571 A | 1/1997 | Jaffe et al. |
| 5,596,471 A | 1/1997 | Hanlin |
| 5,607,464 A | 3/1997 | Trescony et al. |
| 5,607,465 A | 3/1997 | Camilli |
| 5,609,626 A | 3/1997 | Quijano et al. |
| 5,613,982 A | 3/1997 | Goldstein |
| 5,618,299 A | 4/1997 | Khosravi et al. |
| 5,626,553 A | 5/1997 | Frassica et al. |
| 5,628,784 A | 5/1997 | Strecker |
| 5,632,778 A | 5/1997 | Goldstein |
| 5,634,942 A | 6/1997 | Chevillon et al. |
| 5,643,278 A | 7/1997 | Wijay |
| 5,645,559 A | 7/1997 | Hachtman et al. |
| 5,653,684 A | 8/1997 | Laptewicz et al. |
| 5,653,745 A | 8/1997 | Trescony et al. |
| 5,653,749 A | 8/1997 | Love et al. |
| 5,655,548 A | 8/1997 | Nelson et al. |
| 5,662,124 A | 9/1997 | Wilk |
| 5,662,671 A | 9/1997 | Barbut et al. |
| 5,662,703 A | 9/1997 | Yurek et al. |
| 5,665,115 A | 9/1997 | Cragg |
| 5,667,523 A | 9/1997 | Bynon et al. |
| 5,674,277 A | 10/1997 | Freitag |
| 5,674,298 A | 10/1997 | Levy et al. |
| 5,679,112 A | 10/1997 | Levy et al. |
| 5,681,345 A | 10/1997 | Euteneuer |
| 5,682,906 A | 11/1997 | Sterman et al. |
| 5,683,451 A | 11/1997 | Lenker et al. |
| 5,690,644 A | 11/1997 | Yurek et al. |
| 5,693,083 A | 12/1997 | Baker et al. |

(56) References Cited

U.S. PATENT DOCUMENTS

| | | |
|---|---|---|
| 5,693,088 A | 12/1997 | Lazarus |
| 5,693,310 A | 12/1997 | Gries et al. |
| 5,695,498 A | 12/1997 | Tower |
| 5,697,972 A | 12/1997 | Kim et al. |
| 5,700,269 A | 12/1997 | Pinchuk et al. |
| 5,702,368 A | 12/1997 | Stevens et al. |
| 5,709,713 A | 1/1998 | Evans et al. |
| 5,713,917 A | 2/1998 | Leonhardt et al. |
| 5,713,950 A | 2/1998 | Cox |
| 5,713,951 A | 2/1998 | Garrison et al. |
| 5,713,953 A | 2/1998 | Vallana et al. |
| 5,716,370 A | 2/1998 | Williamson, IV et al. |
| 5,716,417 A | 2/1998 | Girard et al. |
| 5,718,725 A | 2/1998 | Sterman et al. |
| 5,720,391 A | 2/1998 | Dohm et al. |
| 5,720,776 A | 2/1998 | Chuter et al. |
| 5,725,549 A | 3/1998 | Lam |
| 5,725,550 A | 3/1998 | Nadal |
| 5,728,068 A | 3/1998 | Leone et al. |
| 5,728,151 A | 3/1998 | Garrison et al. |
| 5,733,267 A | 3/1998 | Del Toro |
| 5,733,325 A | 3/1998 | Robinson et al. |
| 5,735,842 A | 4/1998 | Krueger et al. |
| 5,746,476 A | 5/1998 | Novak et al. |
| 5,746,709 A | 5/1998 | Rom et al. |
| 5,746,765 A | 5/1998 | Kleshinski et al. |
| 5,746,775 A | 5/1998 | Levy et al. |
| 5,749,890 A | 5/1998 | Shaknovich |
| 5,749,921 A | 5/1998 | Lenker et al. |
| 5,755,682 A | 5/1998 | Knudson et al. |
| 5,755,777 A | 5/1998 | Chuter |
| 5,755,783 A | 5/1998 | Stobie et al. |
| 5,756,476 A | 5/1998 | Epstein et al. |
| 5,758,663 A | 6/1998 | Wilk et al. |
| 5,766,151 A | 6/1998 | Valley et al. |
| 5,769,780 A | 6/1998 | Hata et al. |
| 5,769,812 A | 6/1998 | Stevens et al. |
| 5,769,882 A | 6/1998 | Fogarty et al. |
| 5,769,887 A | 6/1998 | Brown et al. |
| 5,772,609 A | 6/1998 | Nguyen et al. |
| 5,776,188 A | 7/1998 | Shepherd et al. |
| 5,782,809 A | 7/1998 | Umeno et al. |
| 5,782,904 A | 7/1998 | White et al. |
| 5,795,331 A | 8/1998 | Cragg et al. |
| 5,797,946 A | 8/1998 | Chin |
| 5,797,960 A | 8/1998 | Stevens et al. |
| 5,799,661 A | 9/1998 | Boyd et al. |
| 5,800,456 A | 9/1998 | Maeda et al. |
| 5,800,508 A | 9/1998 | Goicoechea et al. |
| 5,800,531 A | 9/1998 | Cosgrove et al. |
| 5,807,327 A | 9/1998 | Green et al. |
| 5,807,384 A | 9/1998 | Mueller |
| 5,807,405 A | 9/1998 | Vanney et al. |
| 5,810,836 A | 9/1998 | Hussein et al. |
| 5,814,016 A | 9/1998 | Valley et al. |
| 5,817,113 A | 10/1998 | Gifford, III et al. |
| 5,817,126 A | 10/1998 | Imran |
| 5,823,956 A | 10/1998 | Roth et al. |
| 5,824,037 A | 10/1998 | Fogarty et al. |
| 5,824,038 A | 10/1998 | Wall |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,061 A | 10/1998 | Quijano et al. |
| 5,824,063 A | 10/1998 | Cox |
| 5,824,064 A | 10/1998 | Taheri |
| 5,824,071 A | 10/1998 | Nelson et al. |
| 5,824,080 A | 10/1998 | Lamuraglia |
| 5,829,447 A | 11/1998 | Stevens et al. |
| 5,830,222 A | 11/1998 | Makower |
| 5,840,081 A | 11/1998 | Andersen et al. |
| 5,841,382 A | 11/1998 | Walden et al. |
| 5,843,158 A | 12/1998 | Lenker et al. |
| 5,843,161 A | 12/1998 | Solovay |
| 5,843,181 A | 12/1998 | Jaffe et al. |
| 5,851,232 A | 12/1998 | Lois |
| 5,853,419 A | 12/1998 | Imran |
| 5,853,420 A | 12/1998 | Chevillon et al. |
| 5,855,210 A | 1/1999 | Sterman et al. |
| 5,855,597 A | 1/1999 | Jayaraman |
| 5,855,600 A | 1/1999 | Alt |
| 5,855,601 A | 1/1999 | Bessler et al. |
| 5,855,602 A | 1/1999 | Angell |
| 5,860,966 A | 1/1999 | Tower |
| 5,860,996 A | 1/1999 | Urban et al. |
| 5,861,024 A | 1/1999 | Rashidi |
| 5,861,028 A | 1/1999 | Angell |
| 5,865,723 A | 2/1999 | Love |
| 5,868,783 A | 2/1999 | Tower |
| 5,873,812 A | 2/1999 | Ciana et al. |
| 5,873,906 A | 2/1999 | Lau et al. |
| 5,876,373 A | 3/1999 | Giba et al. |
| 5,876,419 A | 3/1999 | Carpenter et al. |
| 5,876,434 A | 3/1999 | Flomenblit et al. |
| 5,876,448 A | 3/1999 | Thompson et al. |
| 5,878,751 A | 3/1999 | Hussein et al. |
| 5,880,242 A | 3/1999 | Hu et al. |
| 5,885,228 A | 3/1999 | Rosenman et al. |
| 5,885,238 A | 3/1999 | Stevens et al. |
| 5,885,259 A | 3/1999 | Berg |
| 5,888,201 A | 3/1999 | Stinson et al. |
| 5,891,160 A | 4/1999 | Williamson, IV et al. |
| 5,891,191 A | 4/1999 | Stinson |
| 5,895,399 A | 4/1999 | Barbut et al. |
| 5,895,420 A | 4/1999 | Mirsch, II et al. |
| 5,899,936 A | 5/1999 | Goldstein |
| 5,906,619 A | 5/1999 | Olson et al. |
| 5,907,893 A | 6/1999 | Zadno-Azizi et al. |
| 5,908,028 A | 6/1999 | Wilk |
| 5,908,029 A | 6/1999 | Knudson et al. |
| 5,908,451 A | 6/1999 | Yeo |
| 5,908,452 A | 6/1999 | Bokros et al. |
| 5,910,144 A | 6/1999 | Hayashi |
| 5,910,154 A | 6/1999 | Tsugita et al. |
| 5,911,734 A | 6/1999 | Tsugita et al. |
| 5,911,752 A | 6/1999 | Dustrude et al. |
| 5,913,842 A | 6/1999 | Boyd et al. |
| 5,916,193 A | 6/1999 | Stevens et al. |
| 5,922,022 A | 7/1999 | Nash et al. |
| 5,924,424 A | 7/1999 | Stevens et al. |
| 5,925,012 A | 7/1999 | Murphy-Chutorian et al. |
| 5,925,063 A | 7/1999 | Khosravi |
| 5,928,281 A | 7/1999 | Huynh et al. |
| 5,931,848 A | 8/1999 | Saadat |
| 5,935,119 A | 8/1999 | Guy et al. |
| 5,935,161 A | 8/1999 | Robinson et al. |
| 5,935,163 A | 8/1999 | Gabbay |
| 5,938,632 A | 8/1999 | Ellis |
| 5,938,697 A | 8/1999 | Killion et al. |
| 5,941,908 A | 8/1999 | Goldsteen et al. |
| 5,944,019 A | 8/1999 | Knudson et al. |
| 5,944,738 A | 8/1999 | Amplatz et al. |
| 5,948,017 A | 9/1999 | Taheri |
| 5,954,764 A | 9/1999 | Parodi |
| 5,954,766 A | 9/1999 | Zadno-Azizi et al. |
| 5,957,949 A | 9/1999 | Leonhardt et al. |
| 5,961,549 A | 10/1999 | Nguyen et al. |
| 5,964,405 A | 10/1999 | Benary et al. |
| 5,964,798 A | 10/1999 | Imran |
| 5,968,064 A | 10/1999 | Selmon et al. |
| 5,968,068 A | 10/1999 | Dehdashtian et al. |
| 5,968,070 A | 10/1999 | Bley et al. |
| 5,971,993 A | 10/1999 | Hussein et al. |
| 5,975,949 A | 11/1999 | Holliday et al. |
| 5,976,153 A | 11/1999 | Fischell et al. |
| 5,976,155 A | 11/1999 | Foreman et al. |
| 5,976,174 A | 11/1999 | Ruiz |
| 5,976,178 A | 11/1999 | Goldsteen et al. |
| 5,976,192 A | 11/1999 | McIntyre et al. |
| 5,976,650 A | 11/1999 | Campbell et al. |
| 5,979,455 A | 11/1999 | Maginot |
| 5,980,455 A | 11/1999 | Daniel et al. |

(56) References Cited

U.S. PATENT DOCUMENTS

| | | |
|---|---|---|
| 5,980,533 A | 11/1999 | Holman |
| 5,980,548 A | 11/1999 | Evans et al. |
| 5,984,956 A | 11/1999 | Tweden et al. |
| 5,984,957 A | 11/1999 | Laptewicz, Jr. et al. |
| 5,984,959 A | 11/1999 | Robertson et al. |
| 5,984,964 A | 11/1999 | Roberts et al. |
| 5,987,344 A | 11/1999 | West |
| 5,989,276 A | 11/1999 | Houser et al. |
| 5,989,287 A | 11/1999 | Yang et al. |
| 5,993,469 A | 11/1999 | McKenzie et al. |
| 5,993,481 A | 11/1999 | Marcade et al. |
| 5,997,525 A | 12/1999 | March et al. |
| 5,997,557 A | 12/1999 | Barbut et al. |
| 5,997,563 A | 12/1999 | Kretzers |
| 5,997,573 A | 12/1999 | Quijano et al. |
| 5,999,678 A | 12/1999 | Murphy-Chutorian et al. |
| 6,001,123 A | 12/1999 | Lau |
| 6,001,126 A | 12/1999 | Nguyen-Thien-Nhon |
| 6,004,261 A | 12/1999 | Sinofsky et al. |
| 6,004,347 A | 12/1999 | McNamara et al. |
| 6,004,348 A | 12/1999 | Banas et al. |
| 6,007,543 A | 12/1999 | Ellis et al. |
| 6,010,449 A | 1/2000 | Selmon et al. |
| 6,010,522 A | 1/2000 | Barbut et al. |
| 6,010,530 A | 1/2000 | Goicoechea |
| 6,010,531 A | 1/2000 | Donlon et al. |
| 6,012,457 A | 1/2000 | Lesh |
| 6,013,854 A | 1/2000 | Moriuchi |
| 6,015,431 A | 1/2000 | Thornton et al. |
| 6,019,777 A | 2/2000 | Mackenzie |
| 6,019,778 A | 2/2000 | Wilson et al. |
| 6,022,370 A | 2/2000 | Tower |
| 6,026,814 A | 2/2000 | LaFontaine et al. |
| 6,027,476 A | 2/2000 | Sterman et al. |
| 6,027,520 A | 2/2000 | Tsugita et al. |
| 6,027,525 A | 2/2000 | Suh et al. |
| 6,029,671 A | 2/2000 | Stevens et al. |
| 6,029,672 A | 2/2000 | Vanney et al. |
| 6,033,582 A | 3/2000 | Lee et al. |
| 6,035,856 A | 3/2000 | LaFontaine et al. |
| 6,036,677 A | 3/2000 | Javier, Jr. et al. |
| 6,036,697 A | 3/2000 | DiCaprio |
| 6,042,554 A | 3/2000 | Rosenman et al. |
| 6,042,581 A | 3/2000 | Ryan et al. |
| 6,042,589 A | 3/2000 | Marianne |
| 6,042,598 A | 3/2000 | Tsugita et al. |
| 6,042,607 A | 3/2000 | Williamson, IV et al. |
| 6,045,565 A | 4/2000 | Ellis et al. |
| 6,051,014 A | 4/2000 | Jang |
| 6,051,104 A | 4/2000 | Oriaran et al. |
| 6,053,924 A | 4/2000 | Hussein |
| 6,053,942 A | 4/2000 | Eno et al. |
| 6,056,743 A | 5/2000 | Ellis et al. |
| 6,059,809 A | 5/2000 | Amor et al. |
| 6,059,827 A | 5/2000 | Fenton, Jr. |
| 6,066,160 A | 5/2000 | Colvin et al. |
| 6,067,988 A | 5/2000 | Mueller |
| 6,068,638 A | 5/2000 | Makower |
| 6,071,292 A | 6/2000 | Makower et al. |
| 6,074,416 A | 6/2000 | Berg et al. |
| 6,074,417 A | 6/2000 | Peredo |
| 6,074,418 A | 6/2000 | Buchanan et al. |
| 6,076,529 A | 6/2000 | Vanney et al. |
| 6,076,742 A | 6/2000 | Benary |
| 6,077,297 A | 6/2000 | Robinson et al. |
| 6,079,414 A | 6/2000 | Roth |
| 6,080,163 A | 6/2000 | Hussein et al. |
| 6,080,170 A | 6/2000 | Nash et al. |
| 6,083,257 A | 7/2000 | Taylor et al. |
| 6,091,042 A | 7/2000 | Benary |
| 6,092,526 A | 7/2000 | LaFontaine et al. |
| 6,092,529 A | 7/2000 | Cox |
| 6,093,166 A | 7/2000 | Knudson et al. |
| 6,093,177 A | 7/2000 | Javier, Jr. et al. |
| 6,093,185 A | 7/2000 | Ellis et al. |
| 6,093,203 A | 7/2000 | Uflacker |
| 6,093,530 A | 7/2000 | McIlroy et al. |
| 6,096,074 A | 8/2000 | Pedros |
| 6,102,941 A | 8/2000 | Tweden et al. |
| 6,102,944 A | 8/2000 | Huynh et al. |
| 6,106,550 A | 8/2000 | Magovern et al. |
| 6,110,191 A | 8/2000 | Dehdashtian et al. |
| 6,110,198 A | 8/2000 | Fogarty et al. |
| 6,110,201 A | 8/2000 | Quijano et al. |
| 6,113,612 A | 9/2000 | Swanson et al. |
| 6,113,630 A | 9/2000 | Vanney et al. |
| 6,113,823 A | 9/2000 | Eno |
| 6,117,169 A | 9/2000 | Moe |
| 6,120,520 A | 9/2000 | Saadat et al. |
| 6,120,534 A | 9/2000 | Ruiz |
| 6,123,682 A | 9/2000 | Knudson et al. |
| 6,123,723 A | 9/2000 | Konya et al. |
| 6,125,852 A | 10/2000 | Stevens et al. |
| 6,126,649 A | 10/2000 | VanTassel et al. |
| 6,126,654 A | 10/2000 | Giba et al. |
| 6,126,685 A | 10/2000 | Lenker et al. |
| 6,126,686 A | 10/2000 | Badylak et al. |
| 6,132,451 A | 10/2000 | Payne et al. |
| 6,132,473 A | 10/2000 | Williams et al. |
| 6,132,986 A | 10/2000 | Pathak et al. |
| 6,139,510 A | 10/2000 | Palermo |
| 6,139,541 A | 10/2000 | Vanney et al. |
| 6,142,987 A | 11/2000 | Tsugita |
| 6,143,021 A | 11/2000 | Staehle |
| 6,143,987 A | 11/2000 | Makita |
| 6,146,366 A | 11/2000 | Schachar |
| 6,146,415 A | 11/2000 | Fitz |
| 6,146,417 A | 11/2000 | Ischinger |
| 6,152,937 A | 11/2000 | Peterson et al. |
| 6,152,956 A | 11/2000 | Pierce |
| 6,155,264 A | 12/2000 | Ressemann et al. |
| 6,156,031 A | 12/2000 | Aita et al. |
| 6,156,055 A | 12/2000 | Ravenscroft |
| 6,156,531 A | 12/2000 | Pathak et al. |
| 6,157,852 A | 12/2000 | Selmon et al. |
| 6,159,225 A | 12/2000 | Makower |
| 6,159,239 A | 12/2000 | Greenhalgh |
| 6,162,208 A | 12/2000 | Hipps |
| 6,162,245 A | 12/2000 | Jayaraman |
| 6,165,185 A | 12/2000 | Shennib et al. |
| 6,165,188 A | 12/2000 | Saadat et al. |
| 6,165,200 A | 12/2000 | Tsugita et al. |
| 6,165,209 A | 12/2000 | Patterson et al. |
| 6,167,605 B1 | 1/2001 | Morales |
| 6,168,579 B1 | 1/2001 | Tsugita |
| 6,168,614 B1 | 1/2001 | Andersen et al. |
| 6,168,616 B1 | 1/2001 | Brown, III |
| 6,171,251 B1 | 1/2001 | Mueller et al. |
| 6,171,327 B1 | 1/2001 | Daniel et al. |
| 6,171,335 B1 | 1/2001 | Wheatley et al. |
| 6,177,514 B1 | 1/2001 | Pathak et al. |
| 6,179,859 B1 | 1/2001 | Bates et al. |
| 6,182,664 B1 | 2/2001 | Cosgrove |
| 6,182,668 B1 | 2/2001 | Tweden et al. |
| 6,183,481 B1 | 2/2001 | Lee et al. |
| 6,186,972 B1 | 2/2001 | Nelson et al. |
| 6,187,016 B1 | 2/2001 | Hedges et al. |
| 6,190,353 B1 | 2/2001 | Makower et al. |
| 6,190,393 B1 | 2/2001 | Bevier et al. |
| 6,190,405 B1 | 2/2001 | Culombo et al. |
| 6,193,726 B1 | 2/2001 | Vanney |
| 6,193,734 B1 | 2/2001 | Bolduc et al. |
| 6,196,230 B1 | 3/2001 | Hall et al. |
| 6,197,050 B1 | 3/2001 | Eno et al. |
| 6,197,053 B1 | 3/2001 | Cosgrove et al. |
| 6,197,296 B1 | 3/2001 | Davies et al. |
| 6,197,324 B1 | 3/2001 | Crittenden |
| 6,200,311 B1 | 3/2001 | Danek et al. |
| 6,200,336 B1 | 3/2001 | Pavcnik et al. |
| 6,203,550 B1 | 3/2001 | Olson |
| 6,203,556 B1 | 3/2001 | Evans et al. |
| 6,206,888 B1 | 3/2001 | Bicek et al. |
| 6,206,911 B1 | 3/2001 | Milo |
| 6,210,408 B1 | 4/2001 | Chandrasekaran et al. |

(56) References Cited

U.S. PATENT DOCUMENTS

| | | |
|---|---|---|
| 6,210,957 B1 | 4/2001 | Carpentier et al. |
| 6,213,126 B1 | 4/2001 | LaFontaine et al. |
| 6,214,036 B1 | 4/2001 | Letendre et al. |
| 6,214,041 B1 | 4/2001 | Tweden et al. |
| 6,214,054 B1 | 4/2001 | Cunanan et al. |
| 6,214,055 B1 | 4/2001 | Simionescu et al. |
| 6,217,527 B1 | 4/2001 | Selmon et al. |
| 6,217,549 B1 | 4/2001 | Selmon et al. |
| 6,217,575 B1 | 4/2001 | DeVore et al. |
| 6,217,609 B1 | 4/2001 | Haverkost |
| 6,218,662 B1 | 4/2001 | Tchakarov et al. |
| 6,221,006 B1 | 4/2001 | Dubrul et al. |
| 6,221,049 B1 | 4/2001 | Selmon et al. |
| 6,221,091 B1 | 4/2001 | Khosravi |
| 6,221,096 B1 | 4/2001 | Aiba et al. |
| 6,221,100 B1 | 4/2001 | Strecker |
| 6,223,752 B1 | 5/2001 | Vanney et al. |
| 6,224,584 B1 | 5/2001 | March et al. |
| 6,231,544 B1 | 5/2001 | Tsugita et al. |
| 6,231,546 B1 | 5/2001 | Milo et al. |
| 6,231,551 B1 | 5/2001 | Barbut |
| 6,231,587 B1 | 5/2001 | Makower |
| 6,231,602 B1 | 5/2001 | Carpentier et al. |
| 6,235,000 B1 | 5/2001 | Milo et al. |
| 6,237,607 B1 | 5/2001 | Vanney et al. |
| 6,238,406 B1 | 5/2001 | Ellis et al. |
| 6,241,667 B1 | 6/2001 | Vetter et al. |
| 6,241,738 B1 | 6/2001 | Dereume |
| 6,241,741 B1 | 6/2001 | Duhaylongsod et al. |
| 6,241,757 B1 | 6/2001 | An et al. |
| 6,245,102 B1 | 6/2001 | Jayaraman |
| 6,245,103 B1 | 6/2001 | Stinson |
| 6,245,105 B1 | 6/2001 | Nguyen et al. |
| 6,248,112 B1 | 6/2001 | Gambale et al. |
| 6,248,116 B1 | 6/2001 | Chevillon et al. |
| 6,250,305 B1 | 6/2001 | Tweden |
| 6,251,079 B1 | 6/2001 | Gambale et al. |
| 6,251,104 B1 | 6/2001 | Kesten et al. |
| 6,251,116 B1 | 6/2001 | Shennib et al. |
| 6,251,135 B1 | 6/2001 | Stinson et al. |
| 6,251,418 B1 | 6/2001 | Ahern et al. |
| 6,253,768 B1 | 7/2001 | Wilk |
| 6,253,769 B1 | 7/2001 | LaFontaine et al. |
| 6,254,564 B1 | 7/2001 | Wilk et al. |
| 6,254,635 B1 | 7/2001 | Schroeder et al. |
| 6,254,636 B1 | 7/2001 | Peredo |
| 6,257,634 B1 | 7/2001 | Wei |
| 6,258,052 B1 | 7/2001 | Milo |
| 6,258,087 B1 | 7/2001 | Edwards et al. |
| 6,258,114 B1 | 7/2001 | Konya et al. |
| 6,258,115 B1 | 7/2001 | Dubrul |
| 6,258,119 B1 | 7/2001 | Hussein et al. |
| 6,258,120 B1 | 7/2001 | McKenzie et al. |
| 6,258,129 B1 | 7/2001 | Dybdal et al. |
| 6,258,150 B1 | 7/2001 | Mackellar |
| 6,261,304 B1 | 7/2001 | Hall et al. |
| 6,267,783 B1 | 7/2001 | Letendre et al. |
| 6,269,819 B1 | 8/2001 | Oz et al. |
| 6,270,513 B1 | 8/2001 | Tsugita et al. |
| 6,270,521 B1 | 8/2001 | Fischell et al. |
| 6,270,526 B1 | 8/2001 | Cox |
| 6,273,876 B1 | 8/2001 | Klima et al. |
| 6,273,895 B1 | 8/2001 | Pinchuk et al. |
| 6,276,661 B1 | 8/2001 | Laird |
| 6,277,555 B1 | 8/2001 | Duran et al. |
| 6,283,127 B1 | 9/2001 | Sterman et al. |
| 6,283,951 B1 | 9/2001 | Flaherty et al. |
| 6,283,983 B1 | 9/2001 | Makower et al. |
| 6,283,995 B1 | 9/2001 | Moe et al. |
| 6,285,903 B1 | 9/2001 | Rosenthal et al. |
| 6,287,317 B1 | 9/2001 | Makower et al. |
| 6,287,334 B1 | 9/2001 | Moll et al. |
| 6,287,338 B1 | 9/2001 | Sarnowski et al. |
| 6,287,339 B1 | 9/2001 | Vazquez et al. |
| 6,290,709 B1 | 9/2001 | Ellis et al. |
| 6,290,728 B1 | 9/2001 | Phelps et al. |
| 6,296,662 B1 | 10/2001 | Caffey |
| 6,299,637 B1 | 10/2001 | Shaolian et al. |
| 6,302,875 B1 | 10/2001 | Makower et al. |
| 6,302,892 B1 | 10/2001 | Wilk |
| 6,302,906 B1 | 10/2001 | Goicoechea et al. |
| 6,306,164 B1 | 10/2001 | Kujawski |
| 6,309,382 B1 | 10/2001 | Garrison et al. |
| 6,309,417 B1 | 10/2001 | Spence et al. |
| 6,311,693 B1 | 11/2001 | Sterman et al. |
| 6,312,465 B1 | 11/2001 | Griffin et al. |
| 6,319,281 B1 | 11/2001 | Patel |
| 6,322,548 B1 | 11/2001 | Payne et al. |
| 6,322,593 B1 | 11/2001 | Pathak et al. |
| 6,325,067 B1 | 12/2001 | Sterman et al. |
| 6,327,772 B1 | 12/2001 | Zadno-Azizi et al. |
| 6,330,884 B1 | 12/2001 | Kim |
| 6,331,189 B1 | 12/2001 | Wolinsky et al. |
| 6,334,873 B1 | 1/2002 | Lane et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,338,740 B1 | 1/2002 | Carpentier |
| 6,342,070 B1 | 1/2002 | Nguyen-Thien-Nhon |
| 6,344,044 B1 | 2/2002 | Fulkerson et al. |
| 6,346,074 B1 | 2/2002 | Roth |
| 6,346,116 B1 | 2/2002 | Brooks et al. |
| 6,348,063 B1 | 2/2002 | Yassour et al. |
| 6,350,248 B1 | 2/2002 | Knudson et al. |
| 6,350,277 B1 | 2/2002 | Kocur |
| 6,350,278 B1 | 2/2002 | Lenker et al. |
| 6,352,547 B1 | 3/2002 | Brown et al. |
| 6,352,554 B2 | 3/2002 | De Paulis |
| 6,352,708 B1 | 3/2002 | Duran et al. |
| 6,357,104 B1 | 3/2002 | Myers |
| 6,358,277 B1 | 3/2002 | Duran |
| 6,361,519 B1 | 3/2002 | Knudson et al. |
| 6,361,545 B1 | 3/2002 | Macoviak et al. |
| 6,363,938 B2 | 4/2002 | Saadat et al. |
| 6,363,939 B1 | 4/2002 | Wilk |
| 6,364,895 B1 | 4/2002 | Greenhalgh |
| 6,368,338 B1 | 4/2002 | Konya et al. |
| 6,371,970 B1 | 4/2002 | Khosravi et al. |
| 6,371,983 B1 | 4/2002 | Lane |
| 6,375,615 B1 | 4/2002 | Flaherty et al. |
| 6,378,221 B1 | 4/2002 | Ekholm, Jr. et al. |
| 6,379,319 B1 | 4/2002 | Garibotto et al. |
| 6,379,365 B1 | 4/2002 | Diaz |
| 6,379,372 B1 | 4/2002 | Dehdashtian et al. |
| 6,379,383 B1 | 4/2002 | Palmaz et al. |
| 6,379,740 B1 | 4/2002 | Rinaldi et al. |
| 6,380,457 B1 | 4/2002 | Yurek et al. |
| 6,383,193 B1 | 5/2002 | Cathcart et al. |
| 6,387,119 B2 | 5/2002 | Wolf et al. |
| 6,387,122 B1 | 5/2002 | Cragg |
| 6,390,098 B1 | 5/2002 | LaFontaine et al. |
| 6,391,051 B2 | 5/2002 | Sullivan, III et al. |
| 6,391,538 B1 | 5/2002 | Vyavahare et al. |
| 6,395,208 B1 | 5/2002 | Herweck et al. |
| 6,398,807 B1 | 6/2002 | Chouinard et al. |
| 6,401,720 B1 | 6/2002 | Stevens et al. |
| 6,402,736 B1 | 6/2002 | Brown et al. |
| 6,402,740 B1 | 6/2002 | Ellis et al. |
| 6,406,488 B1 | 6/2002 | Tweden et al. |
| 6,406,491 B1 | 6/2002 | Vanney |
| 6,406,493 B1 | 6/2002 | Tu et al. |
| 6,409,697 B2 | 6/2002 | Eno et al. |
| 6,409,750 B1 | 6/2002 | Hyodoh et al. |
| 6,409,751 B1 | 6/2002 | Hall et al. |
| 6,409,755 B1 | 6/2002 | Vrba |
| 6,409,759 B1 | 6/2002 | Peredo |
| 6,413,275 B1 | 7/2002 | Nguyen et al. |
| 6,416,490 B1 | 7/2002 | Ellis et al. |
| 6,416,510 B1 | 7/2002 | Altman et al. |
| 6,423,089 B1 | 7/2002 | Gingras et al. |
| 6,425,916 B1 | 7/2002 | Garrison et al. |
| 6,432,119 B1 | 8/2002 | Saadat |
| 6,432,126 B1 | 8/2002 | Gambale et al. |
| 6,432,127 B1 | 8/2002 | Kim et al. |

(56) References Cited

U.S. PATENT DOCUMENTS

| | | |
|---|---|---|
| 6,432,132 B1 | 8/2002 | Cottone et al. |
| 6,440,164 B1 | 8/2002 | DiMatteo et al. |
| 6,443,158 B1 | 9/2002 | LaFontaine et al. |
| 6,447,522 B2 | 9/2002 | Gambale et al. |
| 6,447,539 B1 | 9/2002 | Nelson et al. |
| 6,451,025 B1 | 9/2002 | Jervis |
| 6,451,054 B1 | 9/2002 | Stevens |
| 6,454,760 B2 | 9/2002 | Vanney |
| 6,454,794 B1 | 9/2002 | Knudson et al. |
| 6,454,799 B1 | 9/2002 | Schreck |
| 6,458,092 B1 | 10/2002 | Gambale et al. |
| 6,458,140 B2 | 10/2002 | Akin et al. |
| 6,458,153 B1 | 10/2002 | Bailey et al. |
| 6,458,323 B1 | 10/2002 | Boekstegers |
| 6,461,382 B1 | 10/2002 | Cao |
| 6,464,709 B1 | 10/2002 | Shennib et al. |
| 6,468,303 B1 | 10/2002 | Amplatz et al. |
| 6,468,660 B2 | 10/2002 | Ogle et al. |
| 6,471,723 B1 | 10/2002 | Ashworth et al. |
| 6,475,169 B2 | 11/2002 | Ferrera |
| 6,475,226 B1 | 11/2002 | Belef et al. |
| 6,475,239 B1 | 11/2002 | Campbell et al. |
| 6,475,244 B2 | 11/2002 | Herweck et al. |
| 6,478,819 B2 | 11/2002 | Moe |
| 6,479,079 B1 | 11/2002 | Pathak et al. |
| 6,482,220 B1 | 11/2002 | Mueller |
| 6,482,228 B1 | 11/2002 | Norred |
| 6,485,501 B1 | 11/2002 | Green |
| 6,485,502 B2 | 11/2002 | Don Michael et al. |
| 6,485,513 B1 | 11/2002 | Fan |
| 6,485,524 B2 | 11/2002 | Strecker |
| 6,487,581 B1 | 11/2002 | Spence et al. |
| 6,488,704 B1 | 12/2002 | Connelly et al. |
| 6,491,689 B1 | 12/2002 | Ellis et al. |
| 6,491,707 B2 | 12/2002 | Makower et al. |
| 6,494,211 B1 | 12/2002 | Boyd et al. |
| 6,494,897 B2 | 12/2002 | Sterman et al. |
| 6,494,909 B2 | 12/2002 | Greenhalgh |
| 6,503,272 B2 | 1/2003 | Duerig et al. |
| 6,508,496 B1 | 1/2003 | Huang |
| 6,508,803 B1 | 1/2003 | Horikawa et al. |
| 6,508,825 B1 | 1/2003 | Selmon et al. |
| 6,508,833 B2 | 1/2003 | Pavcnik et al. |
| 6,509,145 B1 | 1/2003 | Torrianni |
| 6,511,458 B2 | 1/2003 | Milo et al. |
| 6,511,491 B2 | 1/2003 | Grudem et al. |
| 6,514,217 B1 | 2/2003 | Selmon et al. |
| 6,514,271 B2 | 2/2003 | Evans et al. |
| 6,517,527 B2 | 2/2003 | Gambale et al. |
| 6,517,558 B2 | 2/2003 | Gittings et al. |
| 6,517,573 B1 | 2/2003 | Pollock et al. |
| 6,521,179 B1 | 2/2003 | Girardot et al. |
| 6,524,323 B1 | 2/2003 | Nash et al. |
| 6,524,335 B1 | 2/2003 | Hartley et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,533,807 B2 | 3/2003 | Wolinsky et al. |
| 6,537,297 B2 | 3/2003 | Tsugita et al. |
| 6,537,310 B1 | 3/2003 | Palmaz et al. |
| 6,540,768 B1 | 4/2003 | Diaz et al. |
| 6,540,782 B1 | 4/2003 | Snyders |
| 6,544,230 B1 | 4/2003 | Flaherty et al. |
| 6,547,827 B2 | 4/2003 | Carpentier |
| 6,551,303 B1 | 4/2003 | Van Tassel et al. |
| 6,558,318 B1 | 5/2003 | Daniel et al. |
| 6,558,417 B2 | 5/2003 | Peredo |
| 6,558,418 B2 | 5/2003 | Carpentier et al. |
| 6,558,429 B2 | 5/2003 | Taylor |
| 6,559,132 B1 | 5/2003 | Holmer |
| 6,561,998 B1 | 5/2003 | Roth et al. |
| 6,562,031 B2 | 5/2003 | Chandrasekaran et al. |
| 6,562,058 B2 | 5/2003 | Seguin et al. |
| 6,562,063 B1 | 5/2003 | Euteneuer et al. |
| 6,562,069 B2 | 5/2003 | Cai et al. |
| 6,564,805 B2 | 5/2003 | Garrison et al. |
| 6,565,528 B1 | 5/2003 | Mueller |
| 6,565,594 B1 | 5/2003 | Herweck et al. |
| 6,569,145 B1 | 5/2003 | Shmulewitz et al. |
| 6,569,147 B1 | 5/2003 | Evans et al. |
| 6,569,196 B1 | 5/2003 | Vesely |
| 6,572,642 B2 | 6/2003 | Rinaldi et al. |
| 6,572,643 B1 | 6/2003 | Gharibadeh |
| 6,572,652 B2 | 6/2003 | Shaknovich |
| 6,575,168 B2 | 6/2003 | LaFontaine et al. |
| 6,579,311 B1 | 6/2003 | Makower |
| 6,582,444 B2 | 6/2003 | Wilk |
| 6,582,460 B1 | 6/2003 | Cryer |
| 6,582,462 B1 | 6/2003 | Andersen et al. |
| 6,585,756 B1 | 7/2003 | Strecker |
| 6,585,758 B1 | 7/2003 | Chouinard et al. |
| 6,585,766 B1 | 7/2003 | Huynh et al. |
| 6,589,279 B1 | 7/2003 | Anderson et al. |
| 6,592,546 B1 | 7/2003 | Barbut et al. |
| 6,592,614 B2 | 7/2003 | Lenker et al. |
| 6,599,304 B1 | 7/2003 | Selmon et al. |
| 6,600,803 B2 | 7/2003 | Bruder et al. |
| 6,605,053 B1 | 8/2003 | Kamm et al. |
| 6,605,112 B1 | 8/2003 | Moll et al. |
| 6,605,113 B2 | 8/2003 | Wilk |
| 6,608,040 B1 | 8/2003 | Lin et al. |
| 6,610,077 B1 | 8/2003 | Hancock et al. |
| 6,610,085 B1 | 8/2003 | Lazarus |
| 6,610,100 B2 | 8/2003 | Phelps et al. |
| 6,613,069 B2 | 9/2003 | Boyd et al. |
| 6,613,077 B2 | 9/2003 | Gilligan et al. |
| 6,613,079 B1 | 9/2003 | Wolinsky et al. |
| 6,613,081 B2 | 9/2003 | Kim et al. |
| 6,613,086 B1 | 9/2003 | Moe et al. |
| 6,616,675 B1 | 9/2003 | Evard et al. |
| 6,616,682 B2 | 9/2003 | Joergensen et al. |
| 6,622,604 B1 | 9/2003 | Chouinard et al. |
| 6,623,491 B2 | 9/2003 | Thompson |
| 6,623,518 B2 | 9/2003 | Thompson et al. |
| 6,623,521 B2 | 9/2003 | Steinke et al. |
| 6,626,938 B1 | 9/2003 | Butaric et al. |
| 6,626,939 B1 | 9/2003 | Burnside et al. |
| 6,632,241 B1 | 10/2003 | Hancock et al. |
| 6,632,243 B1 | 10/2003 | Zadno-Azizi et al. |
| 6,632,470 B2 | 10/2003 | Morra et al. |
| 6,635,068 B1 | 10/2003 | Dubrul et al. |
| 6,635,079 B2 | 10/2003 | Unsworth et al. |
| 6,635,080 B1 | 10/2003 | Lauterjung et al. |
| 6,635,085 B1 | 10/2003 | Caffey et al. |
| 6,638,237 B1 | 10/2003 | Guiles et al. |
| 6,638,247 B1 | 10/2003 | Selmon et al. |
| 6,638,293 B1 | 10/2003 | Makower et al. |
| 6,641,610 B2 | 11/2003 | Wolf et al. |
| 6,651,670 B2 | 11/2003 | Rapacki et al. |
| 6,651,672 B2 | 11/2003 | Roth |
| 6,652,540 B1 | 11/2003 | Cole et al. |
| 6,652,546 B1 | 11/2003 | Nash et al. |
| 6,652,555 B1 | 11/2003 | VanTassel et al. |
| 6,652,571 B1 | 11/2003 | White et al. |
| 6,652,578 B2 | 11/2003 | Bailey et al. |
| 6,655,386 B1 | 12/2003 | Makower et al. |
| 6,656,213 B2 | 12/2003 | Solem |
| 6,660,003 B1 | 12/2003 | DeVore et al. |
| 6,660,024 B1 | 12/2003 | Flaherty et al. |
| 6,663,588 B2 | 12/2003 | DuBois et al. |
| 6,663,663 B2 | 12/2003 | Kim et al. |
| 6,663,667 B2 | 12/2003 | Dehdashtian et al. |
| 6,666,863 B2 | 12/2003 | Wentzel et al. |
| 6,669,709 B1 | 12/2003 | Cohn et al. |
| 6,669,724 B2 | 12/2003 | Park et al. |
| 6,673,089 B1 | 1/2004 | Yassour et al. |
| 6,673,101 B1 | 1/2004 | Fitzgerald et al. |
| 6,673,106 B2 | 1/2004 | Mitelberg et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,693 B1 | 1/2004 | Belding et al. |
| 6,676,698 B2 | 1/2004 | McGuckin, Jr. et al. |
| 6,679,268 B2 | 1/2004 | Stevens et al. |

(56) References Cited

U.S. PATENT DOCUMENTS

| | | |
|---|---|---|
| 6,682,543 B2 | 1/2004 | Barbut et al. |
| 6,682,558 B2 | 1/2004 | Tu et al. |
| 6,682,559 B2 | 1/2004 | Myers et al. |
| 6,685,648 B2 | 2/2004 | Flaherty et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,694,983 B2 | 2/2004 | Wolf et al. |
| 6,695,864 B2 | 2/2004 | Macoviak et al. |
| 6,695,865 B2 | 2/2004 | Boyle et al. |
| 6,695,875 B2 | 2/2004 | Stelter et al. |
| 6,695,878 B2 | 2/2004 | McGuckin, Jr. et al. |
| 6,699,274 B2 | 3/2004 | Stinson |
| 6,701,932 B2 | 3/2004 | Knudson et al. |
| 6,702,851 B1 | 3/2004 | Chinn et al. |
| 6,709,425 B2 | 3/2004 | Gambale et al. |
| 6,709,444 B1 | 3/2004 | Makower |
| 6,712,842 B1 | 3/2004 | Gifford, III et al. |
| 6,712,843 B2 | 3/2004 | Elliott |
| 6,714,842 B1 | 3/2004 | Ito |
| 6,719,770 B2 | 4/2004 | Laufer et al. |
| 6,719,787 B2 | 4/2004 | Cox |
| 6,719,788 B2 | 4/2004 | Cox |
| 6,719,789 B2 | 4/2004 | Cox |
| 6,723,116 B2 | 4/2004 | Taheri |
| 6,723,122 B2 | 4/2004 | Yang et al. |
| 6,726,677 B1 | 4/2004 | Flaherty et al. |
| 6,729,356 B1 | 5/2004 | Baker et al. |
| 6,730,118 B2 | 5/2004 | Spenser et al. |
| 6,730,121 B2 | 5/2004 | Ortiz et al. |
| 6,730,377 B2 | 5/2004 | Wang |
| 6,733,513 B2 | 5/2004 | Boyle et al. |
| 6,733,525 B2 | 5/2004 | Yang et al. |
| 6,736,827 B1 | 5/2004 | McAndrew et al. |
| 6,736,839 B2 | 5/2004 | Cummings |
| 6,736,845 B2 | 5/2004 | Marquez et al. |
| 6,736,846 B2 | 5/2004 | Cox |
| 6,743,252 B1 | 6/2004 | Bates et al. |
| 6,746,464 B1 | 6/2004 | Makower |
| 6,752,828 B2 | 6/2004 | Thornton |
| 6,755,854 B2 | 6/2004 | Gillick et al. |
| 6,755,855 B2 | 6/2004 | Yurek et al. |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,767,362 B2 | 7/2004 | Schreck |
| 6,769,434 B2 | 8/2004 | Liddicoat et al. |
| 6,773,454 B2 | 8/2004 | Wholey et al. |
| 6,773,455 B2 | 8/2004 | Allen et al. |
| 6,773,456 B1 | 8/2004 | Gordon et al. |
| 6,774,278 B1 | 8/2004 | Ragheb et al. |
| 6,776,791 B1 | 8/2004 | Stallings et al. |
| 6,786,925 B1 | 9/2004 | Schoon et al. |
| 6,786,929 B2 | 9/2004 | Gambale et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,797,000 B2 | 9/2004 | Simpson et al. |
| 6,797,002 B2 | 9/2004 | Spence et al. |
| 6,802,319 B2 | 10/2004 | Stevens et al. |
| 6,802,858 B2 | 10/2004 | Gambale et al. |
| 6,805,711 B2 | 10/2004 | Quijano et al. |
| 6,808,498 B2 | 10/2004 | Laroya et al. |
| 6,808,504 B2 | 10/2004 | Schorgl et al. |
| 6,808,529 B2 | 10/2004 | Fulkerson |
| 6,814,746 B2 | 11/2004 | Thompson et al. |
| 6,814,754 B2 | 11/2004 | Greenhalgh |
| 6,820,676 B2 | 11/2004 | Palmaz et al. |
| 6,821,211 B2 | 11/2004 | Otten et al. |
| 6,821,297 B2 | 11/2004 | Snyders |
| 6,824,041 B2 | 11/2004 | Grieder et al. |
| 6,824,970 B2 | 11/2004 | Vyavahare et al. |
| 6,830,568 B1 | 12/2004 | Kesten et al. |
| 6,830,575 B2 | 12/2004 | Stenzel et al. |
| 6,830,584 B1 | 12/2004 | Seguin |
| 6,830,585 B1 | 12/2004 | Artof et al. |
| 6,830,586 B2 | 12/2004 | Quijano et al. |
| 6,837,901 B2 | 1/2005 | Rabkin et al. |
| 6,837,902 B2 | 1/2005 | Nguyen et al. |
| 6,840,957 B2 | 1/2005 | DiMatteo et al. |
| 6,843,802 B1 | 1/2005 | Villalobos et al. |
| 6,846,325 B2 | 1/2005 | Liddicoat |
| 6,849,084 B2 | 2/2005 | Rabkin et al. |
| 6,849,085 B2 | 2/2005 | Marton |
| 6,854,467 B2 | 2/2005 | Boekstegers |
| 6,860,898 B2 | 3/2005 | Stack et al. |
| 6,861,211 B2 | 3/2005 | Levy et al. |
| 6,863,668 B2 | 3/2005 | Gillespie et al. |
| 6,863,684 B2 | 3/2005 | Kim et al. |
| 6,863,688 B2 | 3/2005 | Ralph et al. |
| 6,866,650 B2 | 3/2005 | Stevens et al. |
| 6,866,669 B2 | 3/2005 | Buzzard et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,199 B2 | 4/2005 | Wilk et al. |
| 6,881,220 B2 | 4/2005 | Edwin et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,890,340 B2 | 5/2005 | Duane |
| 6,893,459 B1 | 5/2005 | Macoviak |
| 6,893,460 B2 | 5/2005 | Spenser et al. |
| 6,896,690 B1 | 5/2005 | Lambrecht et al. |
| 6,899,704 B2 | 5/2005 | Sterman et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,040 B2 | 6/2005 | Johnson et al. |
| 6,911,043 B2 | 6/2005 | Myers et al. |
| 6,913,021 B2 | 7/2005 | Knudson et al. |
| 6,913,600 B2 | 7/2005 | Valley et al. |
| 6,916,304 B2 | 7/2005 | Eno et al. |
| 6,920,674 B2 | 7/2005 | Thornton |
| 6,920,732 B2 | 7/2005 | Mårtensson |
| 6,926,690 B2 | 8/2005 | Renati |
| 6,926,732 B2 | 8/2005 | Derus et al. |
| 6,929,009 B2 | 8/2005 | Makower et al. |
| 6,929,011 B2 | 8/2005 | Knudson et al. |
| 6,929,653 B2 | 8/2005 | Strecter |
| 6,936,058 B2 | 8/2005 | Forde et al. |
| 6,936,066 B2 | 8/2005 | Palmaz et al. |
| 6,936,067 B2 | 8/2005 | Buchanan |
| 6,939,352 B2 | 9/2005 | Buzzard et al. |
| 6,939,359 B2 | 9/2005 | Tu et al. |
| 6,939,365 B1 | 9/2005 | Fogarty et al. |
| 6,939,370 B2 | 9/2005 | Hartley et al. |
| 6,942,682 B2 | 9/2005 | Vrba et al. |
| 6,945,949 B2 | 9/2005 | Wilk |
| 6,945,997 B2 | 9/2005 | Huynh et al. |
| 6,949,080 B2 | 9/2005 | Wolf et al. |
| 6,949,118 B2 | 9/2005 | Kohler et al. |
| 6,951,571 B1 | 10/2005 | Srivastava |
| 6,953,332 B1 | 10/2005 | Kurk et al. |
| 6,953,481 B2 | 10/2005 | Phelps et al. |
| 6,955,175 B2 | 10/2005 | Stevens et al. |
| 6,955,681 B2 | 10/2005 | Evans et al. |
| 6,964,652 B2 | 11/2005 | Guiles et al. |
| 6,964,673 B2 | 11/2005 | Tsugita et al. |
| 6,964,676 B1 | 11/2005 | Gerberding et al. |
| 6,969,395 B2 | 11/2005 | Eskuri |
| 6,972,025 B2 | 12/2005 | Wasdyke |
| 6,972,029 B2 | 12/2005 | Mayrhofer et al. |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,976,990 B2 | 12/2005 | Mowry |
| 6,979,350 B2 | 12/2005 | Moll et al. |
| 6,984,242 B2 | 1/2006 | Campbell et al. |
| 6,984,244 B2 | 1/2006 | Perez et al. |

(56) References Cited

U.S. PATENT DOCUMENTS

| | | |
|---|---|---|
| 6,986,742 B2 | 1/2006 | Hart et al. |
| 6,986,784 B1 | 1/2006 | Weiser et al. |
| 6,988,949 B2 | 1/2006 | Wang |
| 6,989,027 B2 | 1/2006 | Allen et al. |
| 6,989,028 B2 | 1/2006 | Lashinski et al. |
| 6,991,649 B2 | 1/2006 | Sievers |
| 7,001,425 B2 | 2/2006 | McCullagh et al. |
| 7,004,176 B2 | 2/2006 | Lau |
| 7,008,397 B2 | 3/2006 | Tweden et al. |
| 7,011,095 B2 | 3/2006 | Wolf et al. |
| 7,011,681 B2 | 3/2006 | Vesely |
| 7,014,655 B2 | 3/2006 | Barbarash et al. |
| 7,018,401 B1 | 3/2006 | Hyodoh et al. |
| 7,018,406 B2 | 3/2006 | Seguin et al. |
| 7,018,408 B2 | 3/2006 | Bailey et al. |
| 7,022,134 B1 | 4/2006 | Quijano et al. |
| 7,025,773 B2 | 4/2006 | Gittings et al. |
| 7,025,780 B2 | 4/2006 | Gabbay |
| 7,025,791 B2 | 4/2006 | Levine et al. |
| 7,028,692 B2 | 4/2006 | Sterman et al. |
| 7,037,331 B2 | 5/2006 | Mitelberg et al. |
| 7,037,333 B2 | 5/2006 | Myers et al. |
| 7,041,128 B2 | 5/2006 | McGuckin, Jr. et al. |
| 7,041,132 B2 | 5/2006 | Quijano et al. |
| 7,044,966 B2 | 5/2006 | Svanidze et al. |
| 7,048,014 B2 | 5/2006 | Hyodoh et al. |
| 7,048,757 B2 | 5/2006 | Shaknovich |
| 7,050,276 B2 | 5/2006 | Nishiyama |
| 7,074,236 B2 | 7/2006 | Rabkin et al. |
| 7,078,163 B2 | 7/2006 | Torrianni |
| 7,081,132 B2 | 7/2006 | Cook et al. |
| 7,097,658 B2 | 8/2006 | Oktay |
| 7,097,659 B2 | 8/2006 | Woolfson et al. |
| 7,101,396 B2 | 9/2006 | Artof et al. |
| 7,105,016 B2 | 9/2006 | Shiu et al. |
| 7,108,715 B2 | 9/2006 | Lawrence-Brown et al. |
| 7,115,141 B2 | 10/2006 | Menz et al. |
| 7,118,585 B2 | 10/2006 | Addis |
| 7,122,020 B2 | 10/2006 | Mogul |
| 7,125,418 B2 | 10/2006 | Duran et al. |
| 7,128,759 B2 | 10/2006 | Osborne et al. |
| 7,137,184 B2 | 11/2006 | Schreck |
| 7,141,063 B2 | 11/2006 | White et al. |
| 7,141,064 B2 | 11/2006 | Scott et al. |
| 7,143,312 B1 | 11/2006 | Wang et al. |
| 7,147,662 B1 | 12/2006 | Pollock et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,163,556 B2 | 1/2007 | Xie et al. |
| 7,166,097 B2 | 1/2007 | Barbut |
| 7,175,652 B2 | 2/2007 | Cook et al. |
| 7,175,653 B2 | 2/2007 | Gaber |
| 7,175,654 B2 | 2/2007 | Bonsignore et al. |
| 7,175,656 B2 | 2/2007 | Khairkhahan |
| 7,179,290 B2 | 2/2007 | Cao |
| 7,186,265 B2 | 3/2007 | Sharkawy et al. |
| 7,189,258 B2 | 3/2007 | Johnson et al. |
| 7,189,259 B2 | 3/2007 | Simionescu et al. |
| 7,191,018 B2 | 3/2007 | Gielen et al. |
| 7,191,406 B1 | 3/2007 | Barber et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,214,344 B2 | 5/2007 | Carpentier et al. |
| 7,217,287 B2 | 5/2007 | Wilson et al. |
| 7,235,092 B2 | 6/2007 | Banas et al. |
| 7,235,093 B2 | 6/2007 | Gregorich |
| 7,238,200 B2 | 7/2007 | Lee et al. |
| 7,241,257 B1 | 7/2007 | Ainsworth et al. |
| 7,252,682 B2 | 8/2007 | Seguin |
| 7,258,696 B2 | 8/2007 | Rabkin et al. |
| 7,258,891 B2 | 8/2007 | Pacetti et al. |
| 7,261,732 B2 | 8/2007 | Justino |
| 7,264,632 B2 | 9/2007 | Wright et al. |
| 7,267,686 B2 | 9/2007 | DiMatteo et al. |
| 7,276,078 B2 | 10/2007 | Spenser et al. |
| 7,276,084 B2 | 10/2007 | Yang et al. |
| 7,285,130 B2 | 10/2007 | Austin |
| 7,297,150 B2 | 11/2007 | Cartledge et al. |
| 7,300,457 B2 | 11/2007 | Palmaz |
| 7,300,463 B2 | 11/2007 | Liddicoat |
| 7,311,730 B2 | 12/2007 | Gabbay |
| 7,314,449 B2 | 1/2008 | Pfeiffer et al. |
| 7,314,485 B2 | 1/2008 | Mathis |
| 7,314,880 B2 | 1/2008 | Chang et al. |
| 7,316,706 B2 | 1/2008 | Bloom et al. |
| 7,316,712 B2 | 1/2008 | Peredo |
| 7,317,005 B2 | 1/2008 | Hoekstra et al. |
| 7,317,942 B2 | 1/2008 | Brown |
| 7,317,950 B2 | 1/2008 | Lee |
| 7,318,278 B2 | 1/2008 | Zhang et al. |
| 7,318,998 B2 | 1/2008 | Goldstein et al. |
| 7,319,096 B2 | 1/2008 | Malm et al. |
| 7,320,692 B1 | 1/2008 | Bender et al. |
| 7,320,704 B2 | 1/2008 | Lashinski et al. |
| 7,320,705 B2 | 1/2008 | Quintessenza |
| 7,320,706 B2 | 1/2008 | Al-Najjar |
| 7,322,932 B2 | 1/2008 | Xie et al. |
| 7,323,006 B2 | 1/2008 | Andreas et al. |
| 7,323,066 B1 | 1/2008 | Budron |
| 7,326,174 B2 | 2/2008 | Cox et al. |
| 7,326,219 B2 | 2/2008 | Mowry et al. |
| 7,326,236 B2 | 2/2008 | Andreas et al. |
| 7,327,862 B2 | 2/2008 | Murphy et al. |
| 7,329,278 B2 | 2/2008 | Seguin et al. |
| 7,329,279 B2 | 2/2008 | Haug et al. |
| 7,329,280 B2 | 2/2008 | Bolling et al. |
| 7,329,777 B2 | 2/2008 | Harter et al. |
| 7,331,991 B2 | 2/2008 | Kheradvar et al. |
| 7,331,993 B2 | 2/2008 | White |
| 7,333,643 B2 | 2/2008 | Murphy et al. |
| 7,335,158 B2 | 2/2008 | Taylor |
| 7,335,213 B1 | 2/2008 | Hyde et al. |
| 7,335,218 B2 | 2/2008 | Wilson et al. |
| 7,335,490 B2 | 2/2008 | Van Gilst et al. |
| 7,338,484 B2 | 3/2008 | Schoon et al. |
| 7,338,520 B2 | 3/2008 | Bailey et al. |
| 7,361,189 B2 | 4/2008 | Case et al. |
| 7,361,190 B2 | 4/2008 | Shaoulian et al. |
| 7,364,588 B2 | 4/2008 | Mathis et al. |
| 7,371,258 B2 | 5/2008 | Woo et al. |
| 7,374,560 B2 | 5/2008 | Ressemann et al. |
| 7,374,571 B2 | 5/2008 | Pease et al. |
| 7,377,895 B2 | 5/2008 | Spence et al. |
| 7,377,938 B2 | 5/2008 | Sarac et al. |
| 7,377,940 B2 | 5/2008 | Ryan et al. |
| 7,381,210 B2 | 6/2008 | Zarbatany et al. |
| 7,381,216 B2 | 6/2008 | Buzzard et al. |
| 7,381,218 B2 | 6/2008 | Schreck |
| 7,381,219 B2 | 6/2008 | Salahieh et al. |
| 7,381,220 B2 | 6/2008 | Macoviak et al. |
| 7,384,411 B1 | 6/2008 | Condado |
| 7,387,640 B2 | 6/2008 | Cummings |
| 7,389,874 B2 | 6/2008 | Quest et al. |
| 7,390,325 B2 | 6/2008 | Wang et al. |
| 7,393,358 B2 | 7/2008 | Malewicz |
| 7,393,360 B2 | 7/2008 | Spenser et al. |
| 7,396,364 B2 | 7/2008 | Moaddeb et al. |
| 7,399,315 B2 | 7/2008 | Lobbi |
| 7,402,171 B2 | 7/2008 | Osborne et al. |
| 7,404,792 B2 | 7/2008 | Spence et al. |
| 7,404,793 B2 | 7/2008 | Lau et al. |
| 7,405,259 B2 | 7/2008 | Frye et al. |
| 7,410,499 B2 | 8/2008 | Bicer |
| 7,412,274 B2 | 8/2008 | Mejia |
| 7,412,290 B2 | 8/2008 | Janke et al. |
| 7,415,861 B2 | 8/2008 | Sokel |
| 7,416,530 B2 | 8/2008 | Turner et al. |
| 7,422,603 B2 | 9/2008 | Lane |
| 7,422,606 B2 | 9/2008 | Ung-Chhun et al. |
| 7,423,032 B2 | 9/2008 | Ozaki et al. |
| 7,426,413 B2 | 9/2008 | Balczewski et al. |

(56) References Cited

U.S. PATENT DOCUMENTS

| | | |
|---|---|---|
| 7,427,279 B2 | 9/2008 | Frazier et al. |
| 7,427,287 B2 | 9/2008 | Turovskiy et al. |
| 7,427,291 B2 | 9/2008 | Liddicoat et al. |
| 7,429,269 B2 | 9/2008 | Schwammenthal et al. |
| 7,430,448 B1 | 9/2008 | Zimmer et al. |
| 7,430,484 B2 | 9/2008 | Ohara |
| 7,431,691 B1 | 10/2008 | Wilk |
| 7,431,733 B2 | 10/2008 | Knight |
| 7,435,059 B2 | 10/2008 | Smith et al. |
| 7,435,257 B2 | 10/2008 | Lashinski et al. |
| 7,442,204 B2 | 10/2008 | Schwammenthal et al. |
| RE40,570 E | 11/2008 | Carpentier et al. |
| 7,445,630 B2 | 11/2008 | Lashinski et al. |
| 7,445,631 B2 | 11/2008 | Salahieh et al. |
| 7,445,632 B2 | 11/2008 | McGuckin, Jr. et al. |
| 7,452,371 B2 | 11/2008 | Pavcnik et al. |
| 7,455,689 B2 | 11/2008 | Johnson |
| 7,462,156 B2 | 12/2008 | Mitrev |
| 7,462,184 B2 | 12/2008 | Worley et al. |
| 7,462,191 B2 | 12/2008 | Spenser et al. |
| 7,468,050 B1 | 12/2008 | Kantrowitz |
| 7,470,284 B2 | 12/2008 | Lambrecht et al. |
| 7,470,285 B2 | 12/2008 | Nugent et al. |
| 7,473,271 B2 | 1/2009 | Gunderson |
| 7,473,275 B2 | 1/2009 | Marquez |
| 7,473,417 B2 | 1/2009 | Zeltinger et al. |
| 7,476,196 B2 | 1/2009 | Spence et al. |
| 7,476,199 B2 | 1/2009 | Spence et al. |
| 7,476,200 B2 | 1/2009 | Tal |
| 7,476,244 B2 | 1/2009 | Buzzard et al. |
| 7,481,838 B2 | 1/2009 | Carpentier et al. |
| 7,485,088 B2 | 2/2009 | Murphy et al. |
| 7,485,143 B2 | 2/2009 | Webler et al. |
| 7,488,346 B2 | 2/2009 | Navia |
| 7,491,232 B2 | 2/2009 | Bolduc et al. |
| 7,493,869 B1 | 2/2009 | Foster et al. |
| 7,497,824 B2 | 3/2009 | Taylor |
| 7,500,949 B2 | 3/2009 | Gottlieb et al. |
| 7,500,989 B2 | 3/2009 | Solem et al. |
| 7,503,929 B2 | 3/2009 | Johnson et al. |
| 7,503,930 B2 | 3/2009 | Sharkawy et al. |
| 7,507,199 B2 | 3/2009 | Wang et al. |
| 7,510,572 B2 | 3/2009 | Gabbay |
| 7,510,574 B2 | 3/2009 | L et al. |
| 7,510,575 B2 | 3/2009 | Spenser et al. |
| 7,510,577 B2 | 3/2009 | Moaddeb et al. |
| 7,513,863 B2 | 4/2009 | Bolling et al. |
| 7,513,909 B2 | 4/2009 | Lane et al. |
| 7,522,950 B2 | 4/2009 | Fuimaono et al. |
| 7,524,330 B2 | 4/2009 | Berreklouw |
| 7,530,253 B2 | 5/2009 | Spenser et al. |
| 7,530,995 B2 | 5/2009 | Quijano et al. |
| 7,534,261 B2 | 5/2009 | Friedman |
| 7,544,206 B2 | 6/2009 | Cohn |
| 7,547,322 B2 | 6/2009 | Sarac et al. |
| 7,553,324 B2 | 6/2009 | Andreas et al. |
| 7,556,386 B2 | 7/2009 | Smith |
| 7,556,646 B2 | 7/2009 | Yang et al. |
| 7,569,071 B2 | 8/2009 | Haverkost et al. |
| 7,578,828 B2 | 8/2009 | Gittings et al. |
| 7,585,321 B2 | 9/2009 | Cribier |
| 7,591,848 B2 | 9/2009 | Allen |
| 7,594,974 B2 | 9/2009 | Cali et al. |
| 7,601,159 B2 | 10/2009 | Ewers et al. |
| 7,601,195 B2 | 10/2009 | Ichikawa |
| 7,608,099 B2 | 10/2009 | Johnson et al. |
| 7,611,534 B2 | 11/2009 | Kapadia et al. |
| 7,618,446 B2 | 11/2009 | Andersen et al. |
| 7,622,276 B2 | 11/2009 | Cunanan et al. |
| 7,625,403 B2 | 12/2009 | Krivoruchko |
| 7,628,802 B2 | 12/2009 | White et al. |
| 7,628,803 B2 | 12/2009 | Pavcnik et al. |
| 7,632,296 B2 | 12/2009 | Malewicz |
| 7,632,298 B2 | 12/2009 | Hijlkema et al. |
| 7,635,386 B1 | 12/2009 | Gammie |
| 7,641,687 B2 | 1/2010 | Chinn et al. |
| 7,651,519 B2 | 1/2010 | Dittman |
| 7,655,034 B2 | 2/2010 | Mitchell et al. |
| 7,674,282 B2 | 3/2010 | Wu et al. |
| 7,682,390 B2 | 3/2010 | Seguin |
| 7,704,222 B2 | 4/2010 | Wilk et al. |
| 7,704,277 B2 | 4/2010 | Zakay et al. |
| 7,712,606 B2 | 5/2010 | Salahieh et al. |
| 7,717,955 B2 | 5/2010 | Lane et al. |
| 7,722,638 B2 | 5/2010 | Deyette, Jr. et al. |
| 7,722,662 B2 | 5/2010 | Steinke et al. |
| 7,722,666 B2 | 5/2010 | Lafontaine |
| 7,722,671 B1 | 5/2010 | Carlyle et al. |
| 7,731,742 B2 | 6/2010 | Schlick et al. |
| 7,735,493 B2 | 6/2010 | Van Der Burg et al. |
| 7,736,327 B2 | 6/2010 | Wilk et al. |
| 7,736,388 B2 | 6/2010 | Goldfarb et al. |
| 7,743,481 B2 | 6/2010 | Lafont et al. |
| 7,748,389 B2 | 7/2010 | Salahieh et al. |
| 7,758,625 B2 | 7/2010 | Wu et al. |
| 7,763,065 B2 | 7/2010 | Schmid et al. |
| 7,771,463 B2 | 8/2010 | Ton et al. |
| 7,771,467 B2 | 8/2010 | Svensson |
| 7,776,083 B2 | 8/2010 | Vesely |
| 7,780,725 B2 | 8/2010 | Haug et al. |
| 7,780,726 B2 | 8/2010 | Seguin |
| 7,785,360 B2 | 8/2010 | Freitag |
| 7,794,487 B2 | 9/2010 | Majercak et al. |
| 7,799,046 B2 | 9/2010 | White et al. |
| 7,799,065 B2 | 9/2010 | Pappas |
| 7,803,185 B2 | 9/2010 | Gabbay |
| 7,806,919 B2 | 10/2010 | Bloom et al. |
| 7,823,267 B2 | 11/2010 | Bolduc |
| 7,824,442 B2 | 11/2010 | Salahieh et al. |
| 7,824,443 B2 | 11/2010 | Salahieh et al. |
| 7,833,262 B2 | 11/2010 | McGuckin, Jr. et al. |
| 7,837,727 B2 | 11/2010 | Goetz et al. |
| 7,846,203 B2 | 12/2010 | Cribier |
| 7,846,204 B2 | 12/2010 | Letac et al. |
| 7,854,758 B2 | 12/2010 | Taheri |
| 7,857,845 B2 | 12/2010 | Stacchino et al. |
| 7,862,602 B2 | 1/2011 | Licata et al. |
| 7,867,274 B2 | 1/2011 | Hill et al. |
| 7,887,583 B2 | 2/2011 | Macoviak |
| 7,892,276 B2 | 2/2011 | Stocker et al. |
| 7,892,292 B2 | 2/2011 | Stack et al. |
| 7,896,913 B2 | 3/2011 | Damm et al. |
| 7,896,915 B2 | 3/2011 | Guyenot et al. |
| 7,914,569 B2 | 3/2011 | Nguyen et al. |
| 7,914,574 B2 | 3/2011 | Schmid et al. |
| 7,914,575 B2 | 3/2011 | Guyenot et al. |
| 7,918,880 B2 | 4/2011 | Austin |
| 7,927,363 B2 | 4/2011 | Perouse |
| 7,938,851 B2 | 5/2011 | Olson et al. |
| 7,947,071 B2 | 5/2011 | Schmid et al. |
| 7,947,075 B2 | 5/2011 | Goetz et al. |
| 7,951,189 B2 | 5/2011 | Haverkost et al. |
| 7,959,666 B2 | 6/2011 | Salahieh et al. |
| 7,959,672 B2 | 6/2011 | Salahieh et al. |
| 7,967,853 B2 | 6/2011 | Eidenschink et al. |
| 7,972,359 B2 | 7/2011 | Kreidler |
| 7,972,376 B1 | 7/2011 | Dove et al. |
| 7,972,378 B2 | 7/2011 | Tabor et al. |
| 7,988,724 B2 | 8/2011 | Salahieh et al. |
| 7,993,386 B2 | 8/2011 | Elliott |
| 8,002,824 B2 | 8/2011 | Jenson et al. |
| 8,002,825 B2 | 8/2011 | Letac et al. |
| 8,012,198 B2 | 9/2011 | Hill et al. |
| 8,021,421 B2 | 9/2011 | Fogarty et al. |
| RE42,818 E | 10/2011 | Cali et al. |
| RE42,857 E | 10/2011 | Cali et al. |
| 8,038,704 B2 | 10/2011 | Sherburne |
| 8,038,709 B2 | 10/2011 | Palasis et al. |
| 8,043,450 B2 | 10/2011 | Cali et al. |
| 8,048,153 B2 | 11/2011 | Salahieh et al. |
| 8,052,715 B2 | 11/2011 | Quinn et al. |
| 8,052,749 B2 | 11/2011 | Salahieh et al. |
| 8,052,750 B2 | 11/2011 | Tuval et al. |
| 8,057,540 B2 | 11/2011 | Letac et al. |

(56) References Cited

U.S. PATENT DOCUMENTS

| | | |
|---|---|---|
| 8,062,355 B2 | 11/2011 | Figulla et al. |
| 8,062,536 B2 | 11/2011 | Liu et al. |
| 8,062,537 B2 | 11/2011 | Tuominen et al. |
| 8,062,749 B2 | 11/2011 | Shelestak et al. |
| 8,070,799 B2 | 12/2011 | Righini et al. |
| 8,075,641 B2 | 12/2011 | Aravanis et al. |
| 8,083,788 B2 | 12/2011 | Acosta et al. |
| 8,092,518 B2 | 1/2012 | Schreck |
| 8,092,520 B2 | 1/2012 | Quadri |
| 8,092,521 B2 | 1/2012 | Figulla et al. |
| 8,128,676 B2 | 3/2012 | Cummings |
| 8,128,681 B2 | 3/2012 | Shoemaker et al. |
| 8,133,217 B2 | 3/2012 | Stokes et al. |
| 8,133,270 B2 | 3/2012 | Kheradvar et al. |
| 8,136,659 B2 | 3/2012 | Salahieh et al. |
| 8,137,394 B2 | 3/2012 | Stocker et al. |
| 8,137,398 B2 | 3/2012 | Tuval et al. |
| 8,147,534 B2 | 4/2012 | Berez et al. |
| 8,157,853 B2 | 4/2012 | Laske et al. |
| 8,167,894 B2 | 5/2012 | Miles et al. |
| 8,172,896 B2 | 5/2012 | McNamara et al. |
| 8,182,528 B2 | 5/2012 | Salahieh et al. |
| 8,192,351 B2 | 6/2012 | Fishler et al. |
| 8,206,437 B2 | 6/2012 | Bonhoeffer et al. |
| 8,211,107 B2 | 7/2012 | Parks et al. |
| 8,216,174 B2 | 7/2012 | Wilk et al. |
| 8,216,301 B2 | 7/2012 | Bonhoeffer et al. |
| 8,221,493 B2 | 7/2012 | Boyle et al. |
| 8,226,707 B2 | 7/2012 | White |
| 8,226,710 B2 | 7/2012 | Nguyen et al. |
| 8,231,670 B2 | 7/2012 | Salahieh et al. |
| 8,236,049 B2 | 8/2012 | Rowe et al. |
| 8,236,241 B2 | 8/2012 | Carpentier et al. |
| 8,246,675 B2 | 8/2012 | Zegdi |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,277,500 B2 | 10/2012 | Schmid et al. |
| 8,287,584 B2 | 10/2012 | Salahieh et al. |
| 8,303,653 B2 | 11/2012 | Bonhoeffer et al. |
| 8,308,798 B2 | 11/2012 | Pintor et al. |
| 8,317,858 B2 | 11/2012 | Straubinger et al. |
| 8,323,335 B2 | 12/2012 | Rowe et al. |
| 8,328,868 B2 | 12/2012 | Paul et al. |
| 8,343,136 B2 | 1/2013 | Howat et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,999 B2 | 1/2013 | Kheradvar et al. |
| 8,357,387 B2 | 1/2013 | Dove et al. |
| 8,366,767 B2 | 2/2013 | Zhang |
| 8,372,134 B2 | 2/2013 | Schlick et al. |
| 8,376,865 B2 | 2/2013 | Forster et al. |
| 8,377,117 B2 | 2/2013 | Keidar et al. |
| 8,382,822 B2 | 2/2013 | Pavcnik et al. |
| 8,398,704 B2 | 3/2013 | Straubinger et al. |
| 8,398,708 B2 | 3/2013 | Meiri et al. |
| 8,403,983 B2 | 3/2013 | Quadri et al. |
| 8,414,641 B2 | 4/2013 | Stocker et al. |
| 8,414,643 B2 | 4/2013 | Tuval et al. |
| 8,414,644 B2 | 4/2013 | Quadri et al. |
| 8,414,645 B2 | 4/2013 | Dwork et al. |
| 8,439,961 B2 | 5/2013 | Jagger et al. |
| 8,445,278 B2 | 5/2013 | Everaerts et al. |
| 8,460,365 B2 | 6/2013 | Haverkost et al. |
| 8,465,540 B2 | 6/2013 | Straubinger et al. |
| 8,468,667 B2 | 6/2013 | Straubinger et al. |
| 8,470,023 B2 | 6/2013 | Eidenschink et al. |
| 8,491,650 B2 | 7/2013 | Wiemeyer et al. |
| 8,512,394 B2 | 8/2013 | Schmid et al. |
| 8,512,399 B2 | 8/2013 | Lafontaine |
| 8,512,400 B2 | 8/2013 | Tran et al. |
| 8,512,401 B2 | 8/2013 | Murray, III et al. |
| 8,523,936 B2 | 9/2013 | Schmid et al. |
| 8,535,368 B2 | 9/2013 | Headley, Jr. et al. |
| 8,540,762 B2 | 9/2013 | Schmid et al. |
| 8,545,547 B2 | 10/2013 | Schmid et al. |
| 8,551,160 B2 | 10/2013 | Figulla et al. |
| 8,556,880 B2 | 10/2013 | Freyman et al. |
| 8,556,966 B2 | 10/2013 | Jenson |
| 8,568,475 B2 | 10/2013 | Nguyen et al. |
| 8,579,962 B2 | 11/2013 | Salahieh et al. |
| 8,579,965 B2 | 11/2013 | Bonhoeffer et al. |
| 8,585,756 B2 | 11/2013 | Bonhoeffer et al. |
| 8,585,759 B2 | 11/2013 | Bumbalough |
| 8,591,570 B2 | 11/2013 | Revuelta et al. |
| 8,597,226 B2 | 12/2013 | Wilk et al. |
| 8,603,159 B2 | 12/2013 | Seguin et al. |
| 8,603,160 B2 | 12/2013 | Salahieh et al. |
| 8,617,235 B2 | 12/2013 | Schmid et al. |
| 8,617,236 B2 | 12/2013 | Paul et al. |
| 8,623,074 B2 | 1/2014 | Ryan |
| 8,623,075 B2 | 1/2014 | Murray, III et al. |
| 8,623,076 B2 | 1/2014 | Salahieh et al. |
| 8,623,078 B2 | 1/2014 | Salahieh et al. |
| 8,628,562 B2 | 1/2014 | Cummings |
| 8,628,571 B1 | 1/2014 | Hacohen et al. |
| 8,647,381 B2 | 2/2014 | Essinger et al. |
| 8,668,733 B2 | 3/2014 | Haug et al. |
| 8,672,997 B2 | 3/2014 | Drasler et al. |
| 8,679,174 B2 | 3/2014 | Ottma et al. |
| 8,685,077 B2 | 4/2014 | Laske et al. |
| 8,696,743 B2 | 4/2014 | Holecek et al. |
| 8,721,713 B2 | 5/2014 | Tower et al. |
| 8,721,717 B2 | 5/2014 | Shoemaker et al. |
| 8,734,508 B2 | 5/2014 | Hastings et al. |
| 8,758,430 B2 | 6/2014 | Ferrari et al. |
| 8,764,818 B2 | 7/2014 | Gregg |
| 8,778,020 B2 | 7/2014 | Gregg et al. |
| 8,790,395 B2 | 7/2014 | Straubinger et al. |
| 8,795,305 B2 | 8/2014 | Martin et al. |
| 8,795,356 B2 | 8/2014 | Quadri et al. |
| 8,808,356 B2 | 8/2014 | Braido et al. |
| 8,808,364 B2 | 8/2014 | Palasis et al. |
| 8,828,078 B2 | 9/2014 | Salahieh et al. |
| 8,828,079 B2 | 9/2014 | Thielen et al. |
| 8,840,662 B2 | 9/2014 | Salahieh et al. |
| 8,840,663 B2 | 9/2014 | Salahieh et al. |
| 8,845,721 B2 | 9/2014 | Braido et al. |
| 8,851,286 B2 | 10/2014 | Chang et al. |
| 8,852,272 B2 | 10/2014 | Gross et al. |
| 8,858,620 B2 | 10/2014 | Salahieh et al. |
| 8,894,703 B2 | 11/2014 | Salahieh et al. |
| 8,932,349 B2 | 1/2015 | Jenson et al. |
| 8,940,014 B2 | 1/2015 | Gamarra et al. |
| 8,951,243 B2 | 2/2015 | Crisostomo et al. |
| 8,951,299 B2 | 2/2015 | Paul et al. |
| 8,956,383 B2 | 2/2015 | Aklog et al. |
| 8,992,608 B2 | 3/2015 | Haug et al. |
| 8,998,976 B2 | 4/2015 | Gregg et al. |
| 9,005,273 B2 | 4/2015 | Salahieh et al. |
| 9,011,521 B2 | 4/2015 | Haug et al. |
| 9,028,542 B2 | 5/2015 | Hill et al. |
| 9,039,756 B2 | 5/2015 | White |
| 9,044,318 B2 | 6/2015 | Straubinger et al. |
| 9,131,926 B2 | 9/2015 | Crisostomo et al. |
| 9,149,358 B2 | 10/2015 | Tabor et al. |
| 9,168,130 B2 | 10/2015 | Straubinger et al. |
| 9,168,131 B2 | 10/2015 | Yohanan et al. |
| 9,168,136 B2 | 10/2015 | Yang et al. |
| 9,180,005 B1 | 11/2015 | Lashinski et al. |
| 9,186,482 B2 | 11/2015 | Dorn |
| 9,211,266 B2 | 12/2015 | Iwazawa et al. |
| 9,216,082 B2 | 12/2015 | Von Segesser et al. |
| 9,248,037 B2 | 2/2016 | Roeder et al. |
| 9,265,608 B2 | 2/2016 | Miller et al. |
| 9,277,991 B2 | 3/2016 | Salahieh et al. |
| 9,277,993 B2 | 3/2016 | Gamarra et al. |
| 9,301,840 B2 | 4/2016 | Nguyen et al. |
| 9,301,843 B2 | 4/2016 | Richardson et al. |
| 9,308,085 B2 | 4/2016 | Salahieh et al. |
| 9,320,599 B2 | 4/2016 | Salahieh et al. |
| 9,326,853 B2 | 5/2016 | Olson et al. |
| 9,358,106 B2 | 6/2016 | Salahieh et al. |

(56) References Cited

U.S. PATENT DOCUMENTS

| | | |
|---|---|---|
| 9,358,110 B2 | 6/2016 | Paul et al. |
| 9,370,419 B2 | 6/2016 | Hill et al. |
| 9,370,421 B2 | 6/2016 | Crisostomo et al. |
| 9,387,076 B2 | 7/2016 | Paul et al. |
| 9,393,094 B2 | 7/2016 | Salahieh et al. |
| 9,393,113 B2 | 7/2016 | Salahieh et al. |
| 9,393,114 B2 | 7/2016 | Sutton et al. |
| 9,393,115 B2 | 7/2016 | Tabor et al. |
| 9,415,567 B2 | 8/2016 | Sogard et al. |
| 9,421,083 B2 | 8/2016 | Eidenschink et al. |
| 9,439,759 B2 | 9/2016 | Straubinger et al. |
| 9,463,084 B2 | 10/2016 | Stinson |
| 9,474,598 B2 | 10/2016 | Gregg et al. |
| 9,474,609 B2 | 10/2016 | Haverkost et al. |
| 9,492,276 B2 | 11/2016 | Lee et al. |
| 9,510,945 B2 | 12/2016 | Sutton et al. |
| 9,526,609 B2 | 12/2016 | Salahieh et al. |
| 9,532,872 B2 | 1/2017 | Salahieh et al. |
| 9,539,091 B2 | 1/2017 | Yang et al. |
| 9,554,924 B2 | 1/2017 | Schlick et al. |
| 9,597,432 B2 | 3/2017 | Nakamura |
| 9,649,212 B2 | 5/2017 | Fargahi |
| 9,717,593 B2 | 8/2017 | Alkhatib et al. |
| D800,908 S | 10/2017 | Hariton et al. |
| 9,775,709 B2 | 10/2017 | Miller et al. |
| 9,788,945 B2 | 10/2017 | Ottma et al. |
| 9,861,476 B2 | 1/2018 | Salahieh et al. |
| 9,867,694 B2 | 1/2018 | Girard et al. |
| 9,867,699 B2 | 1/2018 | Straubinger et al. |
| 9,872,768 B2 | 1/2018 | Paul et al. |
| 9,889,002 B2 | 2/2018 | Bonhoeffer et al. |
| 9,901,445 B2 | 2/2018 | Backus et al. |
| 9,949,824 B2 | 4/2018 | Bonhoeffer et al. |
| 9,956,075 B2 | 5/2018 | Salahieh et al. |
| 9,987,133 B2 | 6/2018 | Straubinger et al. |
| 10,092,324 B2 | 10/2018 | Gillespie et al. |
| 10,143,552 B2 | 12/2018 | Wallace et al. |
| 10,154,901 B2 | 12/2018 | Straubinger et al. |
| 10,321,987 B2 | 6/2019 | Wang et al. |
| 10,363,134 B2 | 7/2019 | Figulla et al. |
| 10,543,084 B2 | 1/2020 | Guyenot et al. |
| 10,702,382 B2 | 7/2020 | Straubinger et al. |
| 10,709,555 B2 | 7/2020 | Schreck et al. |
| 2001/0000041 A1 | 3/2001 | Selmon et al. |
| 2001/0001314 A1 | 5/2001 | Davison et al. |
| 2001/0002445 A1 | 5/2001 | Vesely |
| 2001/0004683 A1 | 6/2001 | Gambale et al. |
| 2001/0004690 A1 | 6/2001 | Gambale et al. |
| 2001/0004699 A1 | 6/2001 | Gittings et al. |
| 2001/0007956 A1 | 7/2001 | Letac et al. |
| 2001/0008969 A1 | 7/2001 | Evans et al. |
| 2001/0010017 A1 | 7/2001 | Letac et al. |
| 2001/0011187 A1 | 8/2001 | Pavcnik et al. |
| 2001/0011189 A1 | 8/2001 | Drasler et al. |
| 2001/0012948 A1 | 8/2001 | Vanney |
| 2001/0014813 A1 | 8/2001 | Saadat et al. |
| 2001/0016700 A1 | 8/2001 | Eno et al. |
| 2001/0018596 A1 | 8/2001 | Selmon et al. |
| 2001/0020172 A1 | 9/2001 | Selmon et al. |
| 2001/0021872 A1 | 9/2001 | Bailey et al. |
| 2001/0025196 A1 | 9/2001 | Chinn et al. |
| 2001/0025643 A1 | 10/2001 | Foley |
| 2001/0027287 A1 | 10/2001 | Shmulewitz et al. |
| 2001/0027338 A1 | 10/2001 | Greenberg |
| 2001/0027339 A1 | 10/2001 | Boatman et al. |
| 2001/0029385 A1 | 10/2001 | Shennib et al. |
| 2001/0032013 A1 | 10/2001 | Marton |
| 2001/0034547 A1 | 10/2001 | Hall et al. |
| 2001/0037117 A1 | 11/2001 | Gambale et al. |
| 2001/0037141 A1 | 11/2001 | Yee et al. |
| 2001/0037149 A1 | 11/2001 | Wilk |
| 2001/0039426 A1 | 11/2001 | Makower et al. |
| 2001/0039445 A1 | 11/2001 | Hall et al. |
| 2001/0039450 A1 | 11/2001 | Pavcnik et al. |
| 2001/0041902 A1 | 11/2001 | Lepulu et al. |
| 2001/0041928 A1 | 11/2001 | Pavcnik et al. |
| 2001/0041930 A1 | 11/2001 | Globerman et al. |
| 2001/0044631 A1 | 11/2001 | Akin et al. |
| 2001/0044634 A1 | 11/2001 | Don Michael et al. |
| 2001/0044647 A1 | 11/2001 | Pinchuk et al. |
| 2001/0044652 A1 | 11/2001 | Moore |
| 2001/0044656 A1 | 11/2001 | Williamson, IV et al. |
| 2001/0047165 A1 | 11/2001 | Makower et al. |
| 2001/0049523 A1 | 12/2001 | DeVore et al. |
| 2001/0051822 A1 | 12/2001 | Stack et al. |
| 2001/0053932 A1 | 12/2001 | Phelps et al. |
| 2002/0002349 A1 | 1/2002 | Flaherty et al. |
| 2002/0002396 A1 | 1/2002 | Fulkerson |
| 2002/0002401 A1 | 1/2002 | McGuckin, Jr. et al. |
| 2002/0004662 A1 | 1/2002 | Wilk |
| 2002/0004663 A1 | 1/2002 | Gittings et al. |
| 2002/0007138 A1 | 1/2002 | Wilk et al. |
| 2002/0010489 A1 | 1/2002 | Grayzel et al. |
| 2002/0010508 A1 | 1/2002 | Chobotov |
| 2002/0026233 A1 | 2/2002 | Shaknovich |
| 2002/0029014 A1 | 3/2002 | Jayaraman |
| 2002/0029079 A1 | 3/2002 | Kim et al. |
| 2002/0029981 A1 | 3/2002 | Nigam |
| 2002/0032476 A1 | 3/2002 | Gambale et al. |
| 2002/0032478 A1 | 3/2002 | Boekstegers et al. |
| 2002/0032480 A1 | 3/2002 | Spence et al. |
| 2002/0032481 A1 | 3/2002 | Gabbay |
| 2002/0035390 A1 | 3/2002 | Schaldach et al. |
| 2002/0035396 A1 | 3/2002 | Heath |
| 2002/0042650 A1 | 4/2002 | Vardi et al. |
| 2002/0042651 A1 | 4/2002 | Liddicoat et al. |
| 2002/0045846 A1 | 4/2002 | Kaplon et al. |
| 2002/0045928 A1 | 4/2002 | Boekstegers |
| 2002/0045929 A1 | 4/2002 | Diaz |
| 2002/0049486 A1 | 4/2002 | Knudson et al. |
| 2002/0052651 A1 | 5/2002 | Myers et al. |
| 2002/0055767 A1 | 5/2002 | Forde et al. |
| 2002/0055769 A1 | 5/2002 | Wang |
| 2002/0055772 A1 | 5/2002 | McGuckin, Jr. et al. |
| 2002/0055774 A1 | 5/2002 | Liddicoat |
| 2002/0055775 A1 | 5/2002 | Carpentier et al. |
| 2002/0058897 A1 | 5/2002 | Renati |
| 2002/0058987 A1 | 5/2002 | Butaric et al. |
| 2002/0058993 A1 | 5/2002 | Landau et al. |
| 2002/0058995 A1 | 5/2002 | Stevens |
| 2002/0062146 A1 | 5/2002 | Makower et al. |
| 2002/0065478 A1 | 5/2002 | Knudson et al. |
| 2002/0065485 A1 | 5/2002 | DuBois et al. |
| 2002/0072699 A1 | 6/2002 | Knudson et al. |
| 2002/0072789 A1 | 6/2002 | Hackett et al. |
| 2002/0077566 A1 | 6/2002 | Laroya et al. |
| 2002/0077654 A1 | 6/2002 | Javier, Jr. et al. |
| 2002/0077696 A1 | 6/2002 | Zadno-Azizi et al. |
| 2002/0082584 A1 | 6/2002 | Rosenman et al. |
| 2002/0082609 A1 | 6/2002 | Green |
| 2002/0092535 A1 | 7/2002 | Wilk |
| 2002/0092536 A1 | 7/2002 | LaFontaine et al. |
| 2002/0095111 A1 | 7/2002 | Tweden et al. |
| 2002/0095173 A1 | 7/2002 | Mazzocchi et al. |
| 2002/0095206 A1 | 7/2002 | Addonizio et al. |
| 2002/0095209 A1 | 7/2002 | Zadno-Azizi et al. |
| 2002/0099439 A1 | 7/2002 | Schwartz et al. |
| 2002/0100484 A1 | 8/2002 | Hall et al. |
| 2002/0103533 A1 | 8/2002 | Langberg et al. |
| 2002/0107565 A1 | 8/2002 | Greenhalgh |
| 2002/0111627 A1 | 8/2002 | Vincent-Prestigiacomo |
| 2002/0111665 A1 | 8/2002 | Lauterjung |
| 2002/0111668 A1 | 8/2002 | Smith |
| 2002/0111672 A1 | 8/2002 | Kim et al. |
| 2002/0111674 A1 | 8/2002 | Chouinard et al. |
| 2002/0117789 A1 | 8/2002 | Childers et al. |
| 2002/0120322 A1 | 8/2002 | Thompson et al. |
| 2002/0120323 A1 | 8/2002 | Thompson et al. |
| 2002/0120328 A1 | 8/2002 | Pathak et al. |
| 2002/0123698 A1 | 9/2002 | Garibotto et al. |
| 2002/0123786 A1 | 9/2002 | Gittings et al. |
| 2002/0123790 A1 | 9/2002 | White et al. |
| 2002/0123802 A1 | 9/2002 | Snyders |
| 2002/0133183 A1 | 9/2002 | Lentz et al. |

(56) References Cited

U.S. PATENT DOCUMENTS

| | | |
|---|---|---|
| 2002/0133226 A1 | 9/2002 | Marquez et al. |
| 2002/0138087 A1 | 9/2002 | Shennib et al. |
| 2002/0138138 A1 | 9/2002 | Yang |
| 2002/0143285 A1 | 10/2002 | Eno et al. |
| 2002/0143289 A1 | 10/2002 | Ellis et al. |
| 2002/0143387 A1 | 10/2002 | Soetikno et al. |
| 2002/0144696 A1 | 10/2002 | Sharkawy et al. |
| 2002/0151913 A1 | 10/2002 | Berg et al. |
| 2002/0151970 A1 | 10/2002 | Garrison et al. |
| 2002/0156522 A1 | 10/2002 | Ivancev et al. |
| 2002/0161377 A1 | 10/2002 | Rabkin |
| 2002/0161383 A1 | 10/2002 | Akin et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0161424 A1 | 10/2002 | Rapacki et al. |
| 2002/0161426 A1 | 10/2002 | Iancea |
| 2002/0165479 A1 | 11/2002 | Wilk |
| 2002/0165576 A1 | 11/2002 | Boyle et al. |
| 2002/0165606 A1 | 11/2002 | Wolf et al. |
| 2002/0173842 A1 | 11/2002 | Buchanan |
| 2002/0177766 A1 | 11/2002 | Mogul |
| 2002/0177772 A1 | 11/2002 | Altman et al. |
| 2002/0177840 A1 | 11/2002 | Farnholtz |
| 2002/0177894 A1 | 11/2002 | Acosta et al. |
| 2002/0179098 A1 | 12/2002 | Makower et al. |
| 2002/0183716 A1 | 12/2002 | Herweck et al. |
| 2002/0183781 A1 | 12/2002 | Casey et al. |
| 2002/0186558 A1 | 12/2002 | Plank et al. |
| 2002/0188341 A1 | 12/2002 | Elliott |
| 2002/0188344 A1 | 12/2002 | Bolea et al. |
| 2002/0193782 A1 | 12/2002 | Ellis et al. |
| 2002/0193871 A1 | 12/2002 | Beyersdorf et al. |
| 2002/0198594 A1 | 12/2002 | Schreck |
| 2003/0004541 A1 | 1/2003 | Linder et al. |
| 2003/0004560 A1 | 1/2003 | Chobotov et al. |
| 2003/0009189 A1 | 1/2003 | Gilson et al. |
| 2003/0014104 A1 | 1/2003 | Cribier |
| 2003/0018377 A1 | 1/2003 | Berg et al. |
| 2003/0018379 A1 | 1/2003 | Knudson et al. |
| 2003/0023300 A1 | 1/2003 | Bailey et al. |
| 2003/0023303 A1 | 1/2003 | Palmaz et al. |
| 2003/0027332 A1 | 2/2003 | Lafrance et al. |
| 2003/0028213 A1 | 2/2003 | Thill et al. |
| 2003/0028247 A1 | 2/2003 | Cali |
| 2003/0033001 A1 | 2/2003 | Igaki |
| 2003/0036791 A1 | 2/2003 | Philipp et al. |
| 2003/0036795 A1 | 2/2003 | Andersen et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0042186 A1 | 3/2003 | Boyle |
| 2003/0044315 A1 | 3/2003 | Boekstegers |
| 2003/0045828 A1 | 3/2003 | Wilk |
| 2003/0050694 A1 | 3/2003 | Yang et al. |
| 2003/0055371 A1 | 3/2003 | Wolf et al. |
| 2003/0055495 A1 | 3/2003 | Pease et al. |
| 2003/0057156 A1 | 3/2003 | Peterson et al. |
| 2003/0060844 A1 | 3/2003 | Borillo et al. |
| 2003/0065386 A1 | 4/2003 | Weadock |
| 2003/0069492 A1 | 4/2003 | Abrams et al. |
| 2003/0069646 A1 | 4/2003 | Stinson |
| 2003/0070944 A1 | 4/2003 | Nigam |
| 2003/0073973 A1 | 4/2003 | Evans et al. |
| 2003/0074058 A1 | 4/2003 | Sherry |
| 2003/0078561 A1 | 4/2003 | Gambale et al. |
| 2003/0078652 A1* | 4/2003 | Sutherland ............ A61F 2/2412 623/2.12 |
| 2003/0083730 A1 | 5/2003 | Stinson |
| 2003/0093145 A1 | 5/2003 | Lawrence-Brown et al. |
| 2003/0100918 A1 | 5/2003 | Duane |
| 2003/0100919 A1 | 5/2003 | Hopkins et al. |
| 2003/0100920 A1 | 5/2003 | Akin et al. |
| 2003/0105514 A1 | 6/2003 | Phelps et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0120195 A1 | 6/2003 | Milo et al. |
| 2003/0125795 A1 | 7/2003 | Pavcnik et al. |
| 2003/0130726 A1 | 7/2003 | Thorpe et al. |
| 2003/0130727 A1 | 7/2003 | Drasler et al. |
| 2003/0130729 A1 | 7/2003 | Paniagua et al. |
| 2003/0130746 A1 | 7/2003 | Ashworth et al. |
| 2003/0135257 A1 | 7/2003 | Taheri |
| 2003/0139796 A1 | 7/2003 | Sequin et al. |
| 2003/0139798 A1 | 7/2003 | Brown et al. |
| 2003/0139803 A1 | 7/2003 | Sequin et al. |
| 2003/0139804 A1 | 7/2003 | Hankh et al. |
| 2003/0144657 A1 | 7/2003 | Bowe et al. |
| 2003/0144732 A1 | 7/2003 | Cosgrove et al. |
| 2003/0149474 A1 | 8/2003 | Becker |
| 2003/0149475 A1 | 8/2003 | Hyodoh et al. |
| 2003/0149476 A1 | 8/2003 | Damm et al. |
| 2003/0149477 A1 | 8/2003 | Gabbay |
| 2003/0149478 A1 | 8/2003 | Figulla et al. |
| 2003/0153971 A1 | 8/2003 | Chandrasekaran |
| 2003/0153974 A1 | 8/2003 | Spenser et al. |
| 2003/0158573 A1 | 8/2003 | Gittings et al. |
| 2003/0158595 A1 | 8/2003 | Randall et al. |
| 2003/0163198 A1 | 8/2003 | Morra et al. |
| 2003/0165352 A1 | 9/2003 | Ibrahim et al. |
| 2003/0171803 A1 | 9/2003 | Shimon |
| 2003/0171805 A1 | 9/2003 | Berg et al. |
| 2003/0176884 A1 | 9/2003 | Berrada et al. |
| 2003/0181850 A1 | 9/2003 | Diamond et al. |
| 2003/0181938 A1 | 9/2003 | Roth et al. |
| 2003/0181942 A1 | 9/2003 | Sutton et al. |
| 2003/0187495 A1 | 10/2003 | Cully et al. |
| 2003/0191449 A1 | 10/2003 | Nash et al. |
| 2003/0191516 A1 | 10/2003 | Weldon et al. |
| 2003/0191519 A1 | 10/2003 | Lombardi et al. |
| 2003/0191526 A1 | 10/2003 | Van Tassel et al. |
| 2003/0195457 A1 | 10/2003 | LaFontaine et al. |
| 2003/0195458 A1 | 10/2003 | Phelps et al. |
| 2003/0195609 A1 | 10/2003 | Berenstein et al. |
| 2003/0195620 A1 | 10/2003 | Huynh et al. |
| 2003/0198722 A1 | 10/2003 | Johnston, Jr. et al. |
| 2003/0199759 A1 | 10/2003 | Richard |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0199972 A1 | 10/2003 | Zadno-Azizi et al. |
| 2003/0204160 A1 | 10/2003 | Kamm et al. |
| 2003/0204249 A1 | 10/2003 | Letort |
| 2003/0208224 A1 | 11/2003 | Broome |
| 2003/0212410 A1 | 11/2003 | Stenzel et al. |
| 2003/0212413 A1 | 11/2003 | Wilk |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216678 A1 | 11/2003 | March et al. |
| 2003/0216679 A1 | 11/2003 | Wolf et al. |
| 2003/0216774 A1 | 11/2003 | Larson |
| 2003/0220661 A1 | 11/2003 | Mowry et al. |
| 2003/0220667 A1 | 11/2003 | Van Der Burg et al. |
| 2003/0225445 A1 | 12/2003 | Derus et al. |
| 2003/0229366 A1 | 12/2003 | Reggie et al. |
| 2003/0229390 A1 | 12/2003 | Ashton et al. |
| 2003/0233117 A1 | 12/2003 | Adams et al. |
| 2003/0236542 A1 | 12/2003 | Makower |
| 2003/0236567 A1 | 12/2003 | Elliot |
| 2003/0236568 A1 | 12/2003 | Hojeibane et al. |
| 2003/0236570 A1 | 12/2003 | Cook et al. |
| 2004/0004926 A1 | 1/2004 | Maeda |
| 2004/0006298 A1 | 1/2004 | Wilk |
| 2004/0006380 A1 | 1/2004 | Buck et al. |
| 2004/0015225 A1 | 1/2004 | Kim et al. |
| 2004/0015228 A1 | 1/2004 | Lombardi et al. |
| 2004/0018651 A1 | 1/2004 | Nadeau |
| 2004/0019348 A1 | 1/2004 | Stevens et al. |
| 2004/0019374 A1 | 1/2004 | Hojeibane et al. |

(56) References Cited

U.S. PATENT DOCUMENTS

| | | |
|---|---|---|
| 2004/0026389 A1 | 2/2004 | Kessler et al. |
| 2004/0033364 A1 | 2/2004 | Spiridigliozzi et al. |
| 2004/0034411 A1 | 2/2004 | Quijano et al. |
| 2004/0037946 A1 | 2/2004 | Morra et al. |
| 2004/0039343 A1 | 2/2004 | Eppstein et al. |
| 2004/0039436 A1 | 2/2004 | Spenser et al. |
| 2004/0044350 A1 | 3/2004 | Martin et al. |
| 2004/0044361 A1 | 3/2004 | Frazier et al. |
| 2004/0044392 A1 | 3/2004 | Von Oepen |
| 2004/0044400 A1 | 3/2004 | Cheng et al. |
| 2004/0044402 A1 | 3/2004 | Jung et al. |
| 2004/0049204 A1 | 3/2004 | Harari et al. |
| 2004/0049207 A1 | 3/2004 | Goldfarb et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0058097 A1 | 3/2004 | Weder |
| 2004/0059280 A1 | 3/2004 | Makower et al. |
| 2004/0059407 A1 | 3/2004 | Escamilla et al. |
| 2004/0059409 A1 | 3/2004 | Stenzel |
| 2004/0059429 A1 | 3/2004 | Amin et al. |
| 2004/0073157 A1 | 4/2004 | Knudson et al. |
| 2004/0073198 A1 | 4/2004 | Gilson et al. |
| 2004/0073238 A1 | 4/2004 | Makower |
| 2004/0073289 A1 | 4/2004 | Hartley |
| 2004/0077987 A1 | 4/2004 | Rapacki et al. |
| 2004/0077988 A1 | 4/2004 | Tweden et al. |
| 2004/0077990 A1 | 4/2004 | Knudson et al. |
| 2004/0078950 A1 | 4/2004 | Schreck |
| 2004/0082904 A1 | 4/2004 | Houde et al. |
| 2004/0082967 A1 | 4/2004 | Broome et al. |
| 2004/0082989 A1 | 4/2004 | Cook et al. |
| 2004/0087982 A1 | 5/2004 | Eskuri |
| 2004/0088042 A1 | 5/2004 | Kim et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093016 A1 | 5/2004 | Root et al. |
| 2004/0093060 A1 | 5/2004 | Seguin et al. |
| 2004/0093063 A1 | 5/2004 | Wright et al. |
| 2004/0093070 A1 | 5/2004 | Hojeibane et al. |
| 2004/0093075 A1 | 5/2004 | Kuehne |
| 2004/0097788 A1 | 5/2004 | Mourlas et al. |
| 2004/0098022 A1 | 5/2004 | Barone |
| 2004/0098098 A1 | 5/2004 | McGuckin, Jr. et al. |
| 2004/0098099 A1 | 5/2004 | McCullagh et al. |
| 2004/0098112 A1 | 5/2004 | DiMatteo et al. |
| 2004/0102855 A1 | 5/2004 | Shank |
| 2004/0106931 A1 | 6/2004 | Guiles et al. |
| 2004/0106976 A1 | 6/2004 | Bailey et al. |
| 2004/0106990 A1 | 6/2004 | Spence et al. |
| 2004/0107004 A1 | 6/2004 | Levine et al. |
| 2004/0111096 A1 | 6/2004 | Tu et al. |
| 2004/0113306 A1 | 6/2004 | Rapacki et al. |
| 2004/0116951 A1 | 6/2004 | Rosengart |
| 2004/0116999 A1 | 6/2004 | Ledergerber |
| 2004/0117004 A1 | 6/2004 | Osborne et al. |
| 2004/0117009 A1 | 6/2004 | Cali et al. |
| 2004/0118415 A1 | 6/2004 | Hall et al. |
| 2004/0122318 A1 | 6/2004 | Flaherty et al. |
| 2004/0122347 A1 | 6/2004 | Knudson et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty et al. |
| 2004/0127847 A1 | 7/2004 | DuBois et al. |
| 2004/0127912 A1 | 7/2004 | Rabkin et al. |
| 2004/0127936 A1 | 7/2004 | Salahieh et al. |
| 2004/0127979 A1 | 7/2004 | Wilson et al. |
| 2004/0127982 A1 | 7/2004 | Machold et al. |
| 2004/0133154 A1 | 7/2004 | Flaherty et al. |
| 2004/0133225 A1 | 7/2004 | Makower |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0138745 A1 | 7/2004 | Macoviak et al. |
| 2004/0147868 A1 | 7/2004 | Bardsley et al. |
| 2004/0147869 A1 | 7/2004 | Wolf et al. |
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0153145 A1 | 8/2004 | Simionescu et al. |
| 2004/0153146 A1 | 8/2004 | Lashinski et al. |
| 2004/0158143 A1 | 8/2004 | Flaherty et al. |
| 2004/0158277 A1 | 8/2004 | Lowe et al. |
| 2004/0163094 A1 | 8/2004 | Matsui et al. |
| 2004/0167444 A1 | 8/2004 | Laroya et al. |
| 2004/0167565 A1 | 8/2004 | Beulke et al. |
| 2004/0167573 A1 | 8/2004 | Williamson, IV et al. |
| 2004/0167620 A1 | 8/2004 | Ortiz et al. |
| 2004/0168691 A1 | 9/2004 | Sharkawy et al. |
| 2004/0176791 A1 | 9/2004 | Lim et al. |
| 2004/0181140 A1 | 9/2004 | Falwell et al. |
| 2004/0186507 A1 | 9/2004 | Hall et al. |
| 2004/0186557 A1 | 9/2004 | Gambale et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0186587 A1 | 9/2004 | Ahern |
| 2004/0193180 A1 | 9/2004 | Buzzard et al. |
| 2004/0193244 A1 | 9/2004 | Hartley et al. |
| 2004/0193252 A1 | 9/2004 | Perez et al. |
| 2004/0193261 A1 | 9/2004 | Berreklouw |
| 2004/0197695 A1 | 10/2004 | Aono |
| 2004/0199245 A1 | 10/2004 | Lauterjung |
| 2004/0204683 A1 | 10/2004 | McGuckin, Jr. et al. |
| 2004/0204755 A1 | 10/2004 | Robin |
| 2004/0206363 A1 | 10/2004 | McCarthy et al. |
| 2004/0210104 A1 | 10/2004 | Lau et al. |
| 2004/0210190 A1 | 10/2004 | Kohler et al. |
| 2004/0210240 A1 | 10/2004 | Saint |
| 2004/0210301 A1 | 10/2004 | Obermiller |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215317 A1 | 10/2004 | Cummings |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0219180 A1 | 11/2004 | Gambale et al. |
| 2004/0220598 A1 | 11/2004 | Bolduc et al. |
| 2004/0220655 A1 | 11/2004 | Swanson et al. |
| 2004/0225321 A1 | 11/2004 | Krolik et al. |
| 2004/0225353 A1 | 11/2004 | McGuckin, Jr. et al. |
| 2004/0225354 A1 | 11/2004 | Allen et al. |
| 2004/0225355 A1 | 11/2004 | Stevens |
| 2004/0236411 A1 | 11/2004 | Sarac et al. |
| 2004/0236418 A1 | 11/2004 | Stevens |
| 2004/0243143 A1 | 12/2004 | Corcoran et al. |
| 2004/0243221 A1 | 12/2004 | Fawzi et al. |
| 2004/0249343 A1 | 12/2004 | Cioanta |
| 2004/0254594 A1 | 12/2004 | Alfaro |
| 2004/0254636 A1 | 12/2004 | Flagle et al. |
| 2004/0260389 A1 | 12/2004 | Case et al. |
| 2004/0260390 A1 | 12/2004 | Sarac et al. |
| 2004/0260393 A1 | 12/2004 | Rahdert et al. |
| 2004/0260394 A1 | 12/2004 | Douk et al. |
| 2004/0267357 A1 | 12/2004 | Allen et al. |
| 2005/0000858 A1 | 1/2005 | Roovers |
| 2005/0004505 A1 | 1/2005 | Phelps et al. |
| 2005/0004558 A1 | 1/2005 | Gambale et al. |
| 2005/0004648 A1 | 1/2005 | Boekstegers |
| 2005/0008589 A1 | 1/2005 | Legrand et al. |
| 2005/0009000 A1 | 1/2005 | Wilhelm et al. |
| 2005/0010246 A1 | 1/2005 | Streeter et al. |
| 2005/0010285 A1 | 1/2005 | Lambrecht et al. |
| 2005/0010287 A1 | 1/2005 | Macoviak et al. |
| 2005/0015112 A1 | 1/2005 | Cohn et al. |
| 2005/0021136 A1 | 1/2005 | Xie et al. |
| 2005/0025857 A1 | 2/2005 | Schoenherr et al. |
| 2005/0027305 A1 | 2/2005 | Shiu et al. |
| 2005/0027348 A1 | 2/2005 | Case et al. |

(56) References Cited

U.S. PATENT DOCUMENTS

| | | |
|---|---|---|
| 2005/0033220 A1 | 2/2005 | Wilk et al. |
| 2005/0033398 A1 | 2/2005 | Seguin |
| 2005/0033402 A1 | 2/2005 | Cully et al. |
| 2005/0038495 A1 | 2/2005 | Greenan |
| 2005/0038509 A1 | 2/2005 | Ashe |
| 2005/0043585 A1 | 2/2005 | Datta et al. |
| 2005/0043711 A1 | 2/2005 | Corcoran et al. |
| 2005/0043757 A1 | 2/2005 | Arad et al. |
| 2005/0043759 A1 | 2/2005 | Chanduszko |
| 2005/0043760 A1 | 2/2005 | Fogarty et al. |
| 2005/0043781 A1 | 2/2005 | Foley |
| 2005/0043790 A1 | 2/2005 | Seguin |
| 2005/0049674 A1 | 3/2005 | Berra et al. |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060018 A1 | 3/2005 | Dittman |
| 2005/0060029 A1 | 3/2005 | Le et al. |
| 2005/0060030 A1 | 3/2005 | Lashinski et al. |
| 2005/0065594 A1 | 3/2005 | DiMatteo et al. |
| 2005/0070794 A1 | 3/2005 | Deal et al. |
| 2005/0070957 A1 | 3/2005 | Das |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0075725 A1 | 4/2005 | Rowe |
| 2005/0075726 A1 | 4/2005 | Svanidze et al. |
| 2005/0075727 A1 | 4/2005 | Wheatley |
| 2005/0075730 A1 | 4/2005 | Myers et al. |
| 2005/0075731 A1 | 4/2005 | Artof et al. |
| 2005/0075776 A1 | 4/2005 | Cho |
| 2005/0084595 A1 | 4/2005 | Shukla et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0090846 A1 | 4/2005 | Pedersen et al. |
| 2005/0090890 A1 | 4/2005 | Wu et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096726 A1 | 5/2005 | Sequin et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0096768 A1 | 5/2005 | Huang et al. |
| 2005/0098547 A1 | 5/2005 | Cali et al. |
| 2005/0100580 A1 | 5/2005 | Osborne et al. |
| 2005/0101903 A1 | 5/2005 | Kohler et al. |
| 2005/0101904 A1 | 5/2005 | Wilk |
| 2005/0101968 A1 | 5/2005 | Dadourian |
| 2005/0107822 A1 | 5/2005 | Wasdyke |
| 2005/0107871 A1 | 5/2005 | Realyvasquez et al. |
| 2005/0113902 A1 | 5/2005 | Geiser et al. |
| 2005/0113904 A1 | 5/2005 | Shank et al. |
| 2005/0113910 A1 | 5/2005 | Paniagua et al. |
| 2005/0119688 A1 | 6/2005 | Bergheim |
| 2005/0119728 A1 | 6/2005 | Sarac |
| 2005/0119736 A1 | 6/2005 | Zilla et al. |
| 2005/0125075 A1 | 6/2005 | Meade et al. |
| 2005/0131438 A1 | 6/2005 | Cohn |
| 2005/0137499 A1 | 6/2005 | Sheets et al. |
| 2005/0137609 A1 | 6/2005 | Guiraudon |
| 2005/0137681 A1 | 6/2005 | Shoemaker et al. |
| 2005/0137682 A1 | 6/2005 | Justino |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0138689 A1 | 6/2005 | Aukerman |
| 2005/0143804 A1 | 6/2005 | Haverkost |
| 2005/0143807 A1 | 6/2005 | Pavcnik et al. |
| 2005/0143809 A1 | 6/2005 | Salahieh et al. |
| 2005/0148997 A1 | 7/2005 | Valley et al. |
| 2005/0149159 A1 | 7/2005 | Andreas et al. |
| 2005/0149166 A1 | 7/2005 | Schaeffer et al. |
| 2005/0149181 A1 | 7/2005 | Eberhardt |
| 2005/0150775 A1 | 7/2005 | Zhang et al. |
| 2005/0159726 A1 | 7/2005 | Evans et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0171597 A1 | 8/2005 | Boatman et al. |
| 2005/0171598 A1 | 8/2005 | Schaeffer |
| 2005/0177227 A1 | 8/2005 | Heim et al. |
| 2005/0182483 A1 | 8/2005 | Osborne et al. |
| 2005/0182486 A1 | 8/2005 | Gabbay |
| 2005/0186349 A1 | 8/2005 | Loper et al. |
| 2005/0187616 A1 | 8/2005 | Realyvasquez |
| 2005/0192527 A1 | 9/2005 | Gharib et al. |
| 2005/0192665 A1 | 9/2005 | Spenser et al. |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0203818 A9 | 9/2005 | Rotman et al. |
| 2005/0209580 A1 | 9/2005 | Freyman |
| 2005/0214342 A1 | 9/2005 | Tweden et al. |
| 2005/0222664 A1 | 10/2005 | Parker |
| 2005/0222668 A1 | 10/2005 | Schaeffer et al. |
| 2005/0222674 A1 | 10/2005 | Paine |
| 2005/0228334 A1 | 10/2005 | Knudson et al. |
| 2005/0228472 A1 | 10/2005 | Case et al. |
| 2005/0228495 A1 | 10/2005 | Macoviak |
| 2005/0228496 A1 | 10/2005 | Mensah et al. |
| 2005/0234546 A1 | 10/2005 | Nugent et al. |
| 2005/0240200 A1 | 10/2005 | Bergheim |
| 2005/0240262 A1 | 10/2005 | White |
| 2005/0240263 A1 | 10/2005 | Fogarty et al. |
| 2005/0251243 A1 | 11/2005 | Seppala et al. |
| 2005/0251250 A1 | 11/2005 | Verhoeven et al. |
| 2005/0251251 A1 | 11/2005 | Cribier |
| 2005/0251252 A1 | 11/2005 | Stobie |
| 2005/0256532 A1 | 11/2005 | Nayak et al. |
| 2005/0261759 A1 | 11/2005 | Lambrecht et al. |
| 2005/0267523 A1 | 12/2005 | Devellian et al. |
| 2005/0267560 A1 | 12/2005 | Bates |
| 2005/0267567 A1 | 12/2005 | Shalev |
| 2005/0267573 A9 | 12/2005 | Macoviak et al. |
| 2005/0283231 A1 | 12/2005 | Haug et al. |
| 2005/0283962 A1 | 12/2005 | Boudjemline |
| 2005/0288627 A1 | 12/2005 | Mogul |
| 2005/0288685 A1 | 12/2005 | Gulles et al. |
| 2005/0288706 A1 | 12/2005 | Widomski et al. |
| 2006/0004439 A1 | 1/2006 | Spenser et al. |
| 2006/0004442 A1 | 1/2006 | Spenser et al. |
| 2006/0004469 A1 | 1/2006 | Sokel |
| 2006/0009841 A1 | 1/2006 | McGuckin, Jr. et al. |
| 2006/0009842 A1 | 1/2006 | Huynh et al. |

(56) References Cited

U.S. PATENT DOCUMENTS

| | | |
|---|---|---|
| 2006/0015168 A1 | 1/2006 | Gunderson |
| 2006/0025855 A1 | 2/2006 | Lashinski et al. |
| 2006/0025857 A1 | 2/2006 | Bergheim et al. |
| 2006/0028766 A1 | 2/2006 | Khizroev |
| 2006/0041218 A1 | 2/2006 | Phelps et al. |
| 2006/0047338 A1 | 3/2006 | Jenson et al. |
| 2006/0047343 A1 | 3/2006 | Oviatt et al. |
| 2006/0052736 A1 | 3/2006 | Tweden et al. |
| 2006/0052867 A1 | 3/2006 | Revuelta et al. |
| 2006/0058775 A1 | 3/2006 | Stevens et al. |
| 2006/0058864 A1 | 3/2006 | Schaeffer et al. |
| 2006/0058871 A1 | 3/2006 | Zakay et al. |
| 2006/0058872 A1 | 3/2006 | Salahieh et al. |
| 2006/0064151 A1 | 3/2006 | Guterman et al. |
| 2006/0069424 A1 | 3/2006 | Acosta et al. |
| 2006/0074477 A1 | 4/2006 | Berthiaume et al. |
| 2006/0074484 A1 | 4/2006 | Huber |
| 2006/0074485 A1 | 4/2006 | Realyvasquez |
| 2006/0077447 A1 | 4/2006 | Sojian et al. |
| 2006/0085060 A1 | 4/2006 | Campbell |
| 2006/0089711 A1 | 4/2006 | Dolan |
| 2006/0100685 A1 | 5/2006 | Seguin et al. |
| 2006/0111770 A1 | 5/2006 | Pavcnik et al. |
| 2006/0116757 A1 | 6/2006 | Lashinski et al. |
| 2006/0122692 A1 | 6/2006 | Gilad et al. |
| 2006/0135961 A1 | 6/2006 | Rosenman et al. |
| 2006/0135964 A1 | 6/2006 | Vesely |
| 2006/0136034 A1 | 6/2006 | Modesitt et al. |
| 2006/0142846 A1 | 6/2006 | Pavcnik et al. |
| 2006/0142848 A1 | 6/2006 | Gabbay |
| 2006/0149360 A1 | 7/2006 | Schwammenthal et al. |
| 2006/0155312 A1 | 7/2006 | Levine et al. |
| 2006/0155363 A1 | 7/2006 | LaDuca et al. |
| 2006/0155366 A1 | 7/2006 | LaDuca et al. |
| 2006/0161248 A1 | 7/2006 | Case et al. |
| 2006/0161249 A1 | 7/2006 | Realyvasquez et al. |
| 2006/0161265 A1 | 7/2006 | Levine et al. |
| 2006/0167474 A1 | 7/2006 | Bloom et al. |
| 2006/0167543 A1 | 7/2006 | Bailey et al. |
| 2006/0173524 A1 | 8/2006 | Salahieh et al. |
| 2006/0178740 A1 | 8/2006 | Stacchino et al. |
| 2006/0190070 A1 | 8/2006 | Dieck et al. |
| 2006/0193885 A1 | 8/2006 | Neethling et al. |
| 2006/0195134 A1 | 8/2006 | Crittenden |
| 2006/0195183 A1 | 8/2006 | Navia et al. |
| 2006/0195186 A1 | 8/2006 | Drews et al. |
| 2006/0206192 A1 | 9/2006 | Tower et al. |
| 2006/0206202 A1 | 9/2006 | Bonhoeffer et al. |
| 2006/0210597 A1 | 9/2006 | Hiles |
| 2006/0212110 A1 | 9/2006 | Osborne et al. |
| 2006/0212111 A1 | 9/2006 | Case et al. |
| 2006/0217802 A1 | 9/2006 | Ruiz et al. |
| 2006/0224183 A1 | 10/2006 | Freudenthal |
| 2006/0229561 A1 | 10/2006 | Huszar |
| 2006/0229718 A1 | 10/2006 | Marquez |
| 2006/0229719 A1 | 10/2006 | Marquez et al. |
| 2006/0241745 A1 | 10/2006 | Solem |
| 2006/0246584 A1 | 11/2006 | Covelli |
| 2006/0247570 A1 | 11/2006 | Pokorney |
| 2006/0247763 A1 | 11/2006 | Slater |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0265043 A1 | 11/2006 | Mandrusov et al. |
| 2006/0265056 A1 | 11/2006 | Nguyen et al. |
| 2006/0270958 A1 | 11/2006 | George |
| 2006/0271149 A1 | 11/2006 | Berez et al. |
| 2006/0271161 A1 | 11/2006 | Meyer et al. |
| 2006/0271166 A1 | 11/2006 | Thill et al. |
| 2006/0271175 A1 | 11/2006 | Woolfson et al. |
| 2006/0276873 A1 | 12/2006 | Sato |
| 2006/0276874 A1 | 12/2006 | Wilson et al. |
| 2006/0276882 A1 | 12/2006 | Case et al. |
| 2006/0276887 A1 | 12/2006 | Brady et al. |
| 2006/0282161 A1 | 12/2006 | Huynh et al. |
| 2006/0287668 A1 | 12/2006 | Fawzi et al. |
| 2006/0287717 A1 | 12/2006 | Rowe et al. |
| 2006/0287719 A1 | 12/2006 | Rowe et al. |
| 2006/0290027 A1 | 12/2006 | O'Connor et al. |
| 2006/0293745 A1 | 12/2006 | Carpentier et al. |
| 2007/0005129 A1 | 1/2007 | Damm et al. |
| 2007/0005131 A1 | 1/2007 | Taylor |
| 2007/0005132 A1 | 1/2007 | Simionescu et al. |
| 2007/0010876 A1 | 1/2007 | Salahieh et al. |
| 2007/0010877 A1 | 1/2007 | Salahieh et al. |
| 2007/0010878 A1 | 1/2007 | Rafiee et al. |
| 2007/0010887 A1 | 1/2007 | Williams et al. |
| 2007/0016286 A1 | 1/2007 | Herrmann et al. |
| 2007/0016288 A1 | 1/2007 | Gurskis et al. |
| 2007/0020248 A1 | 1/2007 | Everaerts et al. |
| 2007/0021826 A1 | 1/2007 | Case et al. |
| 2007/0027518 A1 | 2/2007 | Case et al. |
| 2007/0027520 A1 | 2/2007 | Sherburne |
| 2007/0027533 A1 | 2/2007 | Douk |
| 2007/0027535 A1 | 2/2007 | Purdy, Jr. et al. |
| 2007/0032856 A1 | 2/2007 | Limon |
| 2007/0038291 A1 | 2/2007 | Case et al. |
| 2007/0038295 A1 | 2/2007 | Case et al. |
| 2007/0043420 A1 | 2/2007 | Lostetter |
| 2007/0043424 A1 | 2/2007 | Pryor |
| 2007/0043431 A1 | 2/2007 | Melsheimer |
| 2007/0043435 A1 | 2/2007 | Seguin et al. |
| 2007/0050014 A1 | 3/2007 | Johnson |
| 2007/0051377 A1 | 3/2007 | Douk et al. |
| 2007/0055340 A1 | 3/2007 | Pryor |
| 2007/0056346 A1 | 3/2007 | Spenser et al. |
| 2007/0060998 A1 | 3/2007 | Butterwick et al. |
| 2007/0061002 A1 | 3/2007 | Paul, Jr. et al. |
| 2007/0061008 A1 | 3/2007 | Salahieh et al. |
| 2007/0073389 A1 | 3/2007 | Bolduc et al. |
| 2007/0073392 A1 | 3/2007 | Heyninck-Jantz et al. |
| 2007/0078504 A1 | 4/2007 | Mialhe |
| 2007/0078509 A1 | 4/2007 | Lotfy |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0093887 A1 | 4/2007 | Case et al. |
| 2007/0100427 A1 | 5/2007 | Perouse |
| 2007/0100435 A1 | 5/2007 | Case et al. |
| 2007/0100439 A1 | 5/2007 | Cangialosi et al. |
| 2007/0100440 A1 | 5/2007 | Figulla et al. |
| 2007/0100449 A1 | 5/2007 | O'Neil et al. |
| 2007/0112355 A1 | 5/2007 | Salahieh et al. |
| 2007/0112358 A1 | 5/2007 | Abbott et al. |
| 2007/0112415 A1 | 5/2007 | Bartlett |
| 2007/0112422 A1 | 5/2007 | Dehdashtian |
| 2007/0118214 A1 | 5/2007 | Salahieh et al. |
| 2007/0123700 A1 | 5/2007 | Ueda et al. |
| 2007/0123979 A1 | 5/2007 | Perier et al. |
| 2007/0135889 A1 | 6/2007 | Moore et al. |
| 2007/0142906 A1 | 6/2007 | Figulla et al. |
| 2007/0142907 A1 | 6/2007 | Moaddeb et al. |
| 2007/0155010 A1 | 7/2007 | Farnsworth et al. |
| 2007/0156233 A1 | 7/2007 | Kapadia et al. |
| 2007/0162102 A1 | 7/2007 | Ryan et al. |
| 2007/0162103 A1 | 7/2007 | Case et al. |
| 2007/0162107 A1 | 7/2007 | Haug et al. |
| 2007/0162113 A1 | 7/2007 | Sharkawy et al. |
| 2007/0173918 A1 | 7/2007 | Dreher et al. |
| 2007/0173932 A1 | 7/2007 | Cali et al. |
| 2007/0179592 A1 | 8/2007 | Schaeffer |
| 2007/0179600 A1 | 8/2007 | Vardi |
| 2007/0185513 A1 | 8/2007 | Woolfson et al. |
| 2007/0185565 A1 | 8/2007 | Schwammenthal et al. |
| 2007/0185571 A1 | 8/2007 | Kapadia et al. |
| 2007/0198078 A1 | 8/2007 | Berra et al. |
| 2007/0198097 A1 | 8/2007 | Zegdi |
| 2007/0203391 A1 | 8/2007 | Bloom et al. |
| 2007/0203503 A1 | 8/2007 | Salahieh et al. |
| 2007/0203560 A1 | 8/2007 | Forster et al. |
| 2007/0203576 A1 | 8/2007 | Lee et al. |
| 2007/0208550 A1 | 9/2007 | Cao et al. |

(56) References Cited

U.S. PATENT DOCUMENTS

| | | |
|---|---|---|
| 2007/0213813 A1 | 9/2007 | Von Segesser et al. |
| 2007/0225681 A1 | 9/2007 | House |
| 2007/0225802 A1 | 9/2007 | Forsell |
| 2007/0232898 A1 | 10/2007 | Huynh et al. |
| 2007/0233222 A1 | 10/2007 | Roeder et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Chia et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244543 A1 | 10/2007 | Mitchell |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244551 A1 | 10/2007 | Stobie |
| 2007/0244552 A1 | 10/2007 | Salahieh et al. |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250151 A1 | 10/2007 | Pereira |
| 2007/0250160 A1 | 10/2007 | Rafiee |
| 2007/0255386 A1 | 11/2007 | Tenne |
| 2007/0255390 A1 | 11/2007 | Ducke et al. |
| 2007/0255394 A1 | 11/2007 | Ryan |
| 2007/0255396 A1 | 11/2007 | Douk et al. |
| 2007/0260301 A1 | 11/2007 | Chuter et al. |
| 2007/0260327 A1 | 11/2007 | Case et al. |
| 2007/0265701 A1 | 11/2007 | Gurskis et al. |
| 2007/0270751 A1 | 11/2007 | Stangenes et al. |
| 2007/0270943 A1 | 11/2007 | Solem et al. |
| 2007/0273813 A1 | 11/2007 | Yoshida et al. |
| 2007/0282436 A1 | 12/2007 | Pinchuk |
| 2007/0287717 A1 | 12/2007 | Fanning et al. |
| 2007/0288000 A1 | 12/2007 | Bonan |
| 2007/0288087 A1 | 12/2007 | Fearnot et al. |
| 2007/0288089 A1 | 12/2007 | Gurskis et al. |
| 2008/0004688 A1 | 1/2008 | Spenser et al. |
| 2008/0004696 A1 | 1/2008 | Vesely |
| 2008/0009934 A1 | 1/2008 | Schneider et al. |
| 2008/0009940 A1 | 1/2008 | Cribier |
| 2008/0015671 A1 | 1/2008 | Bonhoeffer |
| 2008/0021546 A1 | 1/2008 | Patz et al. |
| 2008/0021552 A1 | 1/2008 | Gabbay |
| 2008/0022504 A1 | 1/2008 | Melsheimer |
| 2008/0033534 A1 | 2/2008 | Cook et al. |
| 2008/0033541 A1 | 2/2008 | Gelbart et al. |
| 2008/0039925 A1 | 2/2008 | Ishimaru et al. |
| 2008/0039934 A1 | 2/2008 | Styrc |
| 2008/0045921 A1 | 2/2008 | Anderson et al. |
| 2008/0048656 A1 | 2/2008 | Tan et al. |
| 2008/0065001 A1 | 3/2008 | DiNucci et al. |
| 2008/0065011 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077227 A1 | 3/2008 | Ouellette et al. |
| 2008/0077234 A1 | 3/2008 | Styrc |
| 2008/0077236 A1 | 3/2008 | Letac et al. |
| 2008/0082165 A1 | 4/2008 | Wilson et al. |
| 2008/0082166 A1 | 4/2008 | Styrc et al. |
| 2008/0086205 A1 | 4/2008 | Gordy et al. |
| 2008/0097586 A1 | 4/2008 | Pavcnik et al. |
| 2008/0102439 A1 | 5/2008 | Tian et al. |
| 2008/0109070 A1 | 5/2008 | Wagner et al. |
| 2008/0125859 A1 | 5/2008 | Salahieh et al. |
| 2008/0127707 A1 | 6/2008 | Kokish et al. |
| 2008/0133002 A1 | 6/2008 | Gelbart et al. |
| 2008/0133003 A1 | 6/2008 | Seguin et al. |
| 2008/0140188 A1 | 6/2008 | Rahdert et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichou et al. |
| 2008/0154356 A1 | 6/2008 | Obermiller et al. |
| 2008/0161909 A1 | 7/2008 | Kheradvar et al. |
| 2008/0161910 A1 | 7/2008 | Revuelta et al. |
| 2008/0161911 A1 | 7/2008 | Revuelta et al. |
| 2008/0172119 A1 | 7/2008 | Yamasaki et al. |
| 2008/0177381 A1 | 7/2008 | Navia et al. |
| 2008/0183273 A1 | 7/2008 | Mesana et al. |
| 2008/0188928 A1 | 8/2008 | Salahieh et al. |
| 2008/0195193 A1 | 8/2008 | Purdy et al. |
| 2008/0195199 A1 | 8/2008 | Kheradvar et al. |
| 2008/0200977 A1 | 8/2008 | Paul et al. |
| 2008/0208209 A1 | 8/2008 | Fischer et al. |
| 2008/0208327 A1 | 8/2008 | Rowe |
| 2008/0208328 A1 | 8/2008 | Antocci et al. |
| 2008/0208332 A1 | 8/2008 | Lamphere et al. |
| 2008/0215143 A1 | 9/2008 | Seguin |
| 2008/0215144 A1 | 9/2008 | Ryan et al. |
| 2008/0221672 A1 | 9/2008 | Lamphere et al. |
| 2008/0221703 A1 | 9/2008 | Que et al. |
| 2008/0228254 A1 | 9/2008 | Ryan |
| 2008/0228263 A1 | 9/2008 | Ryan |
| 2008/0234443 A1 | 9/2008 | Kiss et al. |
| 2008/0234797 A1 | 9/2008 | Styrc |
| 2008/0234814 A1 | 9/2008 | Salahieh et al. |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262590 A1 | 10/2008 | Murray |
| 2008/0262592 A1 | 10/2008 | Jordan et al. |
| 2008/0262593 A1 | 10/2008 | Ryan et al. |
| 2008/0262602 A1 | 10/2008 | Wilk et al. |
| 2008/0264102 A1 | 10/2008 | Berra |
| 2008/0269878 A1 | 10/2008 | Iobbi |
| 2008/0275549 A1 | 11/2008 | Rowe |
| 2008/0275550 A1 | 11/2008 | Kheradvar et al. |
| 2008/0288054 A1 | 11/2008 | Pulnev et al. |
| 2009/0005863 A1 | 1/2009 | Goetz et al. |
| 2009/0012356 A1 | 1/2009 | Dann et al. |
| 2009/0012600 A1 | 1/2009 | Styrc et al. |
| 2009/0030512 A1 | 1/2009 | Thielen et al. |
| 2009/0048656 A1 | 2/2009 | Wen |
| 2009/0054968 A1 | 2/2009 | Bonhoeffer et al. |
| 2009/0054969 A1 | 2/2009 | Salahieh et al. |
| 2009/0054976 A1 | 2/2009 | Tuval et al. |
| 2009/0062908 A1 | 3/2009 | Bonhoeffer et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0069890 A1 | 3/2009 | Suri et al. |
| 2009/0076598 A1 | 3/2009 | Salahieh et al. |
| 2009/0082844 A1 | 3/2009 | Zacharias et al. |
| 2009/0082858 A1 | 3/2009 | Nugent et al. |
| 2009/0085900 A1 | 4/2009 | Weiner |
| 2009/0093876 A1 | 4/2009 | Nitzan et al. |
| 2009/0093877 A1 | 4/2009 | Keidar et al. |
| 2009/0099640 A1 | 4/2009 | Weng |
| 2009/0099641 A1 | 4/2009 | Wu et al. |
| 2009/0099643 A1 | 4/2009 | Hyodoh et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0157175 A1 | 6/2009 | Benichou |
| 2009/0163951 A1 | 6/2009 | Simmons et al. |
| 2009/0164004 A1 | 6/2009 | Cohn |
| 2009/0164006 A1 | 6/2009 | Seguin et al. |
| 2009/0171432 A1 | 7/2009 | Von Segesser et al. |
| 2009/0171447 A1 | 7/2009 | Von Segesser et al. |

(56) References Cited

U.S. PATENT DOCUMENTS

| | | |
|---|---|---|
| 2009/0171456 A1 | 7/2009 | Kveen et al. |
| 2009/0182405 A1 | 7/2009 | Arnault De La Menardiere et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0192601 A1 | 7/2009 | Rafiee et al. |
| 2009/0198316 A1 | 8/2009 | Laske et al. |
| 2009/0198323 A1 | 8/2009 | Johnson et al. |
| 2009/0210052 A1 | 8/2009 | Forster et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222076 A1 | 9/2009 | Figulla et al. |
| 2009/0222082 A1 | 9/2009 | Lock et al. |
| 2009/0234407 A1 | 9/2009 | Hastings et al. |
| 2009/0234443 A1 | 9/2009 | Ottma et al. |
| 2009/0240264 A1 | 9/2009 | Tuval et al. |
| 2009/0240320 A1 | 9/2009 | Tuval et al. |
| 2009/0248143 A1 | 10/2009 | Laham |
| 2009/0259306 A1 | 10/2009 | Rowe |
| 2009/0264759 A1 | 10/2009 | Byrd |
| 2009/0264997 A1 | 10/2009 | Salahieh et al. |
| 2009/0276040 A1 | 11/2009 | Rowe et al. |
| 2009/0281619 A1 | 11/2009 | Le et al. |
| 2009/0287290 A1 | 11/2009 | Macaulay et al. |
| 2009/0287296 A1 | 11/2009 | Manasse |
| 2009/0287299 A1 | 11/2009 | Tabor et al. |
| 2009/0299462 A1 | 12/2009 | Fawzi et al. |
| 2009/0319037 A1 | 12/2009 | Rowe et al. |
| 2010/0004739 A1 | 1/2010 | Vesely |
| 2010/0004740 A1 | 1/2010 | Seguin et al. |
| 2010/0011564 A1 | 1/2010 | Millwee et al. |
| 2010/0030328 A1 | 2/2010 | Seguin et al. |
| 2010/0036479 A1 | 2/2010 | Hill et al. |
| 2010/0036485 A1 | 2/2010 | Seguin |
| 2010/0049313 A1 | 2/2010 | Alon et al. |
| 2010/0057051 A1 | 3/2010 | Howat et al. |
| 2010/0057185 A1 | 3/2010 | Melsheimer et al. |
| 2010/0069852 A1 | 3/2010 | Kelley |
| 2010/0069916 A1 | 3/2010 | Cully et al. |
| 2010/0070027 A1 | 3/2010 | Bonhoeffer et al. |
| 2010/0082089 A1 | 4/2010 | Quadri et al. |
| 2010/0082094 A1 | 4/2010 | Quadri et al. |
| 2010/0087913 A1 | 4/2010 | Rabkin et al. |
| 2010/0094399 A1 | 4/2010 | Dorn et al. |
| 2010/0094411 A1 | 4/2010 | Tuval et al. |
| 2010/0100167 A1 | 4/2010 | Bortlein et al. |
| 2010/0121434 A1 | 5/2010 | Paul et al. |
| 2010/0131054 A1 | 5/2010 | Tuval et al. |
| 2010/0131057 A1 | 5/2010 | Subramanian et al. |
| 2010/0137979 A1 | 6/2010 | Tuval et al. |
| 2010/0145439 A1 | 6/2010 | Seguin et al. |
| 2010/0152840 A1 | 6/2010 | Seguin et al. |
| 2010/0160725 A1 | 6/2010 | Kiser et al. |
| 2010/0161045 A1 | 6/2010 | Righini |
| 2010/0168839 A1 | 7/2010 | Braido et al. |
| 2010/0174362 A1 | 7/2010 | Straubinger et al. |
| 2010/0185275 A1 | 7/2010 | Richter et al. |
| 2010/0185277 A1 | 7/2010 | Braido et al. |
| 2010/0191320 A1 | 7/2010 | Straubinger et al. |
| 2010/0191326 A1 | 7/2010 | Alkhatib |
| 2010/0198346 A1 | 8/2010 | Keogh et al. |
| 2010/0210991 A1 | 8/2010 | Wilk et al. |
| 2010/0219092 A1 | 9/2010 | Salahieh et al. |
| 2010/0234932 A1 | 9/2010 | Arbefeuille et al. |
| 2010/0234940 A1 | 9/2010 | Dolan |
| 2010/0239917 A1 | 9/2010 | Lee et al. |
| 2010/0249908 A1 | 9/2010 | Chau et al. |
| 2010/0249915 A1 | 9/2010 | Zhang |
| 2010/0249916 A1 | 9/2010 | Zhang |
| 2010/0249917 A1 | 9/2010 | Zhang |
| 2010/0249918 A1 | 9/2010 | Zhang |
| 2010/0256723 A1 | 10/2010 | Murray |
| 2010/0262231 A1 | 10/2010 | Tuval et al. |
| 2010/0268332 A1 | 10/2010 | Tuval et al. |
| 2010/0280459 A1 | 11/2010 | Werner |
| 2010/0280495 A1 | 11/2010 | Paul et al. |
| 2010/0286768 A1 | 11/2010 | Alkhatib |
| 2010/0292779 A1 | 11/2010 | Straubinger et al. |
| 2010/0292780 A1 | 11/2010 | Straubinger et al. |
| 2010/0292785 A1 | 11/2010 | Seguin et al. |
| 2010/0298931 A1 | 11/2010 | Quadri et al. |
| 2011/0004297 A1 | 1/2011 | Sogard et al. |
| 2011/0015616 A1 | 1/2011 | Straubinger et al. |
| 2011/0022157 A1 | 1/2011 | Essinger et al. |
| 2011/0029066 A1 | 2/2011 | Gilad et al. |
| 2011/0034852 A1 | 2/2011 | Hausler et al. |
| 2011/0040366 A1 | 2/2011 | Goetz et al. |
| 2011/0040374 A1 | 2/2011 | Goetz et al. |
| 2011/0071613 A1 | 3/2011 | Wood et al. |
| 2011/0093007 A1 | 4/2011 | Abbott et al. |
| 2011/0098805 A1 | 4/2011 | Dwork et al. |
| 2011/0106244 A1 | 5/2011 | Ferrari et al. |
| 2011/0137397 A1 | 6/2011 | Chau et al. |
| 2011/0166637 A1 | 7/2011 | Irwin et al. |
| 2011/0190862 A1 | 8/2011 | Bashiri et al. |
| 2011/0190874 A1 | 8/2011 | Celermajer et al. |
| 2011/0208290 A1 | 8/2011 | Straubinger et al. |
| 2011/0208297 A1 | 8/2011 | Tuval et al. |
| 2011/0224780 A1 | 9/2011 | Tabor et al. |
| 2011/0238159 A1 | 9/2011 | Guyenot et al. |
| 2011/0238167 A1 | 9/2011 | Dove et al. |
| 2011/0257729 A1 | 10/2011 | Spenser et al. |
| 2011/0257733 A1 | 10/2011 | Dwork |
| 2011/0257735 A1 | 10/2011 | Salahieh et al. |
| 2011/0264191 A1 | 10/2011 | Rothstein |
| 2011/0264196 A1 | 10/2011 | Savage et al. |
| 2011/0264203 A1 | 10/2011 | Dwork et al. |
| 2011/0276121 A1 | 11/2011 | Levine |
| 2011/0276129 A1 | 11/2011 | Salahieh et al. |
| 2011/0288626 A1 | 11/2011 | Straubinger et al. |
| 2011/0288634 A1 | 11/2011 | Tuval et al. |
| 2011/0295363 A1 | 12/2011 | Girard et al. |
| 2011/0319989 A1 | 12/2011 | Lane et al. |
| 2012/0016469 A1 | 1/2012 | Salahieh et al. |
| 2012/0016471 A1 | 1/2012 | Salahieh et al. |
| 2012/0022633 A1 | 1/2012 | Olson et al. |
| 2012/0022642 A1 | 1/2012 | Haug et al. |
| 2012/0029627 A1 | 2/2012 | Salahieh et al. |
| 2012/0035719 A1 | 2/2012 | Forster et al. |
| 2012/0035720 A1 | 2/2012 | Cali et al. |
| 2012/0041547 A1 | 2/2012 | Duffy et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0059447 A1 | 3/2012 | Zilla et al. |
| 2012/0065464 A1 | 3/2012 | Ellis et al. |
| 2012/0078347 A1 | 3/2012 | Braido et al. |
| 2012/0078357 A1 | 3/2012 | Conklin |
| 2012/0078360 A1 | 3/2012 | Rafiee |
| 2012/0089224 A1 | 4/2012 | Haug et al. |
| 2012/0100182 A1 | 4/2012 | Mooney et al. |
| 2012/0101571 A1 | 4/2012 | Thambar et al. |
| 2012/0101572 A1 | 4/2012 | Kovalsky et al. |
| 2012/0116496 A1 | 5/2012 | Chuter et al. |
| 2012/0123515 A1 | 5/2012 | Hosford et al. |
| 2012/0123529 A1 | 5/2012 | Levi et al. |
| 2012/0130468 A1 | 5/2012 | Khosravi et al. |
| 2012/0132547 A1 | 5/2012 | Salahieh et al. |
| 2012/0136430 A1 | 5/2012 | Sochman et al. |
| 2012/0165957 A1 | 6/2012 | Everland et al. |
| 2012/0172982 A1 | 7/2012 | Stacchino et al. |
| 2012/0179244 A1 | 7/2012 | Schankereli et al. |
| 2012/0185030 A1 | 7/2012 | Igaki et al. |
| 2012/0197379 A1 | 8/2012 | Laske et al. |
| 2012/0209374 A1 | 8/2012 | Bonhoeffer et al. |
| 2012/0209376 A1 | 8/2012 | Hauser et al. |
| 2012/0221100 A1 | 8/2012 | Huber |
| 2012/0226341 A1 | 9/2012 | Schreck et al. |
| 2012/0283715 A1 | 11/2012 | Mihalik et al. |
| 2012/0283823 A1 | 11/2012 | Bonhoeffer et al. |
| 2012/0303113 A1 | 11/2012 | Benichou et al. |
| 2012/0303116 A1 | 11/2012 | Gorman, III et al. |

(56) References Cited

U.S. PATENT DOCUMENTS

| | | |
|---|---|---|
| 2012/0305441 A1 | 12/2012 | Murray et al. |
| 2012/0310332 A1 | 12/2012 | Murray et al. |
| 2012/0316637 A1 | 12/2012 | Holm et al. |
| 2012/0330408 A1 | 12/2012 | Hillukka et al. |
| 2012/0330409 A1 | 12/2012 | Haug et al. |
| 2013/0013057 A1 | 1/2013 | Salahieh et al. |
| 2013/0018457 A1 | 1/2013 | Gregg et al. |
| 2013/0030519 A1 | 1/2013 | Tran et al. |
| 2013/0030520 A1 | 1/2013 | Lee et al. |
| 2013/0046373 A1 | 2/2013 | Cartledge et al. |
| 2013/0053949 A1 | 2/2013 | Pintor et al. |
| 2013/0066342 A1 | 3/2013 | Dell et al. |
| 2013/0066419 A1 | 3/2013 | Gregg |
| 2013/0071441 A1 | 3/2013 | Iwazawa et al. |
| 2013/0073037 A1 | 3/2013 | Gregg et al. |
| 2013/0079867 A1 | 3/2013 | Hoffman et al. |
| 2013/0079869 A1 | 3/2013 | Straubinger et al. |
| 2013/0089655 A1 | 4/2013 | Gregg |
| 2013/0090728 A1 | 4/2013 | Solem |
| 2013/0090729 A1 | 4/2013 | Gregg et al. |
| 2013/0096664 A1 | 4/2013 | Goetz et al. |
| 2013/0116778 A1 | 5/2013 | Gregg et al. |
| 2013/0118949 A1 | 5/2013 | Chang et al. |
| 2013/0123757 A1 | 5/2013 | Crisostomo et al. |
| 2013/0123795 A1 | 5/2013 | Gamarra et al. |
| 2013/0123796 A1 | 5/2013 | Sutton et al. |
| 2013/0123898 A1 | 5/2013 | Tung et al. |
| 2013/0138207 A1 | 5/2013 | Quadri et al. |
| 2013/0144203 A1 | 6/2013 | Wilk et al. |
| 2013/0144276 A1 | 6/2013 | Crisostomo et al. |
| 2013/0158653 A1 | 6/2013 | Gamarra et al. |
| 2013/0158655 A1 | 6/2013 | Sutton et al. |
| 2013/0158656 A1 | 6/2013 | Sutton et al. |
| 2013/0166017 A1 | 6/2013 | Cartledge et al. |
| 2013/0178930 A1 | 7/2013 | Straubinger et al. |
| 2013/0184813 A1 | 7/2013 | Quadri et al. |
| 2013/0190865 A1 | 7/2013 | Anderson |
| 2013/0204359 A1 | 8/2013 | Thubrikar et al. |
| 2013/0231735 A1 | 9/2013 | Deem et al. |
| 2013/0245752 A1 | 9/2013 | Goetz et al. |
| 2013/0253342 A1 | 9/2013 | Griswold et al. |
| 2013/0253635 A1 | 9/2013 | Straubinger et al. |
| 2013/0253640 A1 | 9/2013 | Meiri et al. |
| 2013/0268067 A1 | 10/2013 | Forster et al. |
| 2013/0274865 A1 | 10/2013 | Haverkost et al. |
| 2013/0274870 A1 | 10/2013 | Lombardi et al. |
| 2013/0289698 A1 | 10/2013 | Wang et al. |
| 2013/0296999 A1 | 11/2013 | Burriesci et al. |
| 2013/0304199 A1 | 11/2013 | Sutton et al. |
| 2013/0310917 A1 | 11/2013 | Richter et al. |
| 2013/0310923 A1 | 11/2013 | Kheradvar et al. |
| 2013/0310928 A1 | 11/2013 | Morriss et al. |
| 2013/0325101 A1 | 12/2013 | Goetz et al. |
| 2013/0338755 A1 | 12/2013 | Goetz et al. |
| 2013/0345799 A1 | 12/2013 | Lafontaine |
| 2014/0012368 A1 | 1/2014 | Sugimoto et al. |
| 2014/0012370 A1 | 1/2014 | Bonhoeffer et al. |
| 2014/0018911 A1 | 1/2014 | Zhou et al. |
| 2014/0052239 A1 | 2/2014 | Kong et al. |
| 2014/0058501 A1 | 2/2014 | Bonhoeffer et al. |
| 2014/0083190 A1 | 3/2014 | Kaack et al. |
| 2014/0088680 A1 | 3/2014 | Costello et al. |
| 2014/0094904 A1 | 4/2014 | Salahieh et al. |
| 2014/0114390 A1 | 4/2014 | Tobis et al. |
| 2014/0114405 A1 | 4/2014 | Paul et al. |
| 2014/0114406 A1 | 4/2014 | Salahieh et al. |
| 2014/0114407 A1 | 4/2014 | Rajamannan |
| 2014/0121763 A1 | 5/2014 | Duffy et al. |
| 2014/0121766 A1 | 5/2014 | Salahieh et al. |
| 2014/0128969 A1 | 5/2014 | Hill et al. |
| 2014/0135912 A1 | 5/2014 | Salahieh et al. |
| 2014/0207229 A1 | 7/2014 | Shoemaker et al. |
| 2014/0222142 A1 | 8/2014 | Kovalsky et al. |
| 2014/0236287 A1 | 8/2014 | Clague et al. |
| 2014/0243962 A1 | 8/2014 | Wilson et al. |
| 2014/0243963 A1 | 8/2014 | Sheps et al. |
| 2014/0243967 A1 | 8/2014 | Salahieh et al. |
| 2014/0249621 A1 | 9/2014 | Eidenschink |
| 2014/0257473 A1 | 9/2014 | Rajamannan |
| 2014/0277414 A1 | 9/2014 | Kheradvar |
| 2014/0296962 A1 | 10/2014 | Cartledge et al. |
| 2014/0309732 A1 | 10/2014 | Solem |
| 2014/0316518 A1 | 10/2014 | Kheradvar et al. |
| 2014/0330371 A1* | 11/2014 | Gloss .................... A61F 2/07 623/2.17 |
| 2014/0343669 A1 | 11/2014 | Lane et al. |
| 2014/0379068 A1 | 12/2014 | Thielen et al. |
| 2015/0012085 A1 | 1/2015 | Salahieh et al. |
| 2015/0032056 A1 | 1/2015 | Okamura et al. |
| 2015/0073540 A1 | 3/2015 | Salahieh et al. |
| 2015/0073541 A1 | 3/2015 | Salahieh et al. |
| 2015/0088252 A1 | 3/2015 | Jenson et al. |
| 2015/0094804 A1 | 4/2015 | Bonhoeffer et al. |
| 2015/0105857 A1 | 4/2015 | Bonhoeffer et al. |
| 2015/0127092 A1 | 5/2015 | Straubinger et al. |
| 2015/0127094 A1 | 5/2015 | Salahieh et al. |
| 2015/0142102 A1 | 5/2015 | Lafontaine et al. |
| 2015/0209142 A1 | 7/2015 | Paul et al. |
| 2015/0209146 A1 | 7/2015 | Hill et al. |
| 2015/0223933 A1 | 8/2015 | Haug et al. |
| 2015/0238315 A1 | 8/2015 | Rabito et al. |
| 2015/0245909 A1 | 9/2015 | Salahieh et al. |
| 2015/0272731 A1 | 10/2015 | Racchini et al. |
| 2015/0320557 A1 | 11/2015 | Sutton et al. |
| 2015/0335423 A1 | 11/2015 | Gregg et al. |
| 2015/0352252 A1 | 12/2015 | Nakamura et al. |
| 2015/0359997 A1 | 12/2015 | Crisostomo et al. |
| 2016/0022418 A1 | 1/2016 | Salahieh et al. |
| 2016/0045306 A1 | 2/2016 | Agrawal et al. |
| 2016/0045307 A1 | 2/2016 | Yohanan et al. |
| 2016/0051362 A1 | 2/2016 | Cooper et al. |
| 2016/0067040 A1 | 3/2016 | Agrawal et al. |
| 2016/0120645 A1 | 5/2016 | Alon |
| 2016/0135951 A1 | 5/2016 | Salahieh et al. |
| 2016/0143731 A1 | 5/2016 | Backus et al. |
| 2016/0158003 A1 | 6/2016 | Wallace et al. |
| 2016/0166384 A1 | 6/2016 | Olson et al. |
| 2016/0199184 A1 | 7/2016 | Ma et al. |
| 2016/0206423 A1 | 7/2016 | O'Connor et al. |
| 2016/0213467 A1 | 7/2016 | Backus et al. |
| 2016/0220359 A1 | 8/2016 | Backus et al. |
| 2016/0220360 A1 | 8/2016 | Lin et al. |
| 2016/0220365 A1 | 8/2016 | Backus et al. |
| 2016/0250024 A1 | 9/2016 | Hill et al. |
| 2016/0256271 A1 | 9/2016 | Backus et al. |
| 2016/0262878 A1 | 9/2016 | Backus et al. |
| 2016/0346107 A1 | 12/2016 | Matthison-Hansen et al. |
| 2016/0354203 A1 | 12/2016 | Tuval et al. |
| 2016/0374793 A1 | 12/2016 | Lafontaine et al. |
| 2016/0376063 A1 | 12/2016 | Salahieh et al. |
| 2017/0000609 A1 | 1/2017 | Gross et al. |
| 2017/0007400 A1 | 1/2017 | Sogard et al. |
| 2017/0027693 A1 | 2/2017 | Paul et al. |
| 2017/0049563 A1 | 2/2017 | Straubinger et al. |
| 2017/0049568 A1 | 2/2017 | Straubinger et al. |
| 2017/0056172 A1 | 3/2017 | Salahieh et al. |
| 2017/0065410 A1 | 3/2017 | Straubinger et al. |
| 2017/0095595 A1 | 4/2017 | Nakamura |
| 2017/0333230 A1 | 11/2017 | Folan et al. |
| 2017/0348013 A1 | 12/2017 | Mottola et al. |
| 2018/0368976 A1 | 12/2018 | Bonhoeffer et al. |
| 2019/0328522 A1 | 10/2019 | Straubinger et al. |
| 2020/0054449 A1 | 2/2020 | Min et al. |

FOREIGN PATENT DOCUMENTS

| | | |
|---|---|---|
| AU | 2001281277 B2 | 9/2005 |
| CA | 2378589 A1 | 2/2001 |
| CA | 2381192 A1 | 2/2001 |
| CA | 2385662 A1 | 3/2001 |
| CA | 2407987 A1 | 11/2001 |
| CA | 2418958 A1 | 2/2002 |
| CA | 2435962 A1 | 8/2002 |
| CA | 2457755 A1 | 2/2003 |

(56) References Cited

FOREIGN PATENT DOCUMENTS

| | | | |
|---|---|---|---|
| CA | 2436258 A1 | 1/2005 |
| CA | 2848485 A1 | 1/2005 |
| CA | 2848490 A1 | 1/2005 |
| CA | 2595233 A1 | 7/2006 |
| CA | 2627555 A1 | 5/2007 |
| CN | 1342443 A | 4/2002 |
| CN | 1745727 A | 3/2006 |
| CN | 2762776 Y | 3/2006 |
| CN | 1897892 A | 1/2007 |
| CN | 2933337 Y | 8/2007 |
| CN | 101431963 A | 5/2009 |
| CN | 101605509 A | 12/2009 |
| CN | 101623217 A | 1/2010 |
| CN | 101700199 A | 5/2010 |
| CN | 101720211 A | 6/2010 |
| CN | 102271626 A | 12/2011 |
| CN | 102413793 A | 4/2012 |
| DE | 2815756 A1 | 10/1979 |
| DE | 3920657 A1 | 1/1991 |
| DE | 4316971 A1 | 11/1994 |
| DE | 19532846 A1 | 3/1997 |
| DE | 19546692 A1 | 6/1997 |
| DE | 19633901 A1 | 2/1998 |
| DE | 20003874 U1 | 5/2000 |
| DE | 19857887 A1 | 7/2000 |
| DE | 10010073 A1 | 9/2001 |
| DE | 10010074 A1 | 10/2001 |
| DE | 10034105 C1 | 4/2002 |
| DE | 10121210 A1 | 11/2002 |
| DE | 19546692 C2 | 11/2002 |
| DE | 10301026 A1 | 2/2004 |
| DE | 10302447 A1 | 7/2004 |
| DE | 10335948 B3 | 2/2005 |
| DE | 10010074 B4 | 4/2005 |
| DE | 19857887 B4 | 5/2005 |
| DE | 10010073 B4 | 12/2005 |
| DE | 102005003632 A1 | 8/2006 |
| DE | 102005051849 A1 | 5/2007 |
| DE | 102005052628 A1 | 5/2007 |
| DE | 202007005491 U1 | 6/2007 |
| DE | 20221871 U1 | 9/2008 |
| DE | 69937568 T2 | 9/2008 |
| EP | 0084395 A1 | 7/1983 |
| EP | 0402036 A1 | 12/1990 |
| EP | 0402176 A2 | 12/1990 |
| EP | 0411118 A1 | 2/1991 |
| EP | 0458877 A1 | 12/1991 |
| EP | 0515324 A1 | 11/1992 |
| EP | 0547135 A1 | 6/1993 |
| EP | 0402176 B1 | 4/1994 |
| EP | 0592410 A1 | 4/1994 |
| EP | 0458877 B1 | 5/1995 |
| EP | 0657147 A2 | 6/1995 |
| EP | 0402036 B1 | 4/1996 |
| EP | 0729364 A1 | 9/1996 |
| EP | 0732088 A2 | 9/1996 |
| EP | 0756498 A1 | 2/1997 |
| EP | 0778775 A1 | 6/1997 |
| EP | 0786970 A1 | 8/1997 |
| EP | 0792624 A1 | 9/1997 |
| EP | 0797957 A1 | 10/1997 |
| EP | 0797958 A1 | 10/1997 |
| EP | 0799604 A1 | 10/1997 |
| EP | 0801928 A1 | 10/1997 |
| EP | 0815798 A2 | 1/1998 |
| EP | 0826346 A1 | 3/1998 |
| EP | 0829239 A1 | 3/1998 |
| EP | 0836834 A2 | 4/1998 |
| EP | 0853921 A2 | 7/1998 |
| EP | 0858779 A1 | 8/1998 |
| EP | 0871414 A1 | 10/1998 |
| EP | 0876796 A2 | 11/1998 |
| EP | 0876803 A2 | 11/1998 |
| EP | 0778775 B1 | 1/1999 |
| EP | 0888142 A1 | 1/1999 |
| EP | 0888750 A1 | 1/1999 |
| EP | 0895752 A1 | 2/1999 |
| EP | 0896813 A2 | 2/1999 |
| EP | 0903122 A2 | 3/1999 |
| EP | 0876796 A3 | 5/1999 |
| EP | 0928615 A1 | 7/1999 |
| EP | 0934728 A2 | 8/1999 |
| EP | 0938877 A2 | 9/1999 |
| EP | 0971649 A1 | 1/2000 |
| EP | 0986348 A1 | 3/2000 |
| EP | 1000590 A1 | 5/2000 |
| EP | 1011523 A1 | 6/2000 |
| EP | 1020166 A1 | 7/2000 |
| EP | 1027870 A1 | 8/2000 |
| EP | 1041942 A1 | 10/2000 |
| EP | 1051204 A2 | 11/2000 |
| EP | 1089676 A2 | 4/2001 |
| EP | 1097676 A1 | 5/2001 |
| EP | 1112042 A1 | 7/2001 |
| EP | 1112097 A1 | 7/2001 |
| EP | 1117446 A1 | 7/2001 |
| EP | 1158937 A1 | 12/2001 |
| EP | 0547135 B1 | 1/2002 |
| EP | 0729364 B1 | 1/2002 |
| EP | 1164976 A1 | 1/2002 |
| EP | 1166721 A2 | 1/2002 |
| EP | 1171061 A1 | 1/2002 |
| EP | 1206179 A1 | 5/2002 |
| EP | 0756498 B1 | 7/2002 |
| EP | 1233731 A1 | 8/2002 |
| EP | 0986348 B1 | 9/2002 |
| EP | 1235537 A1 | 9/2002 |
| EP | 1248655 A1 | 10/2002 |
| EP | 1251804 A2 | 10/2002 |
| EP | 1251805 A2 | 10/2002 |
| EP | 1255510 A1 | 11/2002 |
| EP | 1257305 A1 | 11/2002 |
| EP | 1259193 A1 | 11/2002 |
| EP | 1259195 A1 | 11/2002 |
| EP | 0971649 B1 | 12/2002 |
| EP | 1281357 A2 | 2/2003 |
| EP | 1281375 A2 | 2/2003 |
| EP | 0888142 B1 | 5/2003 |
| EP | 1112097 B1 | 6/2003 |
| EP | 1330213 A1 | 7/2003 |
| EP | 1347785 A1 | 10/2003 |
| EP | 1354569 A1 | 10/2003 |
| EP | 1281375 A3 | 12/2003 |
| EP | 1041943 B1 | 3/2004 |
| EP | 1395208 A1 | 3/2004 |
| EP | 1401359 A2 | 3/2004 |
| EP | 0871414 B1 | 4/2004 |
| EP | 1406561 A2 | 4/2004 |
| EP | 1408882 A1 | 4/2004 |
| EP | 1414295 A2 | 5/2004 |
| EP | 1347785 B1 | 7/2004 |
| EP | 1435878 A1 | 7/2004 |
| EP | 1435879 A1 | 7/2004 |
| EP | 1441672 A1 | 8/2004 |
| EP | 0954248 B1 | 9/2004 |
| EP | 1452153 A1 | 9/2004 |
| EP | 0987998 B1 | 10/2004 |
| EP | 1206179 B1 | 10/2004 |
| EP | 1469797 A1 | 10/2004 |
| EP | 1087727 B1 | 11/2004 |
| EP | 1115452 B1 | 11/2004 |
| EP | 1117446 B1 | 11/2004 |
| EP | 1477202 A2 | 11/2004 |
| EP | 1107710 B1 | 12/2004 |
| EP | 1233731 B1 | 12/2004 |
| EP | 1484081 A1 | 12/2004 |
| EP | 1494616 A1 | 1/2005 |
| EP | 1499366 A1 | 1/2005 |
| EP | 1143879 B1 | 3/2005 |
| EP | 1516599 A2 | 3/2005 |
| EP | 1518518 A2 | 3/2005 |
| EP | 1253875 B1 | 4/2005 |
| EP | 1519697 A1 | 4/2005 |
| EP | 1521414 A1 | 4/2005 |

(56) References Cited

FOREIGN PATENT DOCUMENTS

| | | |
|---|---|---|
| EP | 1251803 B1 | 6/2005 |
| EP | 1539047 A2 | 6/2005 |
| EP | 1547533 A2 | 6/2005 |
| EP | 1551274 A2 | 7/2005 |
| EP | 1027013 B1 | 8/2005 |
| EP | 1560542 A1 | 8/2005 |
| EP | 1067869 B1 | 11/2005 |
| EP | 1600110 A1 | 11/2005 |
| EP | 1603493 A2 | 12/2005 |
| EP | 1021141 B1 | 1/2006 |
| EP | 1614400 A2 | 1/2006 |
| EP | 1616536 A2 | 1/2006 |
| EP | 1041942 B1 | 6/2006 |
| EP | 1441672 A4 | 6/2006 |
| EP | 1663070 A2 | 6/2006 |
| EP | 1667614 A1 | 6/2006 |
| EP | 1494616 A4 | 7/2006 |
| EP | 1690515 A1 | 8/2006 |
| EP | 1702247 A2 | 9/2006 |
| EP | 1051204 B1 | 12/2006 |
| EP | 1734902 A1 | 12/2006 |
| EP | 1395208 B1 | 1/2007 |
| EP | 1251805 B1 | 3/2007 |
| EP | 1255510 B1 | 4/2007 |
| EP | 1499366 B1 | 7/2007 |
| EP | 1835948 A1 | 9/2007 |
| EP | 1112042 B1 | 11/2007 |
| EP | 1863545 A2 | 12/2007 |
| EP | 1878407 A1 | 1/2008 |
| EP | 1886649 A2 | 2/2008 |
| EP | 1406561 A4 | 3/2008 |
| EP | 1893132 A2 | 3/2008 |
| EP | 1900343 A2 | 3/2008 |
| EP | 1901681 A1 | 3/2008 |
| EP | 1435878 B1 | 4/2008 |
| EP | 1886649 A3 | 4/2008 |
| EP | 1251804 B1 | 7/2008 |
| EP | 1259195 B1 | 10/2008 |
| EP | 1980220 A1 | 10/2008 |
| EP | 1994913 A2 | 11/2008 |
| EP | 1994913 A3 | 12/2008 |
| EP | 2000115 A2 | 12/2008 |
| EP | 1560542 A4 | 1/2009 |
| EP | 1408882 B1 | 2/2009 |
| EP | 2033593 A1 | 3/2009 |
| EP | 2059192 A1 | 5/2009 |
| EP | 2074964 A1 | 7/2009 |
| EP | 1401359 B1 | 8/2009 |
| EP | 1259193 B1 | 11/2010 |
| EP | 2266503 A2 | 12/2010 |
| EP | 2266504 A2 | 12/2010 |
| EP | 1893132 B1 | 3/2011 |
| EP | 2266503 A3 | 4/2011 |
| EP | 2266504 A3 | 4/2011 |
| EP | 1441672 B1 | 9/2011 |
| EP | 2364669 A2 | 9/2011 |
| EP | 2387977 A1 | 11/2011 |
| EP | 1603493 B1 | 12/2011 |
| EP | 1281375 B1 | 2/2012 |
| EP | 2364669 A3 | 3/2012 |
| EP | 2474287 A1 | 7/2012 |
| EP | 2387977 B1 | 11/2013 |
| EP | 1702247 B1 | 8/2015 |
| EP | 1519697 B1 | 11/2015 |
| EP | 1863545 B1 | 11/2015 |
| EP | 1835948 B1 | 2/2016 |
| EP | 1734902 B1 | 6/2016 |
| EP | 3028668 A1 | 6/2016 |
| EP | 1539047 B1 | 11/2016 |
| EP | 1667614 B1 | 12/2016 |
| EP | 3181096 A1 | 6/2017 |
| EP | 2659861 B1 | 3/2019 |
| JP | S5286296 A | 7/1977 |
| JP | S54137896 A | 9/1979 |
| JP | S62227352 A | 10/1987 |
| JP | S6449571 A | 2/1989 |
| JP | H0447576 B2 | 8/1992 |
| JP | H04505866 A | 10/1992 |
| JP | H06505187 A | 6/1994 |
| JP | H06343703 A | 12/1994 |
| JP | H07504091 A | 5/1995 |
| JP | H07505803 A | 6/1995 |
| JP | H07265339 A | 10/1995 |
| JP | H0833715 A | 2/1996 |
| JP | H1049571 A | 2/1998 |
| JP | H10507673 A | 7/1998 |
| JP | 2001000460 A | 1/2001 |
| JP | 2001504016 A | 3/2001 |
| JP | 2001526574 A | 12/2001 |
| JP | 2002525168 A | 8/2002 |
| JP | 2002525169 A | 8/2002 |
| JP | 2002536115 A | 10/2002 |
| JP | 2003515386 A | 5/2003 |
| JP | 2003518984 A | 6/2003 |
| JP | 2003523262 A | 8/2003 |
| JP | 2003524504 A | 8/2003 |
| JP | 2004504111 A | 2/2004 |
| JP | 2004130068 A | 4/2004 |
| JP | 2004514467 A | 5/2004 |
| JP | 2004255186 A | 9/2004 |
| JP | 2004267750 A | 9/2004 |
| JP | 2004283461 A | 10/2004 |
| JP | 2005505343 A | 2/2005 |
| JP | 2005118585 A | 5/2005 |
| JP | 2007516055 A | 6/2007 |
| JP | 2007521125 A | 8/2007 |
| JP | 2007296375 A | 11/2007 |
| JP | 2007298375 A | 11/2007 |
| JP | 2007534381 A | 11/2007 |
| JP | 2007536003 A | 12/2007 |
| JP | 2008506497 A | 3/2008 |
| JP | 2008514345 A | 5/2008 |
| JP | 2008539305 A | 11/2008 |
| JP | 2008539985 A | 11/2008 |
| JP | 2008541865 A | 11/2008 |
| JP | 2009034529 A | 2/2009 |
| JP | 2009061293 A | 3/2009 |
| JP | 2009509635 A | 3/2009 |
| JP | 2009520535 A | 5/2009 |
| JP | 2009131397 A | 6/2009 |
| JP | 2009528905 A | 8/2009 |
| JP | 2009534157 A | 9/2009 |
| JP | 2010525896 A | 7/2010 |
| JP | 2010526609 A | 8/2010 |
| JP | 2011509805 A | 3/2011 |
| JP | 4739223 B2 | 8/2011 |
| JP | 2012500665 A | 1/2012 |
| JP | 4912395 B2 | 4/2012 |
| JP | 2013521884 A | 6/2013 |
| JP | 2013526388 A | 6/2013 |
| JP | 2013540495 A | 11/2013 |
| JP | 6144009 B2 | 6/2017 |
| JP | 6449571 B2 | 1/2019 |
| WO | WO-8402266 A1 | 6/1984 |
| WO | WO-9009102 A1 | 8/1990 |
| WO | WO-9014804 A1 | 12/1990 |
| WO | WO-9117720 A1 | 11/1991 |
| WO | WO-9203990 A1 | 3/1992 |
| WO | WO-9212690 A1 | 8/1992 |
| WO | WO-9214419 A1 | 9/1992 |
| WO | WO-9320757 A2 | 10/1993 |
| WO | WO-9524873 A1 | 9/1995 |
| WO | WO-9528183 A1 | 10/1995 |
| WO | WO-9529713 A1 | 11/1995 |
| WO | WO-9613227 A1 | 5/1996 |
| WO | WO-9713463 A1 | 4/1997 |
| WO | WO-9727893 A1 | 8/1997 |
| WO | WO-9727897 A1 | 8/1997 |
| WO | WO-9727898 A1 | 8/1997 |
| WO | WO-9728839 A1 | 8/1997 |
| WO | WO-9732551 A1 | 9/1997 |
| WO | WO-9732615 A1 | 9/1997 |
| WO | WO-9808456 A1 | 3/1998 |
| WO | WO-9810714 A1 | 3/1998 |

(56) References Cited

FOREIGN PATENT DOCUMENTS

| | | |
|---|---|---|
| WO | WO-9811846 A1 | 3/1998 |
| WO | WO-9816161 A1 | 4/1998 |
| WO | WO-9819633 A1 | 5/1998 |
| WO | WO-9824373 A1 | 6/1998 |
| WO | WO-9825533 A1 | 6/1998 |
| WO | WO-9825549 A1 | 6/1998 |
| WO | WO-9838941 A1 | 9/1998 |
| WO | WO-9843556 A1 | 10/1998 |
| WO | WO-9846115 A2 | 10/1998 |
| WO | WO-9846119 A1 | 10/1998 |
| WO | WO-9846165 A1 | 10/1998 |
| WO | WO-9853759 A2 | 12/1998 |
| WO | WO-9853761 A1 | 12/1998 |
| WO | WO-9855027 A2 | 12/1998 |
| WO | WO-9857591 A1 | 12/1998 |
| WO | WO-9857592 A1 | 12/1998 |
| WO | WO-9908624 A1 | 2/1999 |
| WO | WO-9915112 A1 | 4/1999 |
| WO | WO-9921510 A1 | 5/1999 |
| WO | WO-9922656 A1 | 5/1999 |
| WO | WO-9933414 A1 | 7/1999 |
| WO | WO-9936000 A1 | 7/1999 |
| WO | WO-9936001 A1 | 7/1999 |
| WO | WO-9937337 A2 | 7/1999 |
| WO | WO-9938459 A2 | 8/1999 |
| WO | WO-9940868 A1 | 8/1999 |
| WO | WO-9942058 A1 | 8/1999 |
| WO | WO-9944524 A2 | 9/1999 |
| WO | WO-9947071 A1 | 9/1999 |
| WO | WO-9948545 A1 | 9/1999 |
| WO | WO-9948549 A2 | 9/1999 |
| WO | WO-9949793 A1 | 10/1999 |
| WO | WO-9949910 A2 | 10/1999 |
| WO | WO-9951162 A1 | 10/1999 |
| WO | WO-9953863 A1 | 10/1999 |
| WO | WO-9953987 A1 | 10/1999 |
| WO | WO-9960941 A1 | 12/1999 |
| WO | WO-9962430 A1 | 12/1999 |
| WO | WO-9966863 A2 | 12/1999 |
| WO | WO-0002503 A1 | 1/2000 |
| WO | WO-0009195 A1 | 2/2000 |
| WO | WO-0010623 A1 | 3/2000 |
| WO | WO-0012029 A1 | 3/2000 |
| WO | WO-0013722 A1 | 3/2000 |
| WO | WO-0015146 A1 | 3/2000 |
| WO | WO-0015147 A1 | 3/2000 |
| WO | WO-0015148 A1 | 3/2000 |
| WO | WO-0015149 A1 | 3/2000 |
| WO | WO-0015275 A2 | 3/2000 |
| WO | WO-0016848 A1 | 3/2000 |
| WO | WO-0018302 A2 | 4/2000 |
| WO | WO-0018323 A2 | 4/2000 |
| WO | WO-0018325 A1 | 4/2000 |
| WO | WO-0018326 A1 | 4/2000 |
| WO | WO-0018330 A1 | 4/2000 |
| WO | WO-0018331 A2 | 4/2000 |
| WO | WO-0018333 A1 | 4/2000 |
| WO | WO-0018445 A1 | 4/2000 |
| WO | WO-0018462 A2 | 4/2000 |
| WO | WO-0021436 A1 | 4/2000 |
| WO | WO-0021461 A2 | 4/2000 |
| WO | WO-0021463 A1 | 4/2000 |
| WO | WO-0021464 A1 | 4/2000 |
| WO | WO-0024449 A1 | 5/2000 |
| WO | WO-0025702 A1 | 5/2000 |
| WO | WO-0028924 A2 | 5/2000 |
| WO | WO-0033725 A2 | 6/2000 |
| WO | WO-0035376 A1 | 6/2000 |
| WO | WO-0036997 A1 | 6/2000 |
| WO | WO-0041632 A1 | 7/2000 |
| WO | WO-0041633 A1 | 7/2000 |
| WO | WO-0043051 A1 | 7/2000 |
| WO | WO-0044311 A2 | 8/2000 |
| WO | WO-0045711 A1 | 8/2000 |
| WO | WO-0045886 A2 | 8/2000 |
| WO | WO-0048531 A1 | 8/2000 |
| WO | WO-0049952 A1 | 8/2000 |
| WO | WO-0049954 A2 | 8/2000 |
| WO | WO-0049956 A1 | 8/2000 |
| WO | WO-0053125 A1 | 9/2000 |
| WO | WO-0054660 A1 | 9/2000 |
| WO | WO-0054661 A1 | 9/2000 |
| WO | WO-0056224 A1 | 9/2000 |
| WO | WO-0056225 A1 | 9/2000 |
| WO | WO-0056387 A1 | 9/2000 |
| WO | WO-0060995 A2 | 10/2000 |
| WO | WO-0062714 A1 | 10/2000 |
| WO | WO-0066007 A1 | 11/2000 |
| WO | WO-0066009 A1 | 11/2000 |
| WO | WO-0066035 A1 | 11/2000 |
| WO | WO-0069345 A1 | 11/2000 |
| WO | WO-0069367 A1 | 11/2000 |
| WO | WO-0069504 A1 | 11/2000 |
| WO | WO-0071195 A1 | 11/2000 |
| WO | WO-0078226 A1 | 12/2000 |
| WO | WO-0110209 A1 | 2/2001 |
| WO | WO-0110341 A2 | 2/2001 |
| WO | WO-0110348 A1 | 2/2001 |
| WO | WO-0117456 A1 | 3/2001 |
| WO | WO-0135870 A1 | 5/2001 |
| WO | WO-0136870 A1 | 5/2001 |
| WO | WO-0139700 A1 | 6/2001 |
| WO | WO-0141679 A1 | 6/2001 |
| WO | WO-0149213 A2 | 7/2001 |
| WO | WO-0151104 A1 | 7/2001 |
| WO | WO-0154625 A1 | 8/2001 |
| WO | WO-0158503 A1 | 8/2001 |
| WO | WO-0162189 A1 | 8/2001 |
| WO | WO-0047139 A9 | 9/2001 |
| WO | WO-0164137 A1 | 9/2001 |
| WO | WO-0182837 A2 | 11/2001 |
| WO | WO-0211647 A2 | 2/2002 |
| WO | WO-0222054 A1 | 3/2002 |
| WO | WO-0236048 A1 | 5/2002 |
| WO | WO-02051489 A2 | 7/2002 |
| WO | WO-02056798 A2 | 7/2002 |
| WO | WO-02067782 A2 | 9/2002 |
| WO | WO-02100301 A1 | 12/2002 |
| WO | WO-02102286 A1 | 12/2002 |
| WO | WO-03003949 A2 | 1/2003 |
| WO | WO-03007795 A2 | 1/2003 |
| WO | WO-03009785 A1 | 2/2003 |
| WO | WO-03011195 A2 | 2/2003 |
| WO | WO-03013239 A2 | 2/2003 |
| WO | WO-03028592 A1 | 4/2003 |
| WO | WO-03030776 A2 | 4/2003 |
| WO | WO-03032870 A1 | 4/2003 |
| WO | WO-03051231 A2 | 6/2003 |
| WO | WO-03079928 A2 | 10/2003 |
| WO | WO-03079932 A2 | 10/2003 |
| WO | WO-03079933 A1 | 10/2003 |
| WO | WO-03092554 A1 | 11/2003 |
| WO | WO-03096935 A1 | 11/2003 |
| WO | WO-03101195 A1 | 12/2003 |
| WO | WO-03103949 A1 | 12/2003 |
| WO | WO-2004004597 A2 | 1/2004 |
| WO | WO-2004016200 A1 | 2/2004 |
| WO | WO-2004016201 A2 | 2/2004 |
| WO | WO-2004019825 A1 | 3/2004 |
| WO | WO-2004023980 A2 | 3/2004 |
| WO | WO-2004026117 A2 | 4/2004 |
| WO | WO-2004026173 A2 | 4/2004 |
| WO | WO-2004028399 A2 | 4/2004 |
| WO | WO-2004030515 A2 | 4/2004 |
| WO | WO-2004043301 A1 | 5/2004 |
| WO | WO-2004062980 A1 | 7/2004 |
| WO | WO-2004064671 A2 | 8/2004 |
| WO | WO-2004082527 A2 | 9/2004 |
| WO | WO-2004082528 A2 | 9/2004 |
| WO | WO-2004096100 A1 | 11/2004 |
| WO | WO-2004103162 A2 | 12/2004 |
| WO | WO-2005002466 A2 | 1/2005 |
| WO | WO-2005011534 A1 | 2/2005 |
| WO | WO-2005021063 A2 | 3/2005 |

(56) References Cited

FOREIGN PATENT DOCUMENTS

| | | |
|---|---|---|
| WO | WO-2005032622 A2 | 4/2005 |
| WO | WO-2005034812 A1 | 4/2005 |
| WO | WO-2005062980 A2 | 7/2005 |
| WO | WO-2005063980 A1 | 7/2005 |
| WO | WO-2005070343 A1 | 8/2005 |
| WO | WO-2005072654 A1 | 8/2005 |
| WO | WO-2005102015 A2 | 11/2005 |
| WO | WO-2006065949 A2 | 6/2006 |
| WO | WO-2006066327 A1 | 6/2006 |
| WO | WO-2006070372 A2 | 7/2006 |
| WO | WO-2006076890 A1 | 7/2006 |
| WO | WO-2006086135 A2 | 8/2006 |
| WO | WO-2006089517 A1 | 8/2006 |
| WO | WO-2006102063 A2 | 9/2006 |
| WO | WO-2006108090 A2 | 10/2006 |
| WO | WO-2006118766 A1 | 11/2006 |
| WO | WO-2006124649 A1 | 11/2006 |
| WO | WO-2006127756 A2 | 11/2006 |
| WO | WO-2006127765 A1 | 11/2006 |
| WO | WO-2006129441 A1 | 12/2006 |
| WO | WO-2006132948 A1 | 12/2006 |
| WO | WO-2006133959 A1 | 12/2006 |
| WO | WO-2006138173 A2 | 12/2006 |
| WO | WO-2007047488 A2 | 4/2007 |
| WO | WO-2007047945 A2 | 4/2007 |
| WO | WO-2007048529 A1 | 5/2007 |
| WO | WO-2007051620 A1 | 5/2007 |
| WO | WO-2007058847 A2 | 5/2007 |
| WO | WO-2007059252 A1 | 5/2007 |
| WO | WO-2007071436 A2 | 6/2007 |
| WO | WO-2007098232 A2 | 8/2007 |
| WO | WO-2007120543 A1 | 10/2007 |
| WO | WO-2007123658 A1 | 11/2007 |
| WO | WO-2007123956 A2 | 11/2007 |
| WO | WO-2008028569 A1 | 3/2008 |
| WO | WO-2008031103 A2 | 3/2008 |
| WO | WO-2008035337 A2 | 3/2008 |
| WO | WO-2008045949 A2 | 4/2008 |
| WO | WO-2008051554 A2 | 5/2008 |
| WO | WO-2008070797 A2 | 6/2008 |
| WO | WO-2008079962 A1 | 7/2008 |
| WO | WO-2008098191 A2 | 8/2008 |
| WO | WO-2008101083 A2 | 8/2008 |
| WO | WO-2008125153 A1 | 10/2008 |
| WO | WO-2008137603 A2 | 11/2008 |
| WO | WO-2008138584 A1 | 11/2008 |
| WO | WO-2008150529 A1 | 12/2008 |
| WO | WO-2009045338 A1 | 4/2009 |
| WO | WO-2009053497 A1 | 4/2009 |
| WO | WO-2009085206 A2 | 7/2009 |
| WO | WO-2009094188 A2 | 7/2009 |
| WO | WO-2009094501 A1 | 7/2009 |
| WO | WO-2009106545 A1 | 9/2009 |
| WO | WO-2009149462 A2 | 12/2009 |
| WO | WO-2009155561 A2 | 12/2009 |
| WO | WO-2010022138 A2 | 2/2010 |
| WO | WO-2010044851 A1 | 4/2010 |
| WO | WO-2010086460 A1 | 8/2010 |
| WO | WO-2011008812 A1 | 1/2011 |
| WO | WO-2011008853 A2 | 1/2011 |
| WO | WO-2011060386 A2 | 5/2011 |
| WO | WO-2011102968 A1 | 8/2011 |
| WO | WO-2011104269 A1 | 9/2011 |
| WO | WO-2011120050 A1 | 9/2011 |
| WO | WO-2011133368 A1 | 10/2011 |
| WO | WO-2011144351 A2 | 11/2011 |
| WO | WO-2011147849 A1 | 12/2011 |
| WO | WO-2012023980 A1 | 2/2012 |
| WO | WO-2012036742 A2 | 3/2012 |
| WO | WO-2012038550 A1 | 3/2012 |
| WO | WO-2012039748 A2 | 3/2012 |
| WO | WO-2012082952 A2 | 6/2012 |
| WO | WO-2012106491 A1 | 8/2012 |
| WO | WO-2012142189 A1 | 10/2012 |
| WO | WO-2012145546 A1 | 10/2012 |
| WO | WO-2013028387 A2 | 2/2013 |
| WO | WO-2015028209 A1 | 3/2015 |
| WO | WO-2016093877 A1 | 6/2016 |

OTHER PUBLICATIONS

US 8,062,356 B2, 11/2011, Salahieh et al. (withdrawn)
US 8,062,357 B2, 11/2011, Salahieh et al. (withdrawn)
US 8,075,614 B2, 12/2011, Salahieh et al. (withdrawn)
US 8,133,271 B2, 03/2012, Salahieh et al. (withdrawn)
US 8,211,170 B2, 07/2012, Paul et al. (withdrawn)
Akins C.W., et al., "Risk of Reoperative Valve Replacement for Failed Mitral and Aortic Bioprostheses," The Annals of Thoracic Surgery, vol. 65, Jun. 1998, pp. 1545-1552. Retreived from th Internet: URL: http://ats.ctsnetjournals.org/cgi/contenUfull/65/6/1545.
Extended European Search Report dated Feb. 27, 2017 in EP Patent Appl. Serial No. 16186773,6 pages.
Extended European Search Report dated Sep. 29, 2014 in EP Patent Appl. Serial No. 14164680, 5 pages.
Extended European Search Report for Application No. 07116242.4-2310 dated Mar. 31, 2008, 10 pages.
Extended European Search Report for Application No. 09154935.2, dated May 29, 2009, 7 pages.
Extended European Search Report for EP Patent Appl. Serial No. 13163918.9, dated Jul. 24, 2013, 8 pages.
Extended European Search Report for EP Patent Appl. Serial No. 14179639.1, dated Mar. 9, 2015, 7 pages.
Extended European Search Report for EP Patent Appl. Serial No. 16201320.5, dated May 19, 2017, 6 pages.
Ferrari, "Entwicklung eines Verfahrens zum transvaskularen Aortenklappenersatz," Habilitationsschrift, Medizinische Fakultat der Friedrich-Schiller-Universitat Jena, Sep. 2003, pp. 1-159.
Ferrari, "Entwicklung eines Verfahrens zum transvaskularen Aortenklappenersatz," Habilitationsschrift, Medizinische Fakultät der Friedrich-Schiller-Universität Jena, Sep. 2003, pp. 49-52.
Ferrari M.W., "Transarterial Aortic Valve Replacement with a Self Expanding Stent in Pigs," Heart, vol. 90, No. 11, doi:10.1136/hrt.2003.028951, ISSN 1355-6037, XP055137208, Nov. 2004, pp. 1326-1331.
German National Library, "Entwicklung eines Verfahrens zum transvaskulären Aortenklappenersatz," bibliographic information for Ferrari M., Sep. 2004, Retreived from the Internet: URL: https://www.deutsche-digitale-bibliothek.de/item/U2RQV45RMES4YP6AHEPGN4QPJWAMGROI, 3 pages.
Gummert J.F et al., Cardiac Surgery in Germany During 2006: A Report on Behalf of the German Society for Thoracic and Cardiovascular Surgery, Thorac. Cardiov. Surg., vol. 55, Jun. 24, 2007, pp. 343-350.
Gummert J.F. et al., "Cardiac Surgery in Germany During 2007: A Report on Behalf of the German Society for Thoracic and Cardiovascular Surgery," Thorac. Cardiov. Surg., vol. 56, Sep. 2008, pp. 328-336.
Huber C.H., et al., "Direct Access Valve Replacement (DAVR)—are we entering a new era in cardiac surgery?" European Journal of Cardio-thoracic Surgery, vol. 29, Jan. 19, 2006, pp. 380-385.
International Search Report and Written Opinion for Application No. PCT/EP2013/057431 dated Jul. 26, 2013, 9 pages.
International Search Report and Written Opinion for PCT Application No. PCT/EP2006/010519 dated Mar. 1, 2007, 13 pages.
International Search Report for Application No. PCT/EP2006/012455, dated Sep. 27, 2007, 5 pages.
International Search Report for Application No. PCT/EP2011/058506, dated Nov. 3, 2011, 4 pages.
International Search Report for Application No. PCT/EP2012/067617 dated Dec. 19, 2012, 3 pages.
International Search Report for Application No. PCT/EP2012/067714 dated Dec. 18, 2012, 3 pages.
International Search Report for Application No. PCT/EP2014/065817, dated Jan. 7, 2015, 6 pages.
International Search Report for Application No. PCT/EP2016/055783, dated May 30, 2016, 5 pages.

(56) References Cited

OTHER PUBLICATIONS

International Search Report for Application No. PCT/EP2016/058532, dated Jul. 11, 2016, 4 pages.
International Search Report for Application No. PCT/US83/01932 corresponding to WO 84/02266.
International Search Report for PCT/EP2006/010023 dated Mar. 30, 2007, 6 pages.
Klein A.L., et al., "Age-related Prevalence of Valvular Regurgitation in Normal Subjects: A Comprehensive Color Flow Examination of 118 Volunteers," Journal of the American Society of Echocardiography, vol. 3, No. 1, Jan.-Feb. 1990, pp. 54-63.
Ma L., et al., "Double-crowned valved stents for off-pump mitral valve replacement," European Journal of Cardio-Thoracic Surgery, vol. 28, No. 2, Jun. 13, 2005, pp. 194-198.
Pawelec-Wojtalk M., "Closure of left ventricle perforation with the use of muscular VSD occluder," European Journal of Cardia-Thoracic Surgery, vol. 27, No. 4, Jan. 2005, pp. 714-716,
Search Report dated Oct. 15, 2003 from the European Patent Office for European Patent Application No. EP 02291953.4, 2 pages.
Search Report from the European Patent Office for European Patent Application No. EP 02291954.4, dated Dec. 2002, 4 pages.
Weerasinghe A., et al., "First Redo Heart Valve Replacement: A 10-Year Analysis," European Journal of Cardia-Thoracic Surgery, vol. 99, Feb. 1999, pp. 655-658.
International Search Report for PCT/IB2018/050438 dated Apr. 12, 2018 (3 pages).
Anabtawi I.N., et al., "Experimental evaluation of myocardial tunnelization as a method of myocardial revascularization," Journal of Thoracic and Cardiovascular Surgery, 58(5):638-646 (Nov. 1969).
"Aortenklappenbioprothese erfolgreich in der Entwicklung," May 16, 2001, 1 page (with English Translation.
Archie J.P., et al., "Intramyocardial Pressure: Effect of Preload on Transmural Distribution of Systolic Coronary Blood Flow," The American Journal of Cardiology, 35(6):904-911 (Jun. 1975).
Baba H., et al., "Hemodynamic effects of venous valves in aorta-coronary bypass grafts," The Journal of Thoracic and Cardiovascular Surgery, 71(5):774-778 (May 1976).
Blum et al., "Endoluminal Stent—Grafts for Intrarenal Abdominal Aortic Aneurysms." New Engl. J. Med., 336:13-20, Jan. 1997.
Boudjemline et al., "Percutaneous Implantation of a Biological Valve in Aoritc Position: Preliminary Results in a Sheep Study," European Heart Journal, vol. 22, p. 630, Abstract Only (Sep. 2001).
Boudjemline et al., "Percutaneous Implantation of a Biological Valve in the Aorta to Treat Aortic Valve Insufficiency—A Sheep Study." Med Sci. Monit., 8(4):BR113-116 (Apr. 2002).
Boudjemline et al., "Percutaneous Pulmonary Valve Replacement in a Large Right Ventricular Outflow Tract: An Experimental Study." Journal of the American College of Cardiology, 43(6):1082-1087 (Mar. 2004).
Boudjemline et al., "Stent Implantation Combined with a Valve Replacement to Treat Degenerated Right Ventricle to Pulmonary Artery Prosthetic Conduits," European Heart Journal vol. 22, p. 355, Abstract Only (Sep. 2001).
Boudjemline et al., "The Percutaneous Implantable Heart Valve," Progress in Pediatric Cardiology, 14:89-93 (Nov. 2001).
Bruce C.J., et al., "Right-sided Valve Disease Deserves Little More Respect," Circulation, vol. 119, No. 20, May 2009, pp. 2726-2734.
Cribier et al., "Percutaneous Transcatheter Implantation of an Aortic Valve Prosthesis for Calcific Aortic Stenosis: First Human Case", Circulation, 106(24):3006-3008 (Dec. 2002).
Dalby et al., "Non-Surgical Aortic Valve Replacement" Br. J. Cardiol., 10(6):450-452 (Nov. 2003).
EP Search Report dated Aug. 10, 2011 for EP Application No. 06824992.9.
European Search Report for EP Patent Appl. Serial No. 12179049.7 (1257), dated Oct. 30, 2012, 4 pages.
European Search Report for EP Patent Appl. Serial No. 12179075.2 (1257), dated Oct. 29, 2012, 3 pages.
European Search Report for EP Patent Appl. Serial No. 12179141.2 (1257), dated Nov. 2, 2012, 3 pages.
European Search Report for EP Patent Appl. Serial No. 12179146.1 (1257), dated Nov. 7, 2012, 8 pages.
European Search Report for EP Patent Appl. Serial No. 12179330.1 (1257), dated Nov. 22, 2012, 3 pages.
European Search Report for EP Patent Appl. Serial No. 12179338.4 (1257), dated Nov. 2, 2012, 3 pages.
European Search Report for EP Patent Appl. Serial No. 12179339.2 (1257), dated Oct. 29, 2012, 4 pages.
European Search Report for EP Patent Appl. Serial No. 12179914.2 (1257), dated Nov. 7, 2012, 6 pages.
European Search Report for EP Patent Appl. Serial No. 13150337.7 (1257), dated Jul. 9, 2013, 3 pages.
European Search Report for EP Patent Appl. Serial No. 13183134.9 (1651), dated Nov. 19, 2013, 3 pages.
European Search Report for EP Patent Appl. Serial No. 14159630.4 (1651), dated May 22, 2014, 3 pages.
European Search Report for EP Patent Appl. Serial No. 14161991.6 (1651), dated Jun. 3, 2014, 3 pages.
European Search Report for EP Patent Appl. Serial No. 15167832.3 (1651), dated Jul. 23, 2015, 3 pages.
European Search Report for EP Patent Appl. Serial No. 15167847.1 (1651), dated Jul. 23, 2015, 3 pages.
European Search Report for EP Patent Appl. Serial No. 17196833.2, dated Mar. 6, 2018, 4 pages.
European Search Report for EP Patent Appl. Serial No. 18164490.7, dated Sep. 17, 2018 5 pages.
European Search Report from EP Patent Office for EP Application No. 15177718.2, dated Jan. 18, 2016, 4 pages.
European Search Report from EP Patent Office for EP Application No. 15177731.5, dated Apr. 14, 2016, 4 pages.
European Search Report from EP Patent Office for EP Application No. 16151726.3, dated Feb. 25, 2016, 4 pages.
Extended European Search Report dated Apr. 11, 2008 in EP Patent Appl. Serial No. 081630410, 5 pages.
Extended European Search Report for Application No. 10183946.2.4-2320 dated Feb. 14, 2012, 7 pages.
Extended European Search Report dated Aug. 9, 2018 in EP Patent Appl. Serial No. 18158901.1 (1113).
Extended European Search Report dated Jun. 12, 2018 in EP Patent Appl. Serial No. 17209326.2 (1113).
Extended European Search Report dated May 16, 2012 in EP Patent Appl. Serial No. 11178135.7 (1257).
Extended European Search Report for Application No. 11178076.3-1257 dated Feb. 29, 2012, 5 pages.
Extended European Search Report from EP Patent Office for EP Application No. 17162616.1, dated Jul. 27, 2017, 7 pages.
Extended European Search Report dated Apr. 9, 2014 in EP Patent Appl. Serial No. 14164683.6.
Extended European Search Report dated May 9, 2013 in EP Patent Appl. Serial No. 130178309.4, 4 pages.
Extended European Search Report dated Aug. 19, 2011 in EP Patent Appl. Serial No. 07827132.7.
Extended European Search Report for Application No. 10168525.3-1257 dated Feb. 3, 2011, 13 pages.
Extended European Search Report for Application No. 11153142.2-1257 dated Aug. 3, 2011, 10 pages.
Extended European Search Report for Application No. 11165093.3-1257 dated Aug. 30, 2011, 6 pages.
Extended European Search Report for Application No. 11178073.0-1257 dated Oct. 14, 2011, 5 pages.
Extended European Search Report for Application No. 11178145.6-1257 dated Feb. 29, 2012, 5 pages.
Extended European Search Report for Application No. 13188858.8-1651 dated Jan. 13, 2014, 6 pages.
Extended European Search Report for Application No. 19195062 dated Jan. 2, 2020, 7 pages.
Extended European Search Report for EP Patent Appl. Serial No. 06827630.2 dated Jun. 7, 2010, 5 pages.
Extended European Search Report for EP Patent Appl. Serial No. 07110318.8, dated May 29, 2008, 10 pages.
Extended European Search Report for EP Patent Appl. Serial No. 10163478.0, dated Mar. 22, 2011, 9 pages.

(56) References Cited

OTHER PUBLICATIONS

Extended European Search Report for EP Patent Appl. Serial No. 10184842.2, dated Mar. 23, 2011, 7 pages.
Extended European Search Report for EP Patent Appl. Serial No. 11162971.3, dated Jun. 30, 2011, 5 pages.
Extended European Search Report for EP Patent Appl. Serial No. 18200191.7, dated May 6, 2019, 8 pages.
Filsoufi F., et al., "Long-term Outcomes of Tricuspid Valve Replacement in the Current Era," Ann. Thorac. Surg., vol. 80, No. 3, Sep. 2005, pp. 845-850.
International Search Report dated Dec. 29, 2003 in Intl PCT Patent Appl. U.S. Appl. No. PCT/DE2003/002669.
International Search Report and Written Opinion for PCT Application No. PCT/EP2009/052230 dated Jun. 29, 2009, 12 pages.
International Search Report and Written Opinion for PCT Application No. PCT/EP2010/052429 dated Jun. 14, 2010, 12 pages.
International Search Report and Written Opinion for PCT Application No. PCT/EP2011/002524 dated Apr. 23, 2012, 15 pages.
International Search Report and Written Opinion for PCT Application No. PCT/EP2011/052674 dated Jul. 5, 2011, 12 pages.
International Search Report for PCT Application No. PCT/US1999/020736 dated Jan. 28, 2000, 3 pages.
International Search Report and Written Opinion for PCT Application No. PCT/EP2009/050762 dated Jun. 23, 2009, 12 pages.
International Search Report & Written Opinion dated Jul. 18, 2016 for PCT Patent Appl No. PCT/EP2016/059839, 10 pages.
International Search Report and Written Opinion for Appl. No. PCT/EP2016/055783, dated May 30, 2016, 15 pages.
International Search Report and Written Opinion for Application No. PCT/IB2018/050438 dated Apr. 12, 2018, 11 pages.
International Search Report and Written Opinion for International Application No. PCT/EP2010/063306, dated Nov. 17, 2010, 9 pages.
International Search Report and Written Opinion for PCT Application No. PCT/US06/36286 dated Jul. 9, 2007, 4 pages.
International Search Report and Written Opinion for PCT Application No. PCT/US2004/041513 dated Jun. 10, 2005, 4 pages.
International Search Report and Written Opinion for PCT Application No. PCT/US2004/043607 dated Mar. 20, 2006, 4 pages.
International Search Report and Written Opinion for PCT Application No. PCT/US2005/020947 dated Oct. 6, 2005, 5 pages.
International Search Report and Written Opinion for PCT Application No. PCT/US2006/038352 dated May 19, 2008, 4 pages.
International Search Report and Written Opinion for PCT Application No. PCT/US2006/043484 dated Jun. 25, 2008, 4 pages.
International Search Report and Written Opinion for PCT Application No. PCT/US2007/003992 dated Jan. 10, 2008, 5 pages.
International Search Report and Written Opinion for PCT Application No. PCT/US2007/02970 dated Oct. 19, 2007, 7 pages.
International Search Report and Written Opinion for PCT Application No. PCT/US2009/060531 dated May 13, 2010, 6 pages.
International Search Report and Written Opinion for PCT/DE2006/000056 dated Jun. 7, 2006, 11 pages.
International Search Report and Written Opinion for PCT/EP2007/061117 dated May 20, 2008, 16 pages.
International Search Report and Written Opinion for PCT/EP2008/003803 dated Aug. 20, 2008, 10 pages.
International Search Report and Written Opinion for PCT/EP2009/055958 dated Oct. 21, 2009, 8 pages.
International Search Report and Written Opinion for PCT/EP2010/056558 dated Oct. 7, 2010, 14 pages.
International Search Report and Written Opinion for PCT/EP2012/067617 dated Dec. 19, 2012, 10 pages.
International Search Report and Written Opinion for PCT/IL2007/001149 dated May 1, 2008, 4 pages.
International Search Report and Written Opinion for PCT/US2011/027730 dated May 25, 2011, 9 pages.
International Search Report and Written Opinion of the International Search Authority for International Application No. PCT/EP2008/064558, date of completion of report is Mar. 18, 2009, 14 pages.
International Search Report for Application No. PCT/DE2001/000837, dated Aug. 7, 2001, 4 pages.
International Search Report for Application No. PCT/EP2010/057798, dated Sep. 12, 2010, 6 pages.
International Search Report for Application No. PCT/EP2011/066677, dated Feb. 17, 2012, 7 pages.
International Search Report for Application No. PCT/EP2013/073318, dated Apr. 17, 2014, 5 pages.
International Search Report for Application No. PCT/IB2008/002180, dated Apr. 15, 2009, 7 pages.
International Search Report for PCT/DE2001/000836 dated Jun. 13, 2001, 6 pages.
International Search Report for PCT/EP2007/007413, dated Jan. 28, 2008, 4 pages.
International Search Report for PCT/IB2017/052718, dated Sep. 5, 2017, 4 pages.
Kuzela L., et al., "Experimental evaluation of direct transventricular revascularization," Journal of Thoracic and Cardiovascular Surgery, 57(6):770-773 (Jun. 1969).
Laborde et al., "Percutaneous Implantation of the Corevalve Aortic Valve Prosthesis for Patients Presenting High Risk for Surgical Valve Replacement," EuroIntervention, 1(4):472-474 (Feb. 2006).
Mills N.L., et al., "Valvulotomy of valves in the saphenous vein graft before coronary artery bypass," The Journal of Thoracic and Cardiovascular Surgery, 71 (6):878-879 (Jun. 1976).
Munro I., et al., "The possibility of myocardial revascularization by creation of a left ventriculocoronary artery fistula," The Journal of Thoracic and Cardiovascular Surgery, 58(1):25-32 (Jul. 1969).
Nath J., et al., Impact of Tricuspid Regurgitation on Long-term Survival, Journal of the American College of Cardiology, vol. 43, No. 3, Feb. 2004, pp. 405-406.
Palacios., "Percutaneous Valve Replacement and Repair, Fiction or Reality?," Journal of American College of Cardiology, vol. 44(8), Oct. 2004, pp. 1662-1663.
Palmaz J.C., et al., "Expandable Intrahepatic Portacaval Shunt Stents: Early Experience in the Dog," American Journal of Roentgenology, 145(4):821-825 (Oct. 1985).
Palmaz J.C., et al., "Expandable Intrahepatic Portacaval Shunt Stents in Dogs with Chronic Portal Hypertension," American Journal of Roentgenology, 147(6):1251-1254 (Dec. 1986).
Partial European Search Report dated Feb. 28, 2012 in EP Patent Appl. Serial No. 11178135.7 (1257).
Partial European Search Report for Application No. 10168525.3-1269 dated Sep. 20, 2010, 5 pages.
Partial European Search Report for Application No. 07116242.4-2310 dated Jan. 14, 2008, 5 pages.
Partial European Search Report for Application No. 11153142.2-1257 dated Apr. 4, 2011, 5 pages.
Partial European Search Report for EP Patent Appl. Serial No. 07110318.8, dated Mar. 10, 2008, 6 pages.
Partial European Search Report for EP Patent Appl. Serial No. 10163478.0, dated Nov. 2, 2010, 6 pages.
Partial International Search Report for International Application No. PCT/EP2014/055044, filed Mar. 13, 2014, 7 pages.
Rogers J.H., et al., "The Tricuspid Valve: Current Perspective and Evolving Management of Tricuspid Regurgitation," Circulation, 119(20):2718-2725 (May 2009).
Preliminary Search Report (Rapport De Recherche Preliminaire) dated Jul. 2002 in French Patent Application No. 0110444 (2 pages).
Supplemental Search Report from EP Patent Office for EP Application No. 04813777.2, dated Aug. 19, 2011.
Supplemental Search Report from EP Patent Office for EP Application No. 04815634.3, dated Aug. 19, 2011.
Supplemental Search Report from EP Patent Office for EP Application No. 05758878.2, dated Oct. 24, 2011.
Supplementary European Search Report dated Feb. 1, 2012 in EP Patent Appl. Serial No. 09820051.2.
Triennial Review of the National Nanotechnology Initiative: "A Matter of Size", The National Academies Press, Washington DC,

(56) References Cited

OTHER PUBLICATIONS

V-13, Retrived from the Interent: URL: http://www.nap.edu/catalog/11752/a-matter-of-size-triennial-review-of-the-national-nanotechnology, Mar. 2006, 200 pages, (Parts 1-5).
Weyman AB et al., "Aortic Stenosis: Physics and Physiology—What Do the Numbers Really Mean?", Rev Cardiovasc Med. Jan. 2005, vol. 6(1), pp. 23-32.
Written Opinion for Application No. PCT/EP2006/012455, filed Dec. 22, 2006, 11 pages.
Written Opinion for Application No. PCT/EP2007/007413, dated Aug. 23, 2007, 5 pages.
Written Opinion for Application No. PCT/EP2011/058506, dated May 24, 2011, 5 pages.
Written Opinion for Application No. PCT/EP2014/065817, dated Jul. 23, 2014, 7 pages.
Written Opinion for PCT/EP2006/010023 dated Oct. 17, 2006, 10 Pages.
Written Opinion for PCT/EP2012/067714 dated Sep. 11, 2012, 5 Pages.
Extended EP Search Report dated Sep. 24, 2020 in EP Patent Appl. Serial No. 20165841.6 (JVT-0280).
Topol, Eric, Textbook of Interventional Cardiology, 4th Ed; Chapter 24: "Endovascular Options For Peripheral Arterial Occlusive and Aneurysmal Disease," Saunders, pp. 499-503, 949-953 (Dec. 2003).

\* cited by examiner

HEART VALVE MIMICRY

CROSS-REFERENCE TO RELATED APPLICATIONS

This application is a U.S. national stage filing under 35 U.S.C. § 371 of International Application No. PCT/IB2018/050438 filed on Jan. 25, 2018, which claims the benefit of priority to U.S. Provisional Application No. 62/451,296 filed on Jan. 27, 2017.

DESCRIPTION

The present disclosure relates to a stent supported replacement heart valve useful in transcatheter treatment of a stenosis (narrowing) of a cardiac valve and/or a cardiac valve insufficiency.

The present disclosure also relates to an endoprosthesis (prosthesis) designed for anatomical positioning and mimicking the endogenous heart valve in a number of aspects exhibiting less interference and less side effects as known from prior art heart valves.

Specifically, the present disclosure also relates to a collapsible and expandable prosthesis incorporating a stent that can be delivered to the implant site using a catheter for treatment of a stenosis (narrowing) of a cardiac valve and/or a cardiac valve insufficiency.

The expression "narrowing (stenosis) of a cardiac valve and/or cardiac valve insufficiency" may include a functional defect of one or more cardiac valves, which is either genetic or has developed. A cardiac defect of this type might affect each of the four heart valves, although the valves in the left ventricle (aortic and mitral valves) are affected much more often than the right-sided part of the heart (pulmonary and tricuspid valves). The functional defect can result in narrowing (stenosis), inability to close (insufficiency) or a combination of the two (combined vitium). This disclosure relates to an endoprosthesis that includes an expandable stent capable of being implanted transluminally in a patient's body and enlarged radially or radially self-expanding after being introduced percutaneously or in any other known minimally invasive manner for treating such a heart valve defect.

In some treatments of severe narrowing of a cardiac valve and/or cardiac valve insufficiency, the narrowed or diseased cardiac valve is replaced with an endoprosthesis. Biological or mechanical valve models, which are typically surgically sewn into the cardiac valve bed through an opening in the chest after removal of the diseased cardiac valve, are used for this purpose. This operation necessitates the use of a heart-lung machine to maintain the patient's circulation during the procedure and cardiac arrest is induced during implantation of the prosthesis. This is a risky surgical procedure with associated dangers for the patient, as well as a long post-operative treatment and recovery phase. Such an operation can often not be considered with justifiable risk in the case of polypathic patients.

Minimally-invasive forms of treatment have been developed over the past decade which are characterized by allowing the procedure to be performed under local anesthesia. One approach provides for the use of a catheter system to implant a self-expandable stent to which is connected a collapsible valve that is, e.g., made from pericardial tissue. Such a self-expandable endoprosthesis can be guided via a catheter system to the implantation site within the heart through an inguinal artery or vein. After reaching the implantation site, the stent can then be released and allowed to self-expand.

A stent may be comprised of, for example, a plurality of self-expanding longitudinal stent segments, the segments being articulated relative to one another. In order to anchor the stent securely in position in an appropriate blood vessel close to the heart, anchoring barbs may be used to engage with the vascular wall.

An expandable stent for the fastening and anchoring of an endoprosthesis is known from publication DE 10 010 074 A1, whereby the stent is essentially formed from wire-shaped, interconnected segments. DE 10 010 074 A1 proposes a stent for fastening and anchoring an endoprosthesis, the stent having different arched elements which assume the function of fastening and supporting the valvular prosthesis at the site of implantation. Specifically, three identically-configured positioning arches spaced 120° from one another respectively are used. These positioning arches are connected to one another by means of solid body articulations. In addition to the positioning arches, complementary curved retaining arches serve to anchor the endoprosthesis by pressing radially against the vascular wall following the unfolding of the stent.

On the one hand, state of the art procedures and prostheses designs emphasize the convenience of the minimally invasive access and deployment procedure. On the other hand, known prosthesis design focuses on valve functions upon deployment, e.g., durability of the valve sutures to the stent. Other aspects relate to the question of whether the prosthesis may remain in its position when the heart is pumping, e.g., that substantial forces act on the endoprosthesis during the filling phase of the heart cycle (diastole) and whether this can lead to endoprosthesis displacement longitudinally relative to the stent. Another focus of the prior art was the aspect of providing a secure seal to avoid peri-valvular leakage. Moreover, in the past there was awareness of positioning aspects like avoiding blockage of the coronary artery ostia (inlet orifice of coronaries) and the fact that such an interference of the prosthesis can lead to fatal coronary ischemia and myocardial infarction.

However, the prior art approaches and solutions focus on implantation procedures, basic valve functions and leakage aspects. Immediate and long term side effects of such a transcatheter heart replacement procedure and mimicking the endogenous heart valve are not at all addressed, or if mentioned, this aspect is not sufficiently addressed by the prior art.

Moreover, current trans aortic valve replacement therapy (TAVR) and known devices used in this procedure involve a number of disadvantages and risks like increased rate of stroke (about 4 to 6%) or the need for pacemaker implantation in treated patients depending on the device up to 25%. These issues are not sufficiently addressed or solved in known devices.

The prior art moreover does not appreciate the entire complexity of heart valve replacement therapy with regards to the functional implications, implant side effects such as pacemaker rate and the long term, post-procedural implications of such a treatment as well as with regards to sustainable long term effectiveness.

One problem of prior art approaches is that the prostheses do not sufficiently mimic the endogenous heart valve and accordingly, implantation of prior art prostheses results in an interference on a number of levels with the patients' heart and the endogenous heart function as well as a potentially disadvantageous impact on durability of the heart valve replacement therapy and unwanted long term side effects. Accordingly, the known transcatheter heart valve treatments do not represent an adequate and long-term solution for patients.

In view of the problems outlined above, one object of certain embodiments of the present application is to provide transcatheter heart valve prostheses with reduced side effects upon implantation in a patient, or at least to reduce or avoid the disadvantages of the prior art.

Another object of certain embodiments of the present application is to provide transcatheter heart valve prostheses exhibiting a reduced interference or substantially minimal interference with the endogenous functions of the heart of a patient, or at least to reduce or avoid the disadvantages of the prior art.

Another object of certain embodiments of the present application is to provide transcatheter heart valve prostheses which exhibit structural features which represent a long-term, durable transcatheter heart valve treatment of a patient, or at least to reduce or avoid the disadvantages of the prior art.

SUMMARY OF THE DISCLOSURE

In one aspect, the disclosure relates to a heart valve replacement prosthesis which may have improved prosthesis alignment properties.

In another aspect, the disclosure relates to a heart valve replacement prosthesis comprising commissure and annulus alignment means.

In another aspect, the disclosure relates to a heart valve replacement prosthesis comprising one or more of the following characteristics which, alone or in combination, may provide for better of mimicking the endogenous heart valve and may lead to less interference with the patient's heart:

1—Number of cells per $cm^2$ area is 2 to 6, and more preferably 3.7 to 5.1 in the inflow end region and 1 to 4, and more preferably 1.9 to 2.5 in outflow end region, or/and 2—In the inflow end region the ratio of area of any given cell to a neighboring cell is 0.25 to 4, and more preferably 1, or/and 3—In the inflow end region the ratio of height of any given cell to a neighboring cell is 0.5 to 2, and more preferably 1, or/and 4—In the inflow end region the aspect ratio of all cells is between 1 to 2, more preferably 1.5 to 1.6. Aspect ratio may be defined as a ratio of height to width of cells, or/and 5—In the outflow end region, aspect ratio of cells varies from 1 to 3, and more preferably 1.1 to 2.9. Aspect ratio may be defined as a ratio of height to width of cells, or/and 6—In the outflow end region, the cells vary in area in a single circumferential row and the area of adjacent cells in circumferential rows varies from 5 to 250 $mm^2$, and more preferably 7 to 198 $mm^2$, or/and 7—In the outflow end region, the cell heights vary in a single circumferential row and the height of adjacent cells in circumferential rows varies from 3 to 30 mm, and more preferably 6 mm to 25 mm.

In another aspect, the disclosure relates to a heart valve replacement prosthesis that may exhibit advantageous hemodynamics and mimic or essentially mimic the natural hemodynamics of native valve function.

In another aspect, the disclosure relates to a method of implantation of a replacement heart valve prosthesis.

In another aspect, the disclosure relates to a method of treating a diseased or stenotic heart valve or otherwise dysfunctional heart valve.

DETAILED DESCRIPTION OF THE DISCLOSURE

Figure 1:
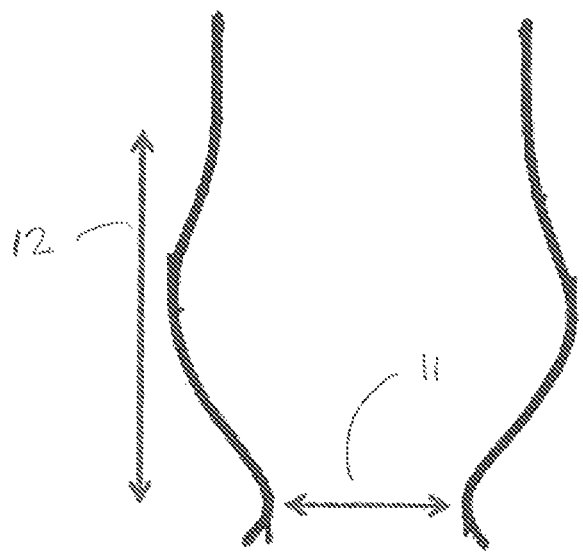
FIG. 1 describes the annulus diameter (11) and the annulus-to-commissure distance (12) which are relevant in certain aspects of the disclosure.

As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" as used herein is used in the sense of "example," rather than "ideal."

As used herein, the terms "about," "substantially," and "approximately," may indicate a range of values within +/−5% of a stated value.

At least some problems of the prior art may be solved by a replacement heart valve prosthesis comprising a stent component and a valve component characterized by a valve ratio of annulus to commissure distance to annulus diameter of about 1.01 to 1.14 and preferably of about 1.03 to 1.04, or/and the number of cells per $cm^2$ area is about 2 to 6 and more preferably 3.7 to 5.1 in the inflow end region and about 1 to 4 and more preferably 1.9 to 2.5 in the outflow end region, or/and in the inflow end region the ratio of area of any given cell to a neighboring cell is about 0.25 to 4 and more preferably about 1, or/and in the inflow end region the ratio of height of any given cell to a neighboring cell is 0.5 to 2 and more preferably 1, or/and wherein the inflow end region the aspect ratio of all cells is about 1 to 2 and more preferably about 1.5 to 1.6, or/and wherein the outflow end region the aspect ratio of cells varies from about 1 to 3, preferably about 1.1 to 2.9 or/and wherein in the outflow end region the cells vary in area in a single circumferential row and the area of adjacent cells in circumferential rows varies from about 5 to 250 $mm^2$, preferably about 7 to 198 $mm^2$ or/and wherein the outflow end region, the cell heights vary in a single circumferential row and the height of adjacent cells in circumferential rows varies from about 3 mm to 30 mm and more preferably from about 6 mm to 25 mm, or/and a radial force distribution of the prosthesis and the stent where about 15 to 25% of the radial force is provided by the annulus region and about 75 to 85% of the radial force provided by the supra-annulus region or/and the distance of the proximal end of the commissure alignment means to the distal end of the inflow end section is 4 to 12 mm, preferably 7.5 to 9 mm.

One advantage of certain embodiments of the disclosure is that they provide a means to align the commissures of the prosthesis with the native valve commissures. This advantage may be achieved by positioning means that protrude into the native valve pockets or by positioning means that achieve the alignment by way of self-aligning to the native commissures. Accordingly, the aligning means are attached or are a part of the prosthesis as appropriate for the respective purpose, e.g., to be positioned in the native valve pockets or at the native commissures, and thus these means protrude some distance or length from the main body of the prosthesis or they may represent an aligning means of the prosthesis to fit directly to the native commissures.

Another advantage of certain embodiments of the disclosure is that the stent is designed to reduce or essentially entirely avoid the risk of stenosis. For patients with aortic stenosis, the supra-annulus region, particularly the valve leaflets, is the most diseased area and it has been shown in TAVR procedures that stenosis occurs primarily within and around this region. At least one embodiment of the disclosure provides one solution in this respect by way of its specific design. The stent that supports the pericardial valve of the prosthesis may have differentiating chronic outward force (CoF) along the length of the THV. It may provide essentially the most outward force in the diseased area, e.g., supra-annulus region, and lower outward force in the annulus region of the native vessel. This may be useful because stenosis occurs primarily in the valve leaflets in the supra-annulus region and not in the annulus region.

The design and geometry of the stent described in this disclosure may achieve a radial force distribution of about 15 to 25% of the radial force provided by the annulus region and about 75 to 85% of the radial force provided by the supra-annulus region.

Another advantage of certain embodiments of the disclosure is that the specific design of the prosthesis may provide an anatomical alignment beyond pure commissure alignment. Hence, the structural alignment of the prosthesis with the native valve described in certain embodiments of the disclosure may preserve flow dynamics similar or essentially similar to the endogenous native valve with fewer side effects in comparison to prior art replacement heart valves.

The advantages of certain embodiments of the disclosure may be achieved in one aspect by the strut design, strut dimensions and strut distribution.

The advantages of certain embodiments of the disclosure are also achieved in one aspect by way of a stent cell density and stent cell distribution in different sections of the stent. The inflow end region at the distal end of the stent is generally located below the annulus in the ventricle and the outflow end region is generally located at the proximal end of the stent above the annulus. Both regions exhibit a specific stent cell or/and material distribution which may contribute to the advantageous functional aspects of the disclosure.

Another advantage is that the prosthesis provides in one aspect for "circumferential alignment" of the prosthesis valve commissures and replacement valve essentially with the endogenous commissures and valve leaflets. This may preserve natural valve functionality with respect to circumferential alignment and may be relevant for minimizing or eliminating unwanted side effects due to any potential change in flow pattern. "Circumferential alignment" with regard to the disclosure may relate to the alignment of the prosthesis commissures to the natural commissures. "Axial alignment" may relate to the alignment of the vertical level of the replacement valve with the endogenous valve. One may achieve essential circumferential and axial alignment of both replacement commissures and valve with their endogenous counterparts. Accordingly, such structural alignment may achieve flow dynamics and pressure distribution after implantation of the replacement heart valve prosthesis and during heart function that resembles and essentially mimics natural heart valve function.

Another advantage is that the prosthesis described in this disclosure may replicate the hemodynamic properties of the native aortic valve. Circumferential alignment of the commissures combined with alignment of the height of the prosthetic leaflets with the height of the native leaflets results in the prosthetic valve opening and closing in a similar manner and position as the native valve, thus may preserve the natural flow dynamics of the native valve. Also, the prosthesis may not block the sinuses of the aortic root with the stent frame or the tissue which allows blood to freely flow in areas when the valve is closed and may not interfere with the natural formation of eddy currents in the region.

FIG. 1 describes the annulus diameter dimension (horizontal arrows) and the endogenous annulus to upper commissure edge (proximal endogenous commissure edge) distance (vertical arrows). The disclosure achieves an alignment and relative positioning to mimic the endogenous dimensions without extending the prosthesis into heart areas such as the ascending aorta or left ventricle. Advantageously the prosthesis may avoid interference with endogenous functional areas or areas of functional significance, and also may avoid issues or complications that arise from TAVR procedures such as perivalvular leak and the need for permanent pacemaker implantation.

The term "aortic valve insufficiency", or "aortic insufficiency" for short, may refer to the defective closing of the heart's aortic valve and the diastolic reverse flow of blood from the aorta into the left ventricle as a result. Depending on the severity of the aortic insufficiency and the extent of resistance to aortic depletion, the volume of reverse flow can be up to two thirds of the left ventricle's ejection volume (normal cardiac output 40 to 70 ml). This results in a characteristically high blood pressure amplitude. This regurgitated blood flow increases the diastolic filling of the left chamber and leads to a volume overload of this section of the heart, a consequence of which is eccentric hypertrophy.

Structural features which contribute to some embodiments of the disclosure and which may advantageously contribute are the alignment of the THV prosthesis leaflets with the geometry of the endogenous valve leaflets, and/or the alignment of the THV commissures with the endogenous valve commissures and/or the THV stent cell seize over the length of the THV, e.g. a higher density of cells in the annulus region and a lower density of cells in the outflow region.

In another aspect, structural features which contribute to the advantageous results of the prosthesis are commissure alignment means, a tissue fastening portion and the prosthesis alignment with the endogenous leaflet geometry and the distal distance of the commissure alignment means to the distal end of the THV.

In preferred embodiments, the disclosure relates to a prosthesis as described above wherein the stent further comprises at least one alignment means, preferably two, three, four, five or six alignment means.

In another aspect, the prosthesis of the disclosure is characterized in that the alignment means is a feeler to be introduced into the native cusp(s) or/and a commissure alignment means to engage with the native valve commissure(s) and which is part of or fixed to the proximal end of the prosthesis.

In another aspect, the prosthesis of the disclosure is characterized in that the stent further comprises a fastening portion for fixation of the valve tissue, preferably pericardial tissue. Preferably the fastening portion is an arch, preferably comprising holes or rails or notches.

In another aspect, the disclosure relates to the use of the prosthesis as described herein in the treatment of heart valve stenosis or heart valve insufficiency.

In another aspect, the disclosure relates to a method for treating heart valve stenosis or heart valve insufficiency comprising the steps of loading or using a preloaded prosthesis as described herein with a delivery catheter useful for vascular deployment, introducing the catheter in a patient's vasculature, protruding and positioning the catheter for deploying the prosthesis at the target site, releasing and deploying the prosthesis at the target site and retracting the catheter from the patient's vasculature.

Of particular advantage is the specific geometry of the prosthesis according to some embodiments of the disclosure, which may result in fewer side effects after implantation as compared with known replacement heart valves.

The prosthesis may be characterized by the following advantageous features with regards to stent and prosthesis design which may lead to superior long term functionality and/or less side effects. The prosthesis described in this disclosure may exhibit one of several of the following features in combination.

In one aspect the "dimensions" and relative proportions of stent features and sections to each other—and thus the prosthesis including valve support—are relevant to mimic and achieve desired prosthesis function in the patient and to reduce or essentially avoid unwanted side effects.

One can divide/define the prosthesis according to the disclosure in various sections. In one aspect, the prosthesis can be structured axially where the prosthesis has an inflow end region at a distal end of the frame section and an outflow region at a proximal end of the frame.

According to literature, the ratio of annulus to commissure distance (ACD) to annulus diameter (AD) is typically 0.85-1.14 with an average of 1.04 for patients (H. Ruel et. al. 1990).

Figure 2:
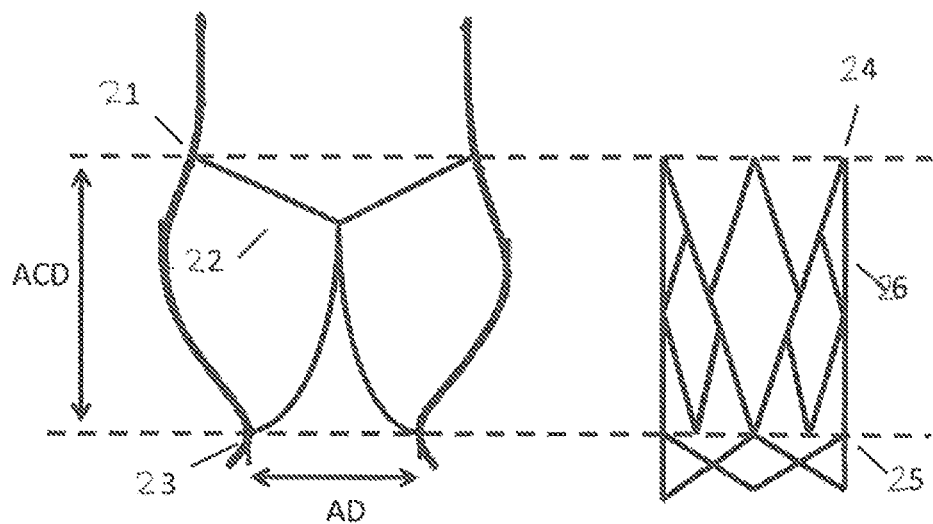
FIG. 2 describes an endogenous heart valve with the annulus diameter (AD) and annulus-to-commissure distance (ACD) relationship to an exemplary embodiment of the disclosure which may exhibit advantageous alignment and mimicry of the natural heart valve.

The design and geometry of the prosthesis described in this disclosure may achieve a valve ratio of annulus to commissure distance to annulus diameter of about 1.01 to 1.14 and preferably 1.03 to 1.04 depending on the annulus diameter of the native valve. Details are also depicted in FIG. 2.

Another aspect is that the annular geometry of the stent is independent from the geometry of the proximal section. In endogenous valve geometry, the annulus is generally non-circular and the commissure region is circular. In its implanted state, the stent of the prosthesis in the inflow end region maintains non-circular geometry while the proximal end of the outflow region maintains circular geometry. The stent achieves this by way of the height of the outflow end region, or the aforementioned ACD (annulus to commissure distance) to AD (annulus diameter) ratio.

In another aspect, one can also structure the prosthesis horizontally, e.g., in two sections which may be repeated two or three times.

Another aspect is the "circumferential stent cell distribution" or "circumferential area coverage of adjacent cells" in general or within regard to the different sections as described above.

Cell distribution according to the disclosure can be defined by various parameters and characteristics. Cell distribution features which create advantageous structural and functional performance characteristics after implantation, depending on the diameter of the native valve, include any one or more of the following:

Cell density, or the number of cells per $cm^2$ area can be about 2 to 6, preferably 3.7 to 5.1 in the inflow end region and about 1 to 4, preferably 1.9 to 2.5 in the outflow end region.

In the inflow end region, the ratio of area of any given cell to the neighboring cell is about 0.25 to 4, and more preferably about 1.

In the inflow end region, the ratio of height of any given cell to the neighboring cell is 0.5 to 2, and more preferably 1.

In the inflow end region, the aspect ratio of all cells is between 1 to 2, preferably 1.5 to 1.6. Aspect ratio may be defined as the ratio of cell height to cell width.

In the outflow end region, the aspect ratio of cells varies from about 1 to 3, and more preferably about 1.1 to 2.9. Aspect ratio may be defined as ratio of cell height to cell width.

In the outflow end region, the area of adjacent cells within circumferential rows varies from about 5 to 250 $mm^2$, and preferably about 7 to 198 $mm^2$.

In the outflow end region, the height of adjacent cells in circumferential row varies from about 3 to 30 mm, preferably from about 6 mm to 25 mm.

The stent (THV or prosthesis frame or support frame) of the prosthesis according to the disclosure may exert radial force on the aortic annulus and aortic root wall after deployment. This radial force may be primarily responsible for maintaining the prosthesis in the correct position. Frictional force between the aortic root/annulus and the stent may result from the radial force of the stent while the feelers create mechanical interference between each feeler tip and native aortic cusp.

Another aspect of the disclosure is the distance of the proximal end of the commissure alignment means to the distal end of the inflow end section, which is important for ensuring that the final height and position of the inflow end region is at a proper height in the annulus so as to prevent the need for permanent pacemaker implantation. In one particular embodiment of this disclosure, this distance is 4 to 12 mm, and most preferably 7.5 to 9 mm.

Figure 3:
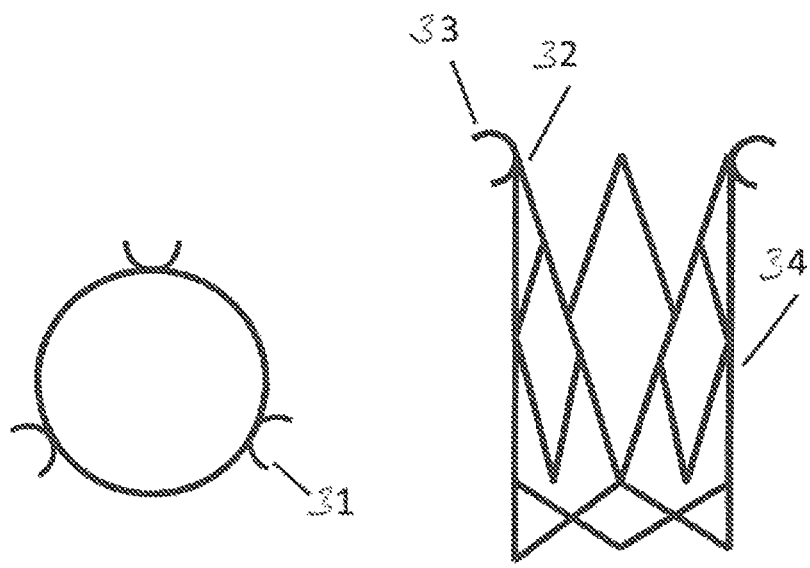
FIG. 3 describes a top view and a side view of an exemplary prosthesis with commissure alignment means which are positioned at the proximal end.

Another aspect is a commissure alignment means which is positioned at the proximal end of the prosthesis, which can be one, two or three means. It is formed to allow for engagement with the endogenous commissures of the valve and to prevent the prosthesis from axial movement in the distal direction (toward the ventricle) and to align the prosthesis with the endogenous commissures, thus mimicking the endogenous anatomical alignment. In combination with previously disclosed dimensional features of the prosthesis and the stent, this proximal commissure alignment means may also allow for vertical positioning of the distal inflow end region of the valve according to the position of the endogenous valve. This goal can alternatively be achieved by an alignment means (one, two or three) which is attached to or forms an integral part of the stent in combination with the previously disclosed dimensional features of the stent which are adapted accordingly. In FIG. 3 an exemplary embodiment is depicted.

The endogenous positioning of this disclosure can be achieved by way of using visual markers affixed to the prosthesis and monitoring them during the deployment procedure for correct positioning of the prosthesis. Of particular usefulness to some embodiments according to the disclosure can be alignment means as described above and below.

As described herein, stents may be radially expandable intravascular implants capable of being implanted vascularly, preferably transfemorally, and enlarged or self-expanding radially after being introduced percutaneously. The stents may be configured to be placed in a native diseased valve of a patient, such as a native stenotic aortic or pulmonary valve, using a minimally-invasive approach, such as a beating heart transapical procedure or a retrograde transaortic procedure. Although stents can be introduced into the body of the patient via any number of access points, a transvascular approach by femoral access or by transapical access for the aortic valve is preferred. However, this disclosure is not limited to these approaches.

A "native aortic valve" may be a valve with three leaflets or congenitally bicuspid with two leaflets.

An endoprosthesis may include an implant which (together with a stent to which the valvular prosthesis is affixed) functions as a check valve, opening to permit forward blood flow and closing to prevent retrograde flow. A valvular prosthesis may consist of at least two, and preferably of three leaflets, and a valve skirt on which the leaflets are connected.

At least one fastening portion extends along the longitudinal axis of the stent and comprises a plurality of fastening holes distributed in a longitudinal direction at discrete positions along the length of the at least one fastening portion. Thread or thin wire may be guided through each fastening hole to secure the valvular prosthesis to the stent. One advantage of this feature may be that longitudinal displacement of the valves relative to the stent is substantially minimized once implanted and so the prosthesis is not unduly disturbed or weakened as a result of the heart's peristaltic motion.

In addition, the stent may contain fastening means comprised of holes, and/or may include one or more notches to assist the seating and retaining of suture material. The notches also may assist with even attachment of the prosthesis to the stent and, similarly to the fastening holes, minimize longitudinal displacement of the prosthesis.

Extending from and between a pair of fastening portions is a fastening arch, to which valve tissue is attached or over which valve tissue is laid. In the expanded and implanted state of the stent and the valvular prosthesis affixed thereto, the fastening arch of the stent abuts against the vessel wall at least at the lower section of the stent in order to seal against leakage. Furthermore, with the fastening arch, the prosthesis tissue is separated and held away from other parts of the stent, thereby reducing the likelihood of these stent parts chaffing the tissue which, in turn may result in damage and weakening of the prosthesis.

The stent may comprise alignment means being an integral part of the stent or affixed thereto at the appropriate position of the stent which aide in alignment of the valve of the prosthesis with the natural commissures. Such means may be at least one feeler, or possible two or three feelers being positioned in the cusp(s) of the natural aortic valve. Such an alignment means may also be a commissure alignment means allowing for commissure alignment. This can be achieved by way of aligning the commissure alignment means themselves proximal to the endogenous commissures, and/or engaging with the proximal part of the endogenous commissures and thus aligning the prosthesis commissures with the endogenous commissures. Thus, the prosthesis' commissures may be positioned in alignment with the natural commissures in the patient's heart.

In an implanted configuration, at least one aligning means of the stent extends from the circumference of the stent in a generally radial direction.

In manufacturing the stent used in the valvular prosthesis according to a particular embodiment of the disclosure, the stent may exhibit a structure integrally cut from a portion of tube, in particular from a metal tube, which incorporates all components of the stent. It is also conceivable that the stent is cut out of a relatively large tube, e.g., a tube having a diameter which is larger compared with the diameter of the final stent in its collapsed configuration. For example, a tube having a diameter of approximately 10 mm may be used for cutting a specific stent pattern into this tube. Then the cut pattern may be different, as it may become necessary to crimp the stent to something smaller than what it was originally cut from. In particular, with this procedure it is possible to remove material during cutting and processing in a defined manner thereby enhancing the functionality of the final stent.

The stent preferably exhibits an integrally-formed structure which can transform from a first predefinable shape into a second predefinable shape, whereby the stent exhibits a first predefinable shape (collapsed shape) during insertion into the patient's body and a second predefinable shape (expanded shape) once implanted.

In a preferred embodiment, the stent exhibits in its first shape (collapsed shape) an outer diameter of approximately 4 to 8 mm and a length of between 30 mm and 48 mm. More precisely, the stent may exhibit in its first shape (collapsed shape) an outer diameter of approximately 4.0 to 8.0 mm, preferably 6.0 to 6.7 mm, and a length of between 33.0 mm and 45.0 mm, and preferably between 36.0 mm and 42.0 mm. This allows a prosthesis including the stent to be inserted easily into the patient's body, for example with a 19 F or 21 F delivery system, and to be used with an endoprosthesis having a diameter of between 19 mm and 28 mm. The afore-mentioned length specifications are the dimensions currently preferred, based on which the stent becomes suitable for the majority of patients to be treated.

In a particularly preferred realization, the stent comprises a valvular prosthesis, preferably a biological or pericardial valvular prosthesis, wherein the tissue component(s) of the valvular prosthesis is/are attached to the at least one fastening portion of the stent by means of a thread or the like. A commissure alignment means form also part of a preferred prosthesis, and in a more preferred embodiment the alignment means may lead to commissure and annulus alignment.

In one realization the stent and thus the prosthesis exhibits an advantageous radial compliance. The three sections of the stent as defined above may have a varying elasticity from section 1 to 2 to 3, or from section 1 to 2, respectively. The inflow end region (section 1) may exhibit a relative low elasticity and a relatively high stiffness. Section 2 (when dividing the prosthesis in two sections) may exhibit a higher elasticity and less stiffness. In case the stent is divided into three sections there exists a gradient from section 1 to section 2 to section 3.

Moreover, the advantageous stent design may allow for mimicking the endogenous valve behavior when the heart is pumping. One design feature and advantage of this aspect of the disclosure is that the annulus area of the prosthesis (or inflow end region) may essentially maintain its diameter. The proximal section (section 2 or sections 2 and 3, respectively) may allow movement due to their higher elasticity. Thus the commissures of the valve and the whole diameter of the stent (and thus of the prosthesis) are capable to move inwardly when the valve closes and the diameter of section 3 (or section 2 respectively) may be reduced and thus mimic the endogenous and native valve. Thus the inflow end of the prosthesis when implanted may resemble natural, endogenous functionality wherein the diameter remains essentially constant and the proximal prosthesis section varies its diameter and reduces its diameter when the valve closes. The diameter of the proximal end can reduce by 1 to 3 mm, or 1 to 2 mm.

A shape memory material is preferably used as the material for the stent, the material being designed such that the stent can transform from a temporary shape into a permanent shape under the influence of an external stimulus. The temporary shape is thereby the stent's first shape (e.g., the collapsed state of the stent), while the permanent shape is assumed in the stent's second shape (e.g., in the expanded state of the stent). In particular, use of a shape memory material such as Nitinol, e.g., an equiatomic alloy of nickel and titanium, allows for a particularly gentle implantation procedure when implanting the stent.

When manufacturing the stent preferably is made from a shape memory material, the stent structure is preferably shaped after it has been cut from a tube. It is conceivable that the stent is cut out of a tube having a diameter which is larger compared with the diameter of the final stent in its collapsed configuration. Then, the laser-processed tube is crimped thereby achieving the diameter of the stent in its collapsed configuration. Once the desired shape has been formed, this shape is "fixed", this process being known as "programming". Programming may be effected by heating the stent structure, forming the stent into the desired shape and then cooling the stent. Programming may also be effected by forming and shaping the stent structure at lower temperature, this being known as "cold stretching." The permanent shape is thus saved, enabling the stent to be stored and implanted in a temporary, non-formed shape. If an external stimulus then acts on the stent structure, the shape memory effect is activated and the saved, permanent shape restored.

A particularly preferred embodiment provides for the external stimulus to be a definable transformation temperature. It is thus conceivable that the stent material needs to be heated to a higher temperature than the transformation temperature in order to activate the shape memory effect and thus recover the stored, permanent shape of the stent. A specific transformation temperature can be preset by the relevant selection of the chemical composition of the shape memory material.

It is particularly preferred to set the transformation temperature to be in a range between 10° C. and the patient's body temperature, and preferably in the range of between 10° C. and room temperature. Doing so may be advantageous, especially with regards to the medical device being used as an implant in a patient's body. Accordingly, all that needs to be ensured in this regard when implanting the stent is that the stent is warmed up to room temperature or the patient's body temperature (37° C.) at the site of implantation to activate the shape memory effect of the stent material.

The present disclosure as described above relates to a heart valve prosthesis (endoprosthesis) comprising an expandable or self expanding stent and a valve used in the treatment of a stenosis (narrowing) of a cardiac valve and/or a cardiac valve insufficiency. Furthermore, the present disclosure relates to a collapsible and expandable prosthesis incorporating a stent that can be delivered to the implant site using a catheter for treatment of a stenosis (narrowing) of a cardiac valve and/or a cardiac valve insufficiency. Although the stent and the valvular prosthesis affixed thereto can be used for replacing any of the four different heart valves, in particular the pulmonary valve and the aortic valve, the application of the disclosure for treatment of a diseased aortic valve has been described above only for reasons of simplification.

The above disclosure is intended to be illustrative and not exhaustive. This description may suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the disclosure such that the disclosure should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g., each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

REFERENCE NUMBER LIST

Figure 4:
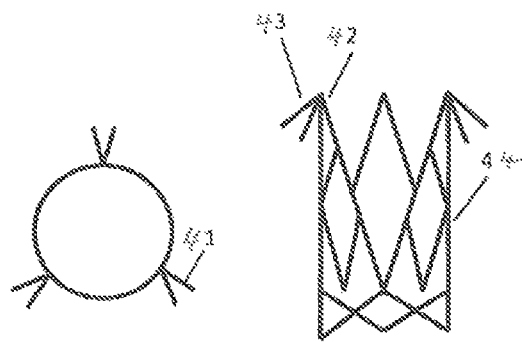
FIG. 4 describes another exemplary prosthesis with commissure alignment means which are positioned at the proximal end and represent a variation of the design in FIG. 3.
Figure 5:
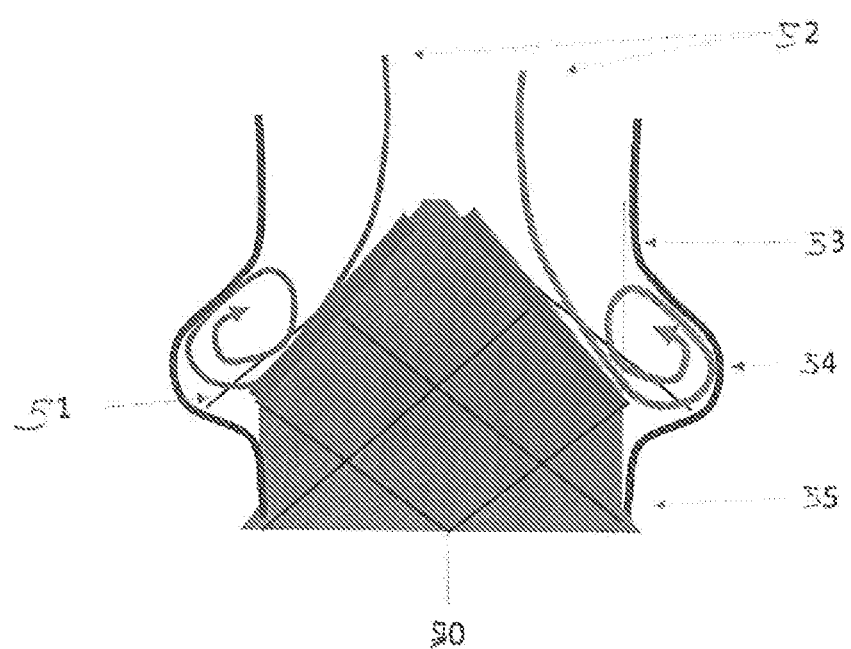
FIG. 5 describes an exemplary prosthesis of the disclosure placed in the endogenous heart valve, depicting the hemodynamic flow which may essentially mimic the natural hemodynamics of a fully functional endogenous heart valve.

FIG. 1:
11 Annulus diameter (AD)
12 annulus-to-commissure distance (ACD)
FIG. 2:
21 Native commissure
22 Native leaflet
23 Native annulus
24 THV commissure
25 THV inflow end section
26 THV
FIG. 3:
31 Commissure alignment mean
32 THV commissure
33 Commissure alignment mean
34 THV
FIG. 4:
41 Commissure alignment mean
42 THV commissure
43 Commissure alignment mean
44 THV
FIG. 5:
50 Valve
51 Alignment means
52 Flow
53 STJ 54 Sinus
55 Annulus

The invention claimed is:

1. A replacement heart valve prosthesis comprising a stent component and a valve component, wherein:
   the valve component has a valve ratio of annulus to commissure distance (ACD) to annulus diameter (AD) of 1.01 to 1.14, the ACD being a distance between a proximal end of a commissure portion and a proximal end of an annulus portion; and
   the stent component comprises an inflow end region and an outflow end region each comprising a plurality of cells, wherein in the inflow end region, a ratio of area of a given cell to a neighboring cell is 0.25 to 4, a ratio of height of the given cell to the neighboring cell is 0.5 to 2, or an aspect ratio of all cells of the inflow end region is 1 to 2, and wherein in the outflow end region, aspect ratios of a first cell and a second cell in a single circumferential row vary with respect to one another from 1 to 3, areas of the first cell and the second cell vary with respect to one another from 5 mm$^2$ to 250 mm$^2$, or heights of the first cell and the second cell vary with respect to one another from 3 mm to 30 mm.

2. The prosthesis according to claim 1, wherein the stent component includes at least one feeler for aligning the stent component relative to a native heart valve.

3. The prosthesis according to claim 2, wherein the at least one feeler is configured to be introduced into a native cusp of the native heart valve.

4. The prosthesis according to claim 3, wherein a distance from a proximal end of the at least one feeler to a distal end of the inflow end region of the stent component is 4 mm to 12 mm.

5. The prosthesis according to claim 4, wherein the distance from the proximal end of the at least one feeler to the distal end of the inflow end region is 7.5 mm to 9 mm.

6. The prosthesis according to claim 2, wherein the stent component includes three feelers for aligning the stent component relative to native cusps of the native heart valve.

7. The prosthesis according to claim 1, wherein the valve component comprises tissue, and the stent component further comprises an arch for fixation of the valve tissue.

8. The prosthesis according to claim 7, wherein the valve tissue comprises pericardial tissue.

9. The prosthesis according to claim 7, wherein the arch comprises holes, rails, or notches.

10. The prosthesis according to claim 1, wherein the valve ratio of ACD to AD is 1.03 to 1.04.

11. The prosthesis according to claim 1, wherein a number of cells per cm$^2$ area of the stent component is 2 to 6 in the inflow end region, and 1 to 4 in the outflow end region.

12. The prosthesis according to claim 11, wherein the number of cells per cm$^2$ area of the inflow end region is 3.7 to 5.1.

13. The prosthesis according to claim 11, wherein the number of cells per cm$^2$ area of the outflow end region is 1.9 to 2.5.

14. The prosthesis according to claim 1, wherein, in the inflow end region:
   the ratio of area of the given cell to the neighboring cell is 1;
   the ratio of height of the given cell to the neighboring cell is 1; and
   the aspect ratio of all cells of the inflow end region is 1.5 to 1.6.

15. The prosthesis according to claim 1, wherein, in the outflow end region:
   the aspect ratios of the first cell and the second cell vary from 1.1 to 2.9;
   the areas of the first cell and the second cell vary from 7 mm$^2$ to 198 mm$^2$; and
   the heights of the first cell and the second cell vary from 6 mm to 25 mm.

16. The prosthesis according to claim 1, wherein the prosthesis has a radial force, wherein 15 to 25% of the radial force is provided by an annulus region, and 75 to 85% of the radial force is provided by a supra-annulus region.

17. A replacement heart valve prosthesis comprising a stent component and a valve component, wherein:
   the valve component has a valve ratio of annulus to commissure distance (ACD) to annulus diameter (AD) of 1.01 to 1.14, the ACD being a distance between a proximal end of a commissure portion and a proximal end of an annulus portion; and
   the stent component comprises:
      an inflow end region and an outflow end region each comprising a plurality of cells, a number of cells per cm$^2$ area being 2 to 6 in the inflow end region and 1 to 4 in the outflow end region; and
      at least one feeler configured to engage with a native commissure of a native heart valve, the at least one feeler being part of, or fixed to, a proximal end of the prosthesis.

18. A method for treating heart valve stenosis or heart valve insufficiency comprising
   introducing a catheter preloaded with the prosthesis according to claim 1 in a patient's vasculature,
   positioning the catheter for deploying the prosthesis at a target site,
   releasing and deploying the prosthesis at the target site, and
   retracting the catheter from the patient's vasculature.

19. The method of claim 18, further comprising loading the prosthesis into the catheter before the step of introducing the catheter in the patient's vasculature.

* * * * *